United States Patent
Previte et al.

(10) Patent No.: US 9,279,154 B2
(45) Date of Patent: Mar. 8, 2016

(54) APPARATUS AND METHODS FOR KINETIC ANALYSIS AND DETERMINATION OF NUCLEIC ACID SEQUENCES

(71) Applicant: ILLUMINA, INC., San Diego, CA (US)

(72) Inventors: Michael Previte, Carlsbad, CA (US); Molly He, San Diego, CA (US); Rigo Pantoja, San Diego, CA (US); Cheng-Yao Chen, San Diego, CA (US); Chunhong Zhou, Encinitas, CA (US)

(73) Assignee: Illumina, Inc., San Diego, CA (US)

( * ) Notice: Subject to any disclaimer, the term of this patent is extended or adjusted under 35 U.S.C. 154(b) by 407 days.

(21) Appl. No.: 13/722,979

(22) Filed: Dec. 20, 2012

(65) Prior Publication Data

US 2013/0165328 A1 Jun. 27, 2013

Related U.S. Application Data

(60) Provisional application No. 61/578,684, filed on Dec. 21, 2011.

(51) Int. Cl.
*C12Q 1/68* (2006.01)

(52) U.S. Cl.
CPC ........ *C12Q 1/6874* (2013.01); *C12Q 2537/149* (2013.01); *C12Q 2561/12* (2013.01); *C12Q 2565/518* (2013.01); *C12Q 2565/537* (2013.01)

(58) Field of Classification Search
None
See application file for complete search history.

(56) References Cited

U.S. PATENT DOCUMENTS

| | | | |
|---|---|---|---|
| 6,787,308 B2 * | 9/2004 | Balasubramanian et al. .... | 506/9 |
| 6,908,736 B1 | 6/2005 | Densham | |
| 7,057,026 B2 | 6/2006 | Barnes et al. | |
| 7,414,116 B2 | 8/2008 | Milton et al. | |
| 7,427,673 B2 | 9/2008 | Balasubramanian et al. | |
| 7,888,073 B2 | 2/2011 | Densham | |
| 8,241,573 B2 | 8/2012 | Banerjee et al. | |
| 2007/0196846 A1 * | 8/2007 | Hanzel et al. ..................... | 435/6 |
| 2008/0070236 A1 * | 3/2008 | Densham ........................... | 435/6 |
| 2008/0287305 A1 * | 11/2008 | Fuller .................. | C12Q 1/6834 506/4 |
| 2009/0036317 A1 * | 2/2009 | Guilbeau .......................... | 506/6 |
| 2009/0286245 A1 | 11/2009 | Bjornson et al. | |
| 2010/0047802 A1 * | 2/2010 | Bjorson ............... | C12Q 1/6869 435/6.18 |
| 2010/0111768 A1 | 5/2010 | Banerjee et al. | |
| 2010/0279288 A1 * | 11/2010 | Densham ........................... | 435/6 |
| 2011/0160077 A1 * | 6/2011 | Chaisson ............. | C12Q 1/6869 506/9 |
| 2011/0312529 A1 | 12/2011 | He et al. | |
| 2012/0009567 A1 * | 1/2012 | Fedorov ............... | C12Q 1/6869 435/6.1 |
| 2012/0270305 A1 | 10/2012 | Reed et al. | |

FOREIGN PATENT DOCUMENTS

| | | |
|---|---|---|
| WO | WO 91/06678 | 5/1991 |
| WO | WO 00/36152 | 6/2000 |
| WO | WO 00/70073 | 11/2000 |
| WO | WO 02/04680 | 1/2002 |
| WO | WO 02/072892 | 9/2002 |
| WO | WO 02/095070 | 11/2002 |
| WO | WO 2005/010210 | 2/2005 |
| WO | WO 2005/065814 | 7/2005 |
| WO | WO 2005/080605 | 9/2005 |
| WO | WO 2007/123744 | 11/2007 |
| WO | WO 2009/056831 | 5/2009 |
| WO | WO 2009/145820 | 12/2009 |
| WO | WO 2010/068884 | 6/2010 |
| WO | WO 2010141390 A2 * | 12/2010 ........... C12Q 1/6827 |

OTHER PUBLICATIONS

Picha et al.Biochemistry 39.21 (2000): 6401-6409.*
Picha et al. Biochemistry 39.21 (2000):6401-6409.*
Santoso et al. (Conformational transitions in DNA polymerase I revealed by single-molecule FRET, PNAS, Jan. 12, 2010, vol. 107, No. 2, 715-720).*
Silva et al. (Using 2-Aminopurine Fluorescence to Measure Incorporation of Incorrect Nucleotides by Wild Type and Mutant Bacteriophage T4 DNA Polymerases, J Biol Chem. Oct. 25, 2002;277(43):40640-9. Epub Aug. 19, 2002).*
Roettger et al. (Mismatched and Matched dNTP Incorporation by DNA Polymerase Proceed via Analogous Kinetic Pathways, Biochemistry. Sep. 16, 2008;47(37):9718-27. Epub Aug. 22, 2008).*
Gong et al. (A quantitative stopped-flow fluorescence assay for measuring polymerase elongation rates, Anal Biochem. Aug. 1, 2009;391(1):45-55. Epub May 3, 2009).*
Tang et al. (Fluorescence-based assay to measure the real time kinetics of nucleotide incorporation during transcription elongation, J Mol Biol. Jan. 21, 2011;405(3):666-78. Epub Oct. 28, 2010).*
Christian et al. (Single-molecule measurements of synthesis by DNA polymerase with base-pair resolution, PNAS, vol. 106 No. 50, 21109-21114, Dec. 2, 2009).*
Joyce et al. (Techniques used to study the DNA polymerase reaction pathway, Biochim Biophys Acta. May 2010;1804(5):1032-40. Epub Aug. 7, 2009).*
Bentley, et al., "Accurate whole human genome sequencing using reversible terminator chemistry", Nature, 456, 2008, 53-59.

(Continued)

*Primary Examiner* — Stephanie K Mummert
*Assistant Examiner* — Aaron Priest
(74) *Attorney, Agent, or Firm* — John T. Murphy; Illumina, Inc.

(57) ABSTRACT

A method of distinguishing nucleotide sequences for different nucleic acid molecules including the steps of (a) mixing a plurality of different nucleic acid molecules with polymerase molecules and nucleotide molecules, wherein the different nucleic acid molecules are attached to a surface in the form of an array of nucleic acid features; (b) determining a transient state of the polymerase molecules at the nucleic acid features; and (c) identifying a subset of nucleic acid features that correctly incorporate the nucleotide molecules based on the transient state of the polymerase molecules at the nucleic acid features, thereby distinguishing the nucleotide sequences for the different nucleic acid molecules.

23 Claims, 22 Drawing Sheets

(56) References Cited

OTHER PUBLICATIONS

Bronson, et al., "Learning Rates and States from Biophysical Time Series: A Bayesian Approach to Model Selection and Single-Molecule FRET Data", Biophysical Journal, 97, 2009, 3196-3205.

Cheezum, et al., "Quantitative Comparison of Algorithms for Tracking Single Fluorescent Particles", Biophysical Journal, 1, 2001, 2378-2388.

Eid, J., et al., "Real-Time DNA Sequencing from Single Polymerase Molecules", Science 323, 2009, 133-138.

Hwang, et al., "Substituent effects on the pairing and polymerase recognition of simple unnatural base pairs", Nucleic Acids Research, vol. 34, No. 7, 2006, 2037-2045.

Johnson, "Transient State Kinetic Analysis of Enzyme Reaction Pathways", The Enzymes, XX, 1992, 1-61.

Joyce, et al., "Fingers-Closing and Other Rapid Conformational Changes in DNA Polymerase I (Klenow Fragment) and Their Role in Nucleotide Selectivity", Biochemistry, 47, 2008, 6103-6116.

Kuchta, et al., "The Kinetic Mechanism of DNA Polymerase I", Biochemistry, 26, 1987, 8410-8417.

Roy, et al., "A practical guide to single-molecule FRET", Nature Methods, 5, 2008, 507-516.

SANTOSO, "Conformational Transitions in DNA Polymerase I Revealed by Single-Molecule FRET", Proceedings of the National Academy of Sciences; vol. 107, No. 2, Jan. 12, 2010, 715-720.

* cited by examiner

ABSTRACT# APPARATUS AND METHODS FOR KINETIC ANALYSIS AND DETERMINATION OF NUCLEIC ACID SEQUENCES

This application is based on, and claims the benefit of, U.S. Provisional Application No. 61/578,684, filed Dec. 21, 2011, which is incorporated herein by reference in its entirety.

BACKGROUND

This disclosure relates generally to detection and characterization of nucleic acids. More specifically this disclosure relates to determining the sequences of nucleic acids.

One's genome provides a blue print for predicting many inherent predispositions such as one's likes and dislikes, talents, susceptibility to disease and responsiveness to therapeutic drugs. The human genome contains a sequence of over 3 billion nucleotides and it is the differences in just a fraction of those nucleotides that determines unique characteristics of an individual. The research community is making impressive strides in unraveling the link between genomic sequence and the living structures they encode. However, a more complete understanding will require that tens-of-thousands or millions of genomes be sequenced. Then scientists will be able to correlate the complexities of the genetic code with the variety of human characteristics. Furthermore, beyond the research effort, the costs must come down in order to usher in the day when each person will have a copy of their own personal genome so that they can sit down with their doctor to determine appropriate choices for a healthy lifestyle or a proper course of treatment.

Several commercial sequencing platforms are available, and although they provide an accurate tool for sequencing on the scale of entire genomes, they are still prohibitively expensive for wide deployment across large populations of individuals. What is needed is a reduction in the cost of sequencing that drives large genetic correlation studies carried out by research scientists and that makes sequencing accessible in hospitals and clinics to facilitate the informed treatment of individual patients making life changing decisions. The inventions set forth herein satisfy this need and provides other advantages as well.

BRIEF SUMMARY

The present disclosure provides a method of distinguishing nucleotide sequences for different nucleic acid molecules. The method can include the steps of (a) mixing a plurality of different nucleic acid molecules with polymerase molecules and nucleotide molecules, wherein the different nucleic acid molecules are attached to a surface in the form of an array of nucleic acid features; (b) determining a transient state of the polymerase molecules at the nucleic acid features; and (c) identifying a subset of nucleic acid features that correctly incorporate the nucleotide molecules based on the transient state of the polymerase molecules at the nucleic acid features, thereby distinguishing the nucleotide sequences for the different nucleic acid molecules. In a sequencing embodiment, the method can further include the steps of (d) removing the polymerase molecules from the nucleic acid features, thereby providing restored features; (e) mixing the restored features with polymerase molecules and a second species of nucleotide molecules, wherein the second species of nucleotide molecules is different from the species of nucleotide molecules in (a); and (f) repeating (b) and (c) for the restored features, thereby distinguishing the nucleotide sequences for the different nucleic acid molecules.

This disclosure also provides a system for determining sequences of nucleic acids from pre-equilibrium kinetic measurements of extension reactions for the nucleic acids. The system can include (a) an array having nucleic acid features with different nucleotide sequences; (b) a fluidic apparatus configured to deliver sequencing reagents to the array, wherein the sequencing reagents include polymerase molecules and nucleotide molecules for the nucleic acid extensions reactions; (c) a detection apparatus configured to obtain the kinetic measurements from the array at a resolution that distinguishes individual nucleic acid features of the array; (d) a control module including instructions for (i) directing the fluidic apparatus to deliver the sequencing reagents to the array at an initiation time point, and (ii) directing the detection apparatus to obtain the kinetic measurements during the pre-equilibrium time period relative to the initiation time point; and (d) an analysis module including instructions for (i) processing the kinetic measurements to determine binding of the polymerase molecules to the nucleic acid features at several points during the pre-equilibrium time period, thereby determining transient state of the polymerase molecules at the nucleic acid features, and (ii) identifying nucleic acid features that correctly incorporate the nucleotide molecules based on the transient state of the polymerase molecules at the nucleic acid features.

BRIEF DESCRIPTION OF THE DRAWINGS

FIG. 10 shows an expected insertion sequences that could be distinguished from experimental data.

DETAILED DESCRIPTION

This disclosure provides methods and apparatus for sequencing nucleic acids using polymerase pre-steady state kinetics. In particular embodiments, the methods and apparatus employ high speed delivery of reagents and real time detection. During a nucleic acid polymerization reaction, a polymerase exhibits distinct kinetics behavior when encountering a nucleotide cognate to a template base (i.e. a 'correct nucleotide') in contrast to when encountering a mismatched nucleotide. If fast mixing of reagents and real time detection of nucleic acids on the surface of an array are employed, this unique kinetics behavior can be detected and monitored by either a labeled polymerase or labeled nucleotides.

A sequencing method of the present disclosure can be implemented in a mode for single molecule detection or, alternatively, in a mode for ensemble level detection. Single molecule detection is carried out such that a reaction or other event occurring at an individual target nucleic acid is distinguished from similar events occurring at all other target nucleic acids. For example, individual target nucleic acid molecules that are attached to a surface of an array can be individually distinguished one from the other. In a particular embodiment of single molecule level detection, a synchronized scheme is used wherein each of four different nucleotide species is utilized sequentially in the formation of mixtures with a polymerase and a target nucleic acid. The polymerase can optionally have a detectable label.

Figure 1:
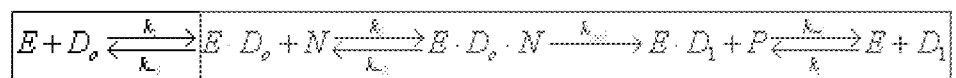
FIG. 1 shows (a) through synchronization of enzyme DNA binding (rapid mixing), the addition of the correct nucleotide gives rise to the more stable tertiary complex formation and subsequent catalytic chemistry step ($k_{pol}$). The duration of this event is dictated by both the catalytic step and the nucleotide binding to the active site. (b) The duration of the incorrect step is primary dictated by the $k_{-1}$ or the enzyme dissociation from the template DNA.
Figure 1:
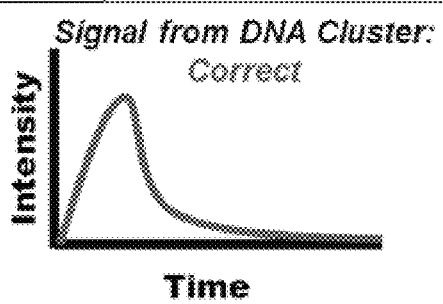
Figure 1:
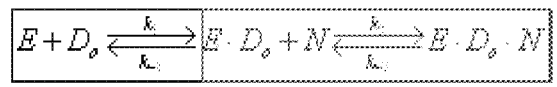
Figure 1:
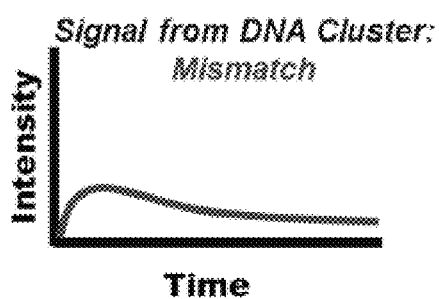

In particular embodiments, the binding of labeled polymerase to immobilized DNA clusters can be monitored, whereby the emission signal is detected from the labeled Enzyme/DNA complex formation (FIG. 1). Although not intended to be limiting, the following simplified kinetic model can provide a useful guide for understanding aspects of some of the embodiments of the sequencing methods set forth herein.

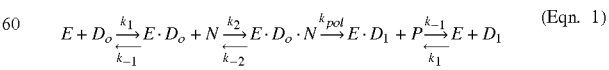

(Eqn. 1)

Equation 1 is understood to describe a minimal model describing DNA binding, nucleotide binding, nucleotide incorporation, and DNA dissociation. The first step in this pathway is the reversible binding of the polymerase to the DNA ($K_1$), which is concerted or followed by the nucleotide substrate binding to the enzyme/DNA complex to form a tertiary complex ($K_2$). Following the binding of the correct nucleotide in the polymerase active site, the enzyme undergoes a conformational change to the closed conformation (kinetically collapsed into $K_2$) that commits the enzyme to forward catalysis ($k_{pol}$). The simplification of nucleotide ground state binding an substrate induced fit has led to the use of $KA_{d,apparent}$ ($K_{d,app}$) to describe one step nucleotide binding ($K_2$) in the minimal model. Since these reactions are run well above the $K_d$ for the correct nucleotide binding to the polymerase active site and at high ionic strength, base discrimination is primarily driven by both Enzyme/DNA and Enzyme/DNA/dNTP binding kinetics. Translocation, a conformational change back to the "open" state, and $PP_i$ release occurs following nucleotide incorporation, and can collectively be grouped as post-chemistry steps. In this minimal model the steps following chemistry are assumed to be kinetically fast and can be omitted. Depending on the processivity of the polymerase, following the post-chemistry steps the enzyme can bind the next correct nucleotide or dissociate from the DNA ($K_1$).

In particular embodiments the sequencing scheme can employ a polymerase that is labeled and a signal can be recorded that arises from the polymerase/DNA and DNA$_{n+1}$ complex. It is possible to express the rates of consumption and formation of these complexes mathematically in the presence of a nucleotide:

$$\frac{d[ED_o]}{dt} = k_1[E][D_o] - k_{-1}[E \cdot D_o] \cdot [N] + k_{-2}[E \cdot D_o \cdot N] - k_2[E \cdot D_o][N] \quad \text{(Eqn. 2)}$$

$$\frac{d[ED_1]}{dt} = k_{pol}[E \cdot D_o \cdot N] - k_{-1}[E \cdot D_1] \cdot [P] + k_1[E][D_1][P] \quad \text{(Eqn. 3)}$$

The signals for the $E \cdot D_o$ and $E \cdot D_1$ need not be distinguished, and instead these terms can be redefined as the signal complex, SC, and Equations 2 and 3 are combined to derive the mathematical expression for rates of consumption and formation of the complex and subsequent signal dependence:

$$\frac{d[SC]}{dt} = k_1[E][D_o] - k_{-1}[SC_o] \cdot [N] + \quad \text{(Eqn. 4)}$$
$$k_{-2,corr}[SC_o \cdot N] - k_{2,corr}[SC_o][N] +$$
$$k_{pol}[SC_o \cdot N] - k_{-1}[SC_1] \cdot [P] + k_1[E][D_1][P].$$

Assuming negligible misincorporation in the presence of the mismatch nucleotide, which implies $k_{-2,mismatch} > k_{pol,mismatch}$, the rate of complex formation and consumption for the mismatch nucleotide, Equation 2, can be rewritten as follows:

$$\frac{d[SC]}{dt} = \quad \text{(Eqn. 5)}$$
$$k_1[E][D_o] - k_{-1}[SC_o] \cdot [N] + k_{-2,inc}[SC_o \cdot N] - k_{2,inc}[SC_o][N].$$

From these expressions, we can predict the potential differentiation power for this sequencing chemistry by estimating some of the kinetic constants in Equations 3 through 5.

Figure 19:
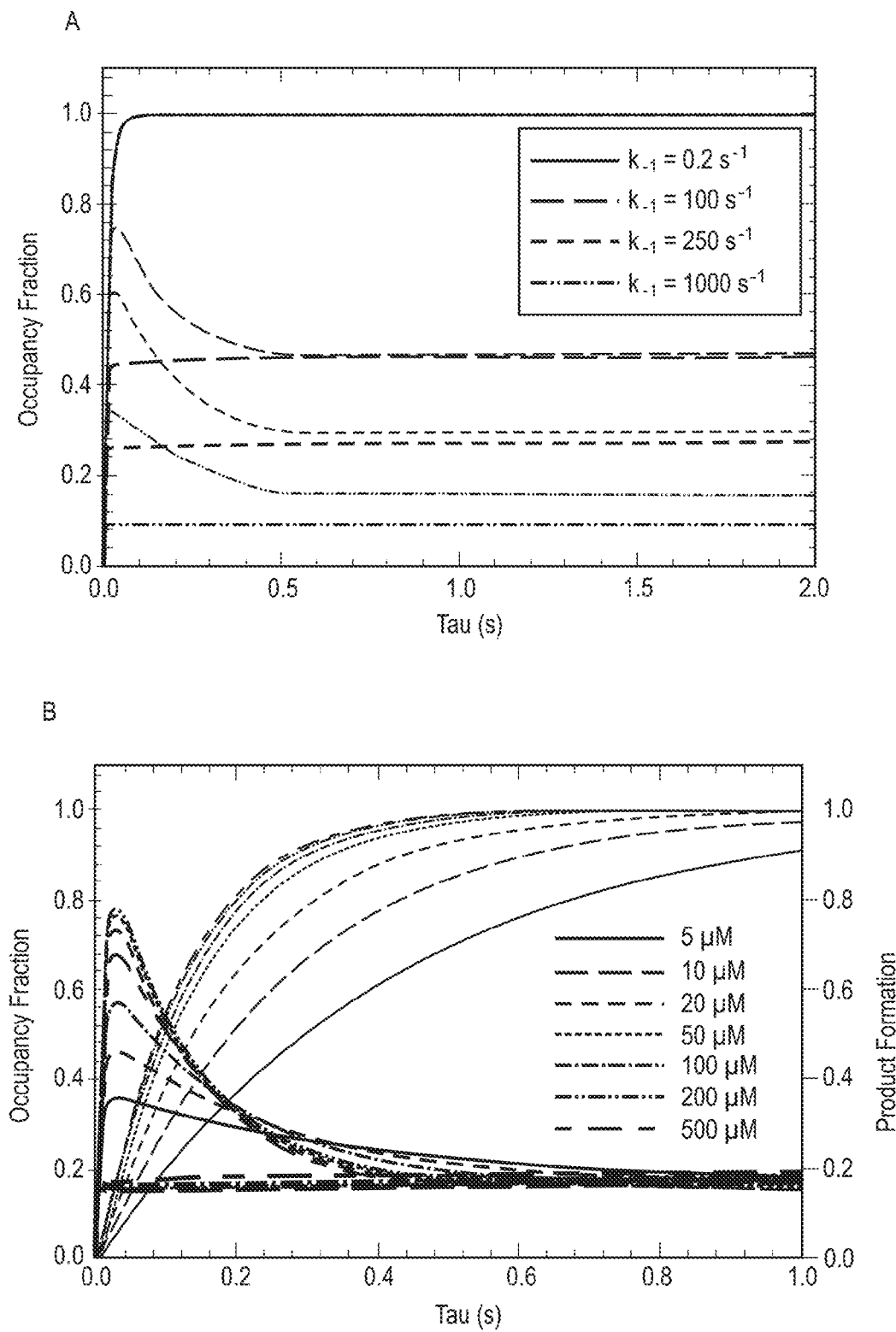
FIG. 19 shows A simulation of correct and mismatch complex formation at various DNA off rates ($k_{-1}$) and B simulation of correct and mismatch nucleotide concentration dependence on bright state formation and altered kinetics of correct nucleotide tertiary complex due to increased ionic strength.

Continuing with the model, if the binary E-D complex is stable, whereby $K_d$ for the DNA template is small, the signal from binary complex formation will deteriorate the discrimination power for this chemistry. In a simulation, the binary complex formation yields Enzyme/DNA complexes that are primarily driven by the enzyme affinity for the DNA template, $k_1$ and $k_{-1}$. For strong binding affinity, $k_{-1}$ is typically small and it is difficult to discriminate correct vs. mismatch base in the presence of [dNTP] (FIG. 19A). At higher ionic strength, which can be simulated by increasing DNA off rates, the affinity of the enzyme for the DNA decreases. The equilibrium favors enzyme dissociated from the DNA, minimizes binary complex formation, and the nucleotide binding step becomes increasingly important with regards to stabilizing the enzyme/DNA complex (FIG. 19A). By simulating the addition of varying concentrations of correct and mismatch nucleotides at high ionic strength, the equilibrium shifts towards complex formation for the correct nucleotide (FIG. 19B). Little complex formation is seen in the presence of increasing mismatch nucleotide. At higher nucleotide concentration, the correct dNTP/DNA/Enzyme complex is more stable yielding higher signal and the mismatch dNTP/DNA/enzyme complex remains unstable. These simulations suggest that it may be possible to combine high nucleotide concentration and ionic strength to create correct vs. mismatch base discrimination (FIG. 19B). FIG. 19A shows simulation of correct and mismatch complex formation at various DNA off rates ($k_{-1}$). Curves represent the fractional occupancy of bright states $ED_n$, $ED_nN_{correct}$, and $ED_{n+1}$ (for the correct nucleotide), and $ED_n$, $ED_nN_{mismatch}$, and $ED_{n+mismatch}$ (for the incorrect nucleotide). Increasing ionic concentration decreases the enzyme-DNA complex equilibrium (i.e. increases the value of $k_{-1}$). This shift in DNA binding equilibrium results in nucleotide binding driving reaction to the detectable bright state. Under low ionic condition ($k_{-1}=0.2$ sec$^{-1}$, solid traces) no difference between correct and mismatch signals is detected because DNA binding is favorable in the absence of nucleotide. In high ionic conditions (dashed traces) the disparity in binding affinities for correct versus mismatch nucleotide is observed and can be used as a basis for base calling. Generally, the high ionic strength traces for correct nucleotide show a rise in occupancy fraction followed by a fall, whereas the high ionic strength traces for incorrect nucleotide show a more immediate rise in occupancy fraction followed by a plateau. FIG. 19B shows simulation of correct and mismatch nucleotide concentration dependence on bright state formation. Simulation was performed under conditions such that the ionic strength of the buffer resulted in a DNA off-rate ($k_{-1}$) of 500 s$^{-1}$. The nucleotide concentration was varied from 5 µM (solid traces) to 500 µM (dashed traces). Increasing concentrations of correct nucleotide drive tertiary complex formation resulting in an increased fractional occupancy of the bright state. This is seen for the set of traces for correct nucleotide since they show a rise in occupancy fraction followed by a fall. Conversely, mismatch nucleotide binding over the same concentration range is weak and does not promote the detectable tertiary complex. This is evident from the set of traces for incorrect nucleotide that show a relatively immediate rise in occupancy fraction followed by a plateau. The altered kinetics of correct nucleotide tertiary complex due to increased ionic strength result in complete product formation with a $k_{pol}$ of 9 s$^{-1}$ and a $K_{d,apparent}$ of 30 µM. This is indicated by the set of traces showing a hyperbolic increase in product formation to a value above 0.8 at Tau of 1.0. Simulations were performed using a KinTek Global Kinetic Explorer (KinTek, Corp. Austin, Tex.).

Figure 2:
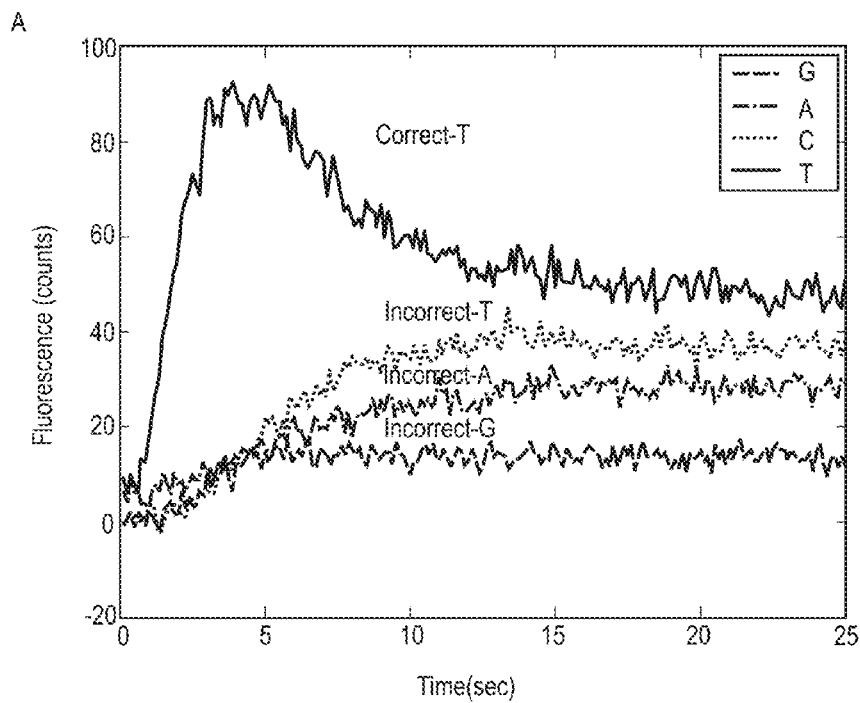
FIG. 2 shows waveforms produced from interaction of a fluorescently labeled polymerase with a nucleic acid in the presence of correctly matched and mismatched nucleotides (Panel A) and a table correlating waveform features with kinetic characteristics of the interactions (Panel B).

The events diagrammed in FIG. 1 can also occur at the ensemble level. However, at the ensemble level, the relatively long pulses that occur in the pre-equilibrium timeframe when a matched nucleotide is present can be summed up to display a unique waveform that is different from the waveform summed from the short pulses detected in the presence of a mismatched nucleotide. Exemplary waveforms that distinguish polymerase binding for correct (i.e. matched) nucleotides from incorrect (i.e. mismatched) nucleotides are shown in FIG. 2. The waveforms can form the basis of base discrimination using polymerase pre-steady state kinetics.

At the ensemble level, incorporation of a correct nucleotide species can be distinguished from interactions of mismatched nucleotide species when the collective species that are present at a detection site (e.g. a feature of an array) are effectively in phase. The state of being in phase can be achieved through control of mixing rate and chemistry rate. The mixing rate is a measure of the time it takes to reach a desired reactant concentration across a detection site, for example, across all species present at an array feature. Chemistry is typically the rate limiting process for reaching steady state. Generally, the mixing rate is convolved with the chemistry rate in the timeframe of pre-equilibrium detection. Signal acquisition time (e.g. the time during which signal will be recorded to generate a signal waveform) is also a factor that can be controlled during pre-equilibrium detection. One or more signals can be acquired during the signal acquisition time.

In one potential implementation, mixing rates can be much greater than chemistry rates such that the duration of the signal waveform is dominated by the chemistry rate. In this scheme, the signal acquisition time is limited by the chemistry rate and the mixing has a negligible contribution to the overall waveform. Thus, the acquired signal waveform can be directly used for base calling.

In another detection scheme, the mixing rate can be similar to or slower than the chemistry rate. As such, both chemistry and mixing rate limit the system reaching steady state. In this scheme, signal can be acquired as a convolution between mixing effect and chemistry. Signal acquisition time is determined by both terms. Acquired signal can be pre-processed to deconvolve the mixing effect. The deconvolved signal then can be used for base calling. Mixing rate can be increased as a way to make the deconvolution process more straightforward.

As shown in FIG. 2, the slope and amplitude of the rising phase is correlated to the association rate of the polymerase binding to the DNA in the presence of the nucleotide. In the instance of the correct nucleotide, the rising phase can be correlated to the DNA on rate (e.g. $k_1$). The rising slope and amplitude can also be correlated to the mixing rate, DNA off rate (e.g. $k_{-1}$), and the nucleotide binding in the active site of the polymerase when complexed to the DNA.

As described above, superior discrimination can be achieved by use of very fast mixing of reagents at the observation field (e.g. at one or more features on an array) coupled with real time detection. The mixing can occur on the sub-milliseconds timescale in accordance with available stopped-flow instrumentation. The fast mixing of reagents can be achieved using fast fluidics, active or passive mixing, and proper confinement (e.g. mix blousing) of the reaction to overcome limitations by diffusion. When fast mixing and appropriately time-gated detection are used the individual species in an ensemble will be apparently in phase. The dropping slope and length of the plateau in FIG. 2 can be correlated with some or all of the following properties: enzyme incorporation rate (e.g. $k_{cat}$ or $k_{pol}$), $k_{-2}$, $k_2$ and $k_{-1}$. Consequently, multiple kinetic steps are also involved in the ability to achieve correct vs. incorrect discrimination. The discrimination power of this method can be defined with respect to the kinetic rates of the reaction, such as $k_{pol}$, $k_{-2}$, $k_2$ and, $k_{-1}$, as set forth in further detail below.

A more detailed understanding of the compositions and methods of the present disclosure can be gained from the following definitions and exemplary embodiments.

As used herein, the term "binding," when used in reference to two molecules, means the process by which the molecules contact each other in a manner that results in a complex between the two molecules. The complex is typically reversible, for example, being mediated by non-covalent interactions. Accordingly binding can be characterized by association rates, dissociation rates and related kinetic parameters such as association rate constants and dissociation rate constants.

As used herein, the term "equilibrium," when used in reference to a reaction, means a state in which there is no net change in the amount of reactants or products of the reaction. For example, a binding reaction for a free polymerase and free nucleic acid that bind each other to form a polymerase-nucleic acid complex is at equilibrium when there is no net change in the amount of free polymerase, free nucleic acid and polymerase-nucleic acid complex. As used herein, the terms "binding", "equilibrium", "pre-equilibrium (i.e. pre-steady state), "binding rate constant" (i.e. $k_1$, $k_{on}$ or association rate constant), "dissociation rate constant," (i.e. $k_{-1}$ or $k_{off}$) and "catalytic rate constant" (i.e. $k_{pol}$ or $k_{cat}$) are intended to be consistent with the meaning of the terms as they are known in the art, for example, as described in Segel, *Enzyme Kinetics* John Wiley and Sons, New York (1975), which is incorporated herein by reference in its entirety. These terms can be used to describe any of a variety of interactions that occur in a particular reaction between polymerase, nucleotide and nucleic acid. For example, the terms can be used to characterize pair-wise interactions that occur during association or dissociation of a larger complex such as the pair-wise interaction between polymerase and template nucleic acid in a complex that forms between the polymerase, template and a monomeric nucleotide. The terms can also characterize a combination or series of interactions such as interactions between polymerase, template nucleic acid and a nucleotide that form a ternary complex. The various interactions that can be characterized by the above kinetic terms will be evident from the description and equations set forth herein.

As used herein, the term "stopped-flow" means delivery of fluid to a detection site using rapid flow of the fluid followed by abrupt stoppage of the flow. The fluid that is delivered typically displaces an equal volume of fluid from the detection site. The fluid can mix with a solid-phase analyte. For example, a fluid containing polymerase molecules and/or nucleotide molecules can mix with a nucleic acid feature of an array, whereby the feature of the array is the detection site. In particular embodiments, two or more fluids can be mixed at a detection site. For example, a first fluid containing polymerase molecules and a second fluid containing nucleotide molecules can be mixed. The two or more fluids can optionally mix with a solid-phase analyte. For example, a first fluid containing polymerase molecules and a second fluid containing nucleotide molecules can be mixed at a detection site that contains a nucleic acid feature of an array. The dead time for stopped-flow fluid delivery can be, for example, less than 2 milliseconds (msec). Accordingly, the dead time can be no longer than 2 msec, 1.5 msec, 1 msec, 0.8 msec, 0.6 msec, 0.5 msec or 0.4 msec. See also Chance, B. J. Frank. Inst., 229, 613 (1940), which is incorporated herein by reference in its entirety.

As used herein, the term "transient state," when used in reference to a polymerase, means the apparent condition or mode of the polymerase with respect to an interaction with another molecule. The interaction can be a binding interaction, a catalytic interaction or an interaction that includes both binding and catalysis. For example, a polymerase can be in a state whereby it is bound to a nucleic acid (e.g. at a feature of an array) or in a state where it is dissociated from a nucleic acid (e.g. at a feature of an array). It will be understood that a polymerase molecule can be dissociated from a nucleic acid feature despite being present in the same volume of solution occupied by the nucleic acid feature. Furthermore, reference to a polymerase being dissociated from a nucleic acid or other molecule does not necessarily imply that the polymerase was ever associated with the nucleic acid. The interaction is typically temporary or reversible and can be determined from a time based measurement. The transient state of a polymerase can be determined, for example, from a kinetic constant (e.g. binding rate constant, dissociation rate constant), an equilibrium constant, a reaction rate measurement, an equilibrium state measurement or the like. A transient state for a polymerase can also be determined as a combination of kinetic constants and therefore need not be defined by a single kinetic constant. The transient state of molecules other than polymerase shall be similarly defined as the apparent condition or mode of those molecules with respect to an interaction with another molecule.

As used herein, the term "transient dynamic," when used in reference to a polymerase (or other molecule), means an apparent change in an interaction of the polymerase (or other molecule) with another molecule. The interaction can be a binding interaction, a catalytic interaction or an interaction that includes both binding and catalysis. For example, the change can be the association of a polymerase with a nucleic acid (e.g. at a feature of an array) or dissociation of a polymerase from a nucleic acid (e.g. at a feature of an array). A transient dynamic of a polymerase can be determined, for example, from a kinetic constant (e.g. binding rate constant, dissociation rate constant), an equilibrium constant, a reaction rate measurement, an equilibrium state measurement or the like. A transient dynamic for a polymerase can be determined as a combination of kinetic constants and therefore need not be defined by a single kinetic constant.

As used herein, the term "correctly incorporate," when used in reference to a nucleotide and a nucleic acid, means that the nucleotide is covalently added to the nucleic acid in a template directed fashion in accordance with Watson-Crick base pairing to a nucleotide site in a template.

As used herein, the term "array" refers to a population of different molecules that are attached to one or more solid-phase substrates such that the different molecules can be differentiated from each other according to their relative location. An array can include different molecules that are each located at different addressable features on a solid-phase substrate. Alternatively, an array can include separate solid-phase substrates each bearing a different molecule, wherein the different probe molecules can be identified according to the locations of the solid-phase substrates on a surface to which the solid-phase substrates are attached or according to the locations of the solid-phase substrates in a liquid such as a fluid stream. The molecules of the array can be nucleic acid primers, nucleic acid probes, nucleic acid templates or nucleic acid enzymes such as polymerases, ligases or exonucleases.

As used herein, the term "feature" means a location in an array where a particular species of molecule is present. A feature can contain only a single molecule or it can contain a population of several molecules of the same species. Features of an array are typically discrete. The discrete features can be contiguous or they can have spaces between each other. The size of the features and/or spacing between the features can vary such that arrays can be high density, medium density or lower density. High density arrays are characterized as having sites separated by less than about 15 μm. Medium density arrays have sites separated by about 15 to 30 μm, while low density arrays have sites separated by greater than 30 μm. An array useful herein can have, for example, sites that are separated by less than 100 μm, 50 μm, 10 μm, 5 μm, 1 μm, or 0.5 μm. An apparatus or method of the present disclosure can be used to detect an array at a resolution sufficient to distinguish sites at the above densities or density ranges.

As used herein, the term "species" is used to identify molecules according to their chemical structure. Two molecules that are the same species will have the same chemical structure and two molecules that are different species will have different chemical structures. For example, a mixture of nucleotides can include several dCTP molecules. The dCTP molecules will be understood to be the same species as each other. Similarly, individual DNA molecules that have the same sequence of nucleotides are the same species.

As used herein, the term "nucleic acid" can be used refer to at least two nucleotide monomers linked together. A nucleic acid can contain phosphodiester bonds, however, in some embodiments, a nucleic acid can be an analog having other types of backbones, comprising, for example, phosphoramide, phosphorothioate, phosphorodithioate, peptide nucleic acid backbones and linkages, positive backbones, or non-ionic backbones. A nucleic acid can include a pentose moiety such as ribose (present in naturally occurring RNA), deoxyribose (present in naturally occurring DNA) or dideoxy ribose. In some embodiments a nucleic acid can have a non-pentose moiety or carbocyclic sugar instead of a ribose or deoxyribose moiety. A nucleic acid can have one or more different base moieties including, but not limited to, adenine (A), guanine (G), thymine (T), uracil (U), cytosine (C), inosine, xanthanine, hypoxanthanine, isocytosine, isoguanine, nitropyrrole (including 3-nitropyrrole) and/or nitroindole (including 5-nitroindole). Nucleic acids may be single stranded or double stranded, as specified, or contain portions of both double stranded and single stranded sequence. The nucleic acid may be DNA (e.g. genomic DNA or cDNA), RNA or a hybrid.

As used herein, the term "nucleotide" is intended to include natural nucleotides, non-natural nucleotides, ribonucleotides, deoxyribonucleotides, dideoxyribonucleotides and other molecules known as nucleotides. The term can be used to refer to a monomer unit that is present in a polymer, for example to identify a subunit present in a DNA or RNA strand. The term can also be used to refer to a molecule that is not necessarily present in a polymer, for example, a monomeric molecule that is capable of being incorporated into a polynucleotide in a template dependent manner by a polymerase. A nucleotide analog can have a base moiety including, but not limited to, adenine (A), guanine (G), thymine (T), uracil (U), cytosine (C), inosine, xanthanine, hypoxanthanine, isocytosine, isoguanine, nitropyrrole (including 3-nitropyrrole) and/or nitroindole (including 5-nitroindole). Exemplary natural nucleotides include, without limitation, ATP, UTP, CTP, GTP, ADP, UDP, CDP, GDP, AMP, UMP, CMP, GMP, dATP, dTTP, dCTP, dGTP, dADP, dTDP, dCDP, dGDP, dAMP, dTMP, dCMP, and dGMP.

Non-natural nucleotides include those that are not present in a natural biological system. A non-natural nucleotide can be incapable of being further extended after being incorporated into a polynucleotide. Examples include, nucleotides having a reversible or non reversible blocking moiety. In some embodiments, a nucleotide will not include a reversible blocking moiety, or a nucleotide will not include a non-reversible blocking moiety or a nucleotide will not include any blocking moiety at all. A natural or non-natural nucleotide can be capable of being further extended after being incorporated into a polynucleotide. Examples include, nucleotides having a 3' hydroxyl.

As used herein, the term "blocking moiety" when used in reference to a nucleotide, means a part of the nucleotide that inhibits or prevents the nucleotide from forming a covalent linkage to a second nucleotide. For example, in the case of nucleotides having a pentose moiety, a blocking moiety can prevent formation of a phosphodiester bond between the 3' oxygen of the nucleotide and the 5' phosphate of the second nucleotide. The blocking moiety can be part of a nucleotide that is a monomer unit present in a nucleic acid polymer or the blocking moiety can be a part of a free nucleotide (e.g. a nucleotide triphosphate). The blocking moiety that is part of a nucleotide can be reversible, such that the blocking moiety can be modified to render the nucleotide capable of forming a covalent linkage to a second nucleotide. In particular embodiments, a blocking moiety, such as a reversible blocking moiety, can be attached to the 3' position or 2' position of a pentose moiety of a nucleotide analog.

As used herein, the term "label" means a molecule or moiety thereof that provides a distinguishable characteristic. The distinguishable characteristic can be, for example, an optical signal such as absorbance of radiation, fluorescence emission, luminescence emission, fluorescence lifetime, fluorescence polarization, or the like; Rayleigh and/or Mie scattering; binding affinity for a ligand or receptor; magnetic properties; electrical properties; charge; mass; radioactivity or the like. Exemplary labels include, without limitation, a fluorophore, luminophore, chromophore, nanoparticle (e.g., gold, silver, carbon nanotubes), heavy atoms, radioactive isotope, mass label, charge label, spin label, receptor, ligand, or the like. The label can be part of a nucleotide that is a monomer unit present in a nucleic acid polymer or the label moiety can be a part of a free nucleotide (e.g. a nucleotide triphosphate).

The present disclosure provides a method of distinguishing nucleotide sequences for different nucleic acid molecules. The method can include the steps of (a) mixing a plurality of different nucleic acid molecules with polymerase molecules and nucleotide molecules, wherein the different nucleic acid molecules are attached to a surface in the form of an array of nucleic acid features; (b) determining a transient state of the polymerase molecules at the nucleic acid features; and (c) identifying a subset of nucleic acid features that correctly incorporate the nucleotide molecules based on the transient state of the polymerase molecules at the nucleic acid features, thereby distinguishing the nucleotide sequences for the different nucleic acid molecules. Alternatively or additionally, the method can determine a transient dynamic of the polymerase molecules at the nucleic acid features at step (b).

In particular embodiments, a method set forth in this disclosure can monitor the interactions of a polymerase molecule with a target nucleic acid in a pre-equilibrium time frame. Taking as an example the method set forth immediately above, step (b) can involve monitoring binding of the polymerase molecules to the nucleic acid features at several points during a pre-equilibrium time period, thereby determining transient state (or transient dynamic) of the polymerase molecules at the nucleic acid features. Pre-equilibrium detection of molecules (also known as pre-steady state detection) can utilize pre-equilibrium kinetic techniques. Pre-equilibrium kinetics provides a measure or characterization of the formation and consumption of receptor-ligand intermediates (e.g. polymerase-nucleic acid intermediates) before binding equilibrium is reached. The methods can also be used to measure or characterize a catalytic reaction that occurs subsequent to binding. The methods, also known as burst kinetics, can provide a useful characterization of the first few milliseconds of a binding and/or catalytic reaction. In the pre-equilibrium time frame, an intermediate state can form relatively rapidly (e.g. formation of a bound complex between polymerase, nucleic acid and nucleotide). The apparent rate of complex formation then slows as steady state is reached. The initial burst phase of the reaction between polymerase, nucleic acid and nucleotide is assumed to measure a single turnover of each free species and is not necessarily observed as it is typically complete before the free species are completely mixed.

Nevertheless, pre-equilibrium detection is possible using practical methods and apparatus as set forth herein. For example, pre-equilibrium kinetics can be determined using stopped-flow techniques. Using these techniques small volumes of solutions can be rapidly driven from syringes into a high efficiency mixer to initiate a fast reaction. The resultant reaction volume then displaces the contents of a detection site (e.g. one or more features of an array) thus filling it with freshly mixed reagents. The volume injected is limited by the stop syringe which provides the 'stopped-flow.' Just prior to stopping, a steady state flow is achieved. The solution entering the reaction site is typically only milliseconds old. The age of this reaction volume is also known as the 'dead time' of the stopped-flow system. As the solution fills the stopping syringe, the plunger hits a block, causing the flow to be stopped instantaneously. Using appropriate techniques, the pre-steady state kinetics of the reaction can be measured at the detection site. For example, stopped-flow techniques can be combined with photometric readout such as absorption and fluorescence as described, for example, in Kuchta, et al., *Biochemistry* 26, 8410-8417 (1987), or Johnson, *The Enzymes*, XX, 1-61 (1992), each of which is incorporated herein by reference in its entirety.

As set forth herein, stopped-flow techniques can be used to monitor the pre-steady kinetics of polymerase binding to a nucleic acid template in the presence of nucleotides that are correctly matched to the nucleic acid template or mismatched with the template. The resulting kinetic measurements and/or characterizations can be used to identify a base that is present at a particular location in the template. Furthermore, sequential detection events, carried out as a primer strand is extended along the template strand, can be used to determine a sequence of nucleotides that is present in the template strand. Systems and methods for fast delivery and rapid mixing of reagents for characterizing nucleic acids using pre-steady state kinetics are provided herein. A description of various embodiments is provided below by way of example and is not intended to be limiting. For purposes of demonstration and explanation, aspects of various methods are provided in the context of various systems and vice versa. However, the methods of the invention do not necessarily need to be carried out on the exemplified systems, nor do the systems of the invention necessarily need to be used to carry out the exemplified methods.

A mixing process, whether carried out using a stopped-flow technique or other technique, can involve delivery of a fluid having at least a first component to a detection site having at least a second component, whereby the two components mix at the detection site. Exemplary components include those that participate in a nucleic acid extension reaction such as polymerase, nucleic acid (typically having a template strand and a primer strand), nucleotide and various other components known to those skilled in the art for facilitating nucleic acid extension. One or more of these different components can be present at the detection site such that mixing occurs when at least one of the other components is delivered. For example, nucleic acid can be present at the site and mixing can occur when polymerase and nucleotide are delivered. Alternatively, nucleic acid and nucleotide can be present at the site and mixing can occur when polymerase is delivered. In another alternative, nucleic acid and polymerase can be present at the site and mixing can occur when nucleotide is delivered. Other delivery schemes will be apparent for formats where polymerase and/or nucleotide is/are present at the site.

For ease of explanation, reaction components are referred to above and elsewhere herein in the singular. It will be understood however that unless the context clearly indicates otherwise, those methods and compositions that are described using the singular also encompass the plural. For example, the description above of delivering a polymerase is intended to describe delivery of one or more polymerase molecules.

The component(s) at the reaction site can be in solution or attached to a solid phase surface. For example, the nucleic acid component can be attached to a feature of an array. Thus, mixing can occur between solution-phase component(s) and solid-phase component(s). A reaction component can be attached to an array in a way that provides detection at a single molecule level or at an ensemble level. Single molecule detection can be achieved with a population of reaction components that is attached to a solid support in a way that signals arising from an individual reaction component can be distinguished from signals arising from all other reaction components on the support. Ensemble level detection can be carried out such that a population of nucleic acids (or other reaction components) is attached at a feature of an array in a way that reactions occurring for several molecules at the feature can be detected. In ensemble-level detection reactions occurring for several species within a feature need not be distinguished from each other, but reactions occurring at different features on the same array can be distinguished from each other.

Whether or not solid-phase components are present at the detection site, mixing can involve the delivery of two or more solutions to the site. For example, nucleic acid can be present at the detection site and mixing can involve the delivery of a first fluid bearing free polymerase and a second fluid bearing free nucleotide. Generally, the two or more fluids are delivered to the site simultaneously to allow mixing to occur. However, if desired, two or more fluids can be delivered sequentially. In the event that several reagents are delivered in separate fluids, the time-frame for detection and/or pre-equilibrium kinetic analysis can be initiated based on the time of delivery for the last added fluid.

The kinetics of binding (e.g. formation of a ternary complex between polymerase, nucleic acid and nucleotide) and catalysis (e.g. primer extension by polymerase) can be directly correlated to the flow rates, volumes of fluids being delivered to a reaction site and the time of mixing at the reaction site. Fast mixing rates, which can be achieved via active or passive mixing coupled with higher flow rates, can maximize homopolymer discrimination.

Rapid mixing is desirable for many embodiments as this improves observation and characterization of kinetics for polymerase binding and catalysis. For example mixing times of at least 0.1 msec, 0.5 msec, 1 msec, 10 msec, 100 msec, 1 sec or 10 sec can be used. For formats where an ensemble of nucleic acid templates is observed, complications that may otherwise arise due to diffusion within the ensemble can be avoided or reduced to acceptable levels by use of rapid mixing at a detection site that has a high density of the templates. For example, in an array format a high density of nucleic acid templates can be attached at each feature. As such, each feature can effectively mimic a confined stopped flow reaction volume for the ensemble of attached templates. The number of nucleic acid templates that are spatially confined to an individual feature in an ensemble format can be scaled from a few templates per square micron to many thousands of templates per square micron. A straightforward titration analysis can be used to identify a desirable density to suit a particular application. In some embodiments, a plurality of nucleic acid molecules is present at an individual feature and each molecule contains an individual template. Examples of such arrays are those produced by solid-phase amplification methods such as the clustering methods (also known as bridge amplification) or emulsion PCR methods set forth herein below. For embodiments where individual nucleic acid molecules each contain individual templates, the spacing between the surface attachment points for the molecules can be, for example, at most about 500 nm, 100 nm, 50 nm, 10 nm, 5 nm, 1 nm or lower. Template spacing in solid-phase amplification methods can be controlled, for example, by varying the surface concentration of primers used for capture and/or amplification of the templates (e.g. varying the concentration of primers on a flow cell used for bridge amplification or varying the concentration of primers on beads used for emulsion PCR). More specifically, surfaces having higher template densities can be obtained by grafting the surfaces with higher concentrations of the primers, thereby decreasing the spacing between templates.

Embodiments are also provided where a plurality of templates are present on a single nucleic acid molecule. For example, a concatameric amplicon that is produced by a rolling circle amplification method can include several copies of a particular template. Rolling circle amplification (RCA) can be carried out as described, for example in Lizardi et al., Nat. Genet. 19:225-232 (1998) or US 2007/0099208 A1, each of which is incorporated herein by reference in its entirety. A nucleic acid molecule that has several template copies, whether produced by RCA or another method, can be attached to a surface. The surface can be for example, a feature of an array and the feature can contain one or more of the nucleic acid molecules that have several template copies.

Any of a variety of polymerases can be used in a method or composition set forth herein including, for example, protein-based enzymes isolated from biological systems and functional variants thereof. Generally, polymerases that display a relatively large difference between the $k_{-1}$ (or $k_{off}$) for a correct nucleotide and mismatched nucleotides (with respect to Watson-Crick base pairing to a template) are desirable. When using ensemble level detection, good base discrimination can be achieved by maximizing the diffusion rate, $k_{-1}$ and $k_1$ (or $k_{on}$). Examples of desirable polymerases are family A polymerases, such as Klenow fragment of E. coli DNA polymerase I, family B polymerases, such as apo protein of T4 & Rb69 polymerases, and family X polymerases such as pol beta since these polymerases demonstrate relatively poor processivity (i.e. small $k_{-1}$). Reduction in processivity can also be achieved through manipulation of sequencing conditions such as buffer conditions, ionic strength, mixed metal ions, elevated reaction temperatures, crowding reagents (e.g. polyethylene glycol), detergents and/or pH.

Reference to a particular polymerase will be understood to include functional variants thereof unless indicated otherwise. A particularly useful function of a polymerase is the ability to bind to a nucleic acid and nucleotide to form a complex and the ability to catalyze the extension of the nucleic acid strand by addition of the nucleotide. Other polymerase functions that are useful are described elsewhere herein. Examples of useful polymerases include DNA polymerases and RNA polymerases. Exemplary DNA polymerases include those that have been classified by structural homology into families identified as A, B, C, D, X, Y, and RT. DNA Polymerases in Family A include, for example, T3, T5 or T7 DNA polymerases, eukaryotic mitochondrial DNA Polymerase γ, *E. coli* DNA Pol I, *Thermus aquaticus* Pol I, *Bacillus subtilis* Pol I and *Bacillus stearothermophilus* Pol I. DNA Polymerases in Family B include, for example, eukaryotic DNA polymerases α, δ, and ε; DNA polymerase ζ; T4 DNA polymerase, Phi29 DNA polymerase, and RB69 bacteriophage DNA polymerase. Family C includes, for example, the *E. coli* DNA Polymerase III alpha subunit. Family D includes, for example, polymerases derived from the Euryarchaeota subdomain of Archaea. DNA Polymerases in Family X include, for example, eukaryotic polymerases Pol β, pol σ, Pol λ, and Pol μ, and *S. cerevisiae* Pol4. DNA Polymerases in Family Y include, for example, Pol η, Pol iota, Pol kappa, *E. coli* Pol IV (DINB) and *E. coli* Pol V (UmuD'2C). The RT (reverse transcriptase) family of DNA polymerases includes, for example, retrovirus reverse transcriptases and eukaryotic telomerases. Exemplary RNA polymerases include, but are not limited to, viral RNA polymerases such as T7 RNA polymerase; Eukaryotic RNA polymerases such as RNA polymerase I, RNA polymerase II, RNA polymerase III, RNA polymerase IV, and RNA polymerase V; and Archaea RNA polymerase.

The above classifications are provided for illustrative purposes. It will be understood that variations in the classification system are possible. For example, in at least one classification system, Family C polymerases have been categorized as a subcategory of Family X. Furthermore, polymerases can be classified according to other characteristics, whether functional or structural, that may or may not overlap with the structural characteristics exemplified above. Some exemplary characteristics are set forth in further detail below.

A polymerase having an intrinsic 3'-5' proofreading exonuclease activity can be useful for some embodiments. Polymerases that substantially lack 3'-5' proofreading exonuclease activity are also useful in some embodiments, for example, in most sequencing embodiments. Absence of exonuclease activity can be a wild type characteristic or a characteristic imparted by a variant or engineered polymerase structure. For example, exo minus Klenow fragment is a mutated version of Klenow fragment that lacks 3'-5' proofreading exonuclease activity. Klenow fragment and its exo minus variant can be useful in a method or composition set forth herein. Polymerases can also catalyze pyrophosphorolysis, the direct reversal of polymerization in the same active site. This activity can be useful for various embodiments that are set forth herein.

Polymerases can be characterized according to their processivity. A polymerase can have an average processivity that is at least about 50 nucleotides, 100 nucleotides, 1,000 nucleotides, 10,000 nucleotides, 100,000 nucleotides or more. Alternatively or additionally, the average processivity for a polymerase used as set forth herein can be, for example, at most 1 million nucleotides, 100,000 nucleotides, 10,000 nucleotides, 1,000 nucleotides, 100 nucleotides or 50 nucleotides. Polymerases can also be characterized according to their rate of processivity or nucleotide incorporation. For example, many native polymerases can incorporate nucleotides at a rate of at least 1,000 nucleotides per second. In some embodiments a slower rate may be desired. For example, an appropriate polymerase and reaction conditions can be used to achieve an average rate of at most 500 nucleotides per second, 100 nucleotides per second, 10 nucleotides per second, 1 nucleotide per second, 1 nucleotide per 10 seconds, 1 nucleotide per minute or slower. It will be understood that polymerases from any of a variety of sources can be modified to increase or decrease their average processivity or their average rate of processivity (e.g. average rate of nucleotide incorporation) or both. Accordingly, a desired reaction rate can be achieved using appropriate polymerase(s), nucleotide analog(s), nucleic acid template(s) and other reaction conditions.

A polymerase can be either thermophilic or heat inactivatable (e.g. at a temperature that falls in the range of 40° C. to 90° C. Thermophilic polymerases are typically useful for high temperature conditions or in thermocycling conditions such as those employed for polymerase chain reaction (PCR) techniques. Examples of thermophilic polymerases include, but are not limited to 9°N DNA Polymerase, Taq DNA polymerase, Phusion® DNA polymerase, Pfu DNA polymerase, RB69 DNA polymerase, KOD DNA polymerase, and VentR® DNA polymerase. Most polymerases isolated from non-thermophilic organisms are heat inactivatable. Examples are DNA polymerases from phage. Polymerases from any of a variety of sources can be modified to increase or decrease their tolerance to high temperature conditions for use in a method or composition set forth herein.

Polymerases can be characterized according to their fidelity. Fidelity generally refers to the accuracy with which a polymerase incorporates correct nucleotides into a copy of a nucleic acid template. DNA polymerase fidelity can be measured as the ratio of correct to incorrect nucleotide incorporations when the nucleotides are present at equal concentrations to compete for primer extension at the same site in the polymerase-primer-template DNA binary complex. As proposed by Fersht, DNA polymerase fidelity can be calculated as the ratio of $(k_{cat}/K_m)$ for the correct nucleotide and $(k_{cat}/K_m)$ for the incorrect nucleotide; where $k_{cat}$ and $K_m$ are the familiar Michaelis-Menten parameters in steady state enzyme kinetics (Fersht, A. R. (1985) *Enzyme Structure and Mechanism,* 2nd ed., p 350, W. H. Freeman & Co., New York., which is incorporated herein by reference in its entirety). Alternatively, in pre-equilibrium measurements, the ratio of $(k_{pol}/K_d)$ for the correct and incorrect nucleotides can be used. In particular embodiments, a polymerase can have a fidelity value at least 100, 1000, 10,000, 100,000, or 1 million, with or without a proofreading activity.

A polymerase that is used in a method or composition herein can include a label. Fluorophores are particularly useful for labeling polymerases, but can be used for other reaction components set forth herein as well. Exemplary fluorophores include, but are not limited to, fluorescent nanocrystals; quantum dots; d-Rhodamine acceptor dyes including dichloro[R110], dichloro[R6G], dichloro [TAMRA], dichloro[ROX] or the like; fluorescein donor dye including fluorescein, 6-FAM, or the like; Cyanine dyes such as Cy3B; Alexa dyes, SETA dyes, Atto dyes such as atto 647N which forms a FRET pair with Cy3B and the like. Fluorescent probes and methods for their use including attachment to polymerases and other molecules are described in *Molecular Probes: The Handbook* (Invitrogen, Carlsbad Calif.), which is incorporated herein by reference in its entirety. A fluorophore or other probe that is used in a method or composition set forth herein can be an intrinsic probe that is present in a naturally occurring molecule being detected, such as a tryptophan residue in a polymerase. Alternatively or additionally, one can use a probe that is exogenous to a polymerase or other molecule being detected. Thus, in some embodiments solely exogenous probes are detected such that endogenous probes are not detected, in other embodiments solely endogenous probes are detected such that exogenous probes are not detected and in some embodiments a combination of exogenous and endogenous probes are detected.

In particular embodiments, a green fluorescent (GFP) protein can be attached to a polymerase. GFP can be attached via a chemical linkage, or in many cases more conveniently via a protein fusion. Protein fusions have a polypeptide linkage between a GFP domain and polymerase domain formed by expression from a genetic construct where the coding sequences of the two domains are fused. Variants of GFP such as wavelength shifted variants can be used similarly. Techniques for making and using GFP and variants thereof are described throughout Chemical Society Reviews volume 38, issue 10 (2009), which is incorporated herein by reference in its entirety.

A label can be attached to a polymerase or other reaction component, for example, via covalent linkage. In a particular embodiment, a probe can be attached site specifically to a polymerase by introducing cysteine residue at a desired location in the polymerase and then modifying the polymerase with a probe having a moiety that reacts specifically with the sulfur group of cysteine, an exemplary reactive moiety being a reactive maleimide moiety. An exemplary method for introducing probes into a polymerase using site specific cysteine mutagenesis followed by chemical modification with dyes having maleimide moieties is described in Santoso et al. *Proc. Nat'l. Acad. Sci. USA* 107:705-710 (2010), which is incorporated herein by reference in its entirety. Probes can also be introduced to polymerase by split inteins as described in Yang et al. *J. Am. Chem. Soc.*, 131:11644-11645 (2009), which is incorporated herein by reference in its entirety. Probes can also be introduced to a polymerase by genetically encoded unnatural amino acids. One example is described in Fleissner et al. *Proc. Nat'l. Acad. Sci. USA* 106:21637-42 (2009), which is incorporated herein by reference in its entirety.

Labels other than fluorescent labels can be used. For example, a polymerase or other reaction component can be labeled by paramagnetic spin labels such as nitroxide, and detected by electron paramagnetic resonance and related techniques. Exemplary spin labels and techniques for their detection are described in Hubbell et al. *Trends Biochem Sci.* 27:288-95 (2002), which is incorporated herein by reference in its entirety. Gold nanoparticles with thiol reactive groups can also be used to label proteins, for example as described in Gregori et al. *J. Biol. Chem.* 272:58-62 (1997), which is incorporated herein by reference in its entirety.

Electrical based detection can be used. Electrical detection is particularly useful for a field use (e.g. hand held) sequencing device. Electrical detection is advantageous because it does not require light sources, optics and protein labels. Field effect transistors (FET), a class of biosensors, can be used for electrical detection, for example as described in Schoning and Poghossian, *Analyst,* 127: 1137-1151 (2002), which is incorporated herein by reference in its entirety. FET biosensors respond to change in local charge distribution. Ion sensitive field effect transistors (ISFETs) are a type of FET that can be used, for example, as described in Bergveld, *IEEE Trans. Biomed. Eng.,* 17,70-71 (1970), which is incorporated herein by reference in its entirety. ISFETs are especially optimized for pH sensing; thus, they are ideal sensors for monitoring enzymatic reactions that generate protons as a product. Changes in intrinsic surface charge lead to a change in the local charge distribution that can be detected, for example, as described in Schenck, *Theory, Design and Biomedical Applications of Solid State Chemical Sensors*, ed. P. W. Cheung, CRC Press, Boca Raton, 1978, pp. 165-173, which is incorporated herein by reference in its entirety. FETs have been advanced with silicon nanowire (SiNW) and carbon nanotube (CNT) devices and can be used for electrical detection as described in Cui et al., *Science,* 293: 1289-1292(2001), which is incorporated herein by reference in its entirety. Femtomolar sensitivity with SiNW FETs can be accomplished by detecting in the frequency domain instead of the time domain as described by Zheng et al., *NanoLett.* 10(80):3179-3183, which is incorporated herein by reference in its entirety. Single molecule sensitivity can be achieved on CNT with microsecond resolution as described by Sorgenfrie et al. *Nat. Nano.,* 6:126-132 (2011), which is incorporated herein by reference in its entirety.

Figure 3:
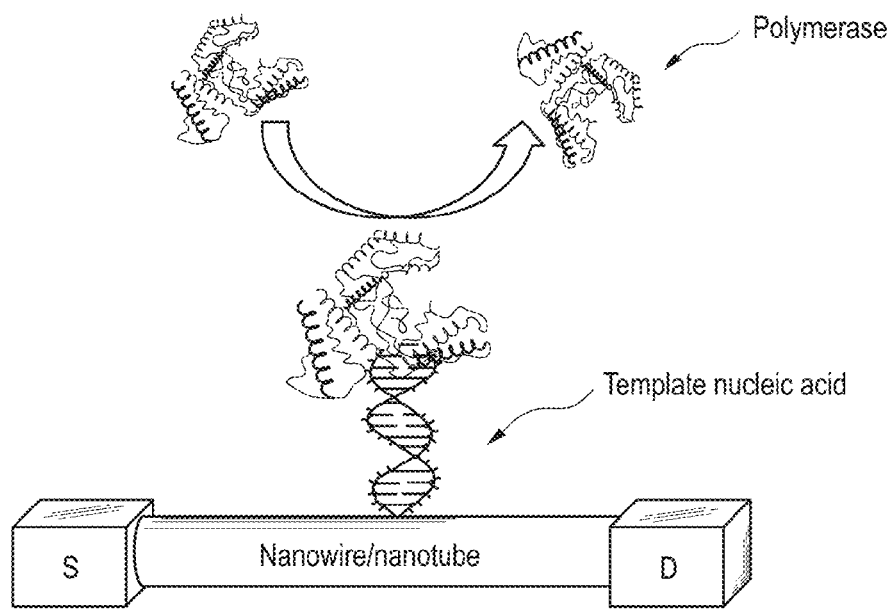
FIG. 3 shows an extendable duplex nucleic acid attached covalently to Si nanowire or a carbon nanotube field effect transistor. S and D are the source and drain, respectively. The conductance of the SiNW or CNT are modulated according to the transient state of the polymerase with respect to interactions with the nucleic acid.
Figure 4:
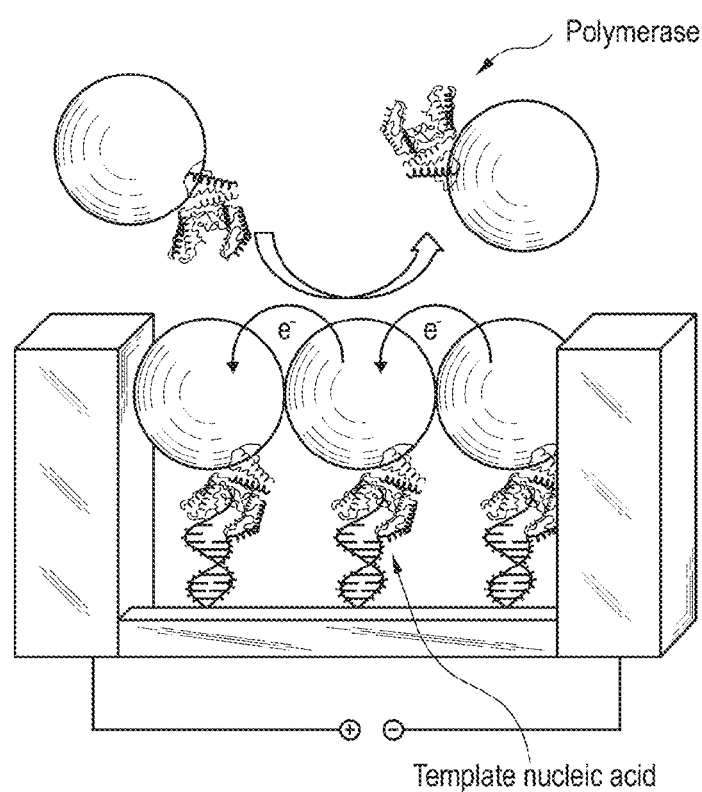
FIG. 4 shows a detection scheme exploiting electron transport through gold particles. A nucleic acid molecule is attached between electrodes. Covalent attachment of a polymerase to gold nanoparticles allows a detectable event of electron transport between electrodes upon polymerase binding.

In one embodiment DNA can be covalently attached to SiNW and CNTs for FET based detection of the transient polymerase kinetics (See FIG. 3). A second method of electrical detection can exploit electron transport through gold nanoparticles. Direct electron transport through gold nanoparticles can be readily measured, for example, as described in Nakanishi et al., *Nat. Nano.* 6:740-746(2011), which is incorporated herein by reference in its entirety. In one embodiment, DNA can be immobilized between two electrodes as shown in FIG. 4. Electron transport will occur during the polymerase transient binding events. The polymerase will be conjugated to gold nanoparticles; thus, the amount of current will correspond to the transient polymerase binding kinetics.

Label-free sensing can also be used in a method set forth herein. Examples include, but are not limited to, sensing techniques related to a change in the environment and/or the size of a nucleic acid feature (whether an ensemble feature or single molecule feature) upon binding of polymerase.

Any of a variety of nucleotide species can be useful in a method or composition set forth herein. For example, naturally occurring nucleotides can be used such as ATP, UTP, CTP, GTP, ADP, UDP, CDP, GDP, AMP, UMP, CMP, GMP, dATP, dTTP, dCTP, dGTP, dADP, dTDP, dCDP, dGDP, dAMP, dTMP, dCMP, and dGMP. Typically, dNTP nucleotides are incorporated into a DNA strand by DNA polymerases and NTP nucleotides are incorporated into an RNA strand by RNA polymerases. In particular embodiments, NTP nucleotides or analogs thereof can be incorporated into DNA by a DNA polymerase, for example, in cases where the NTP, or analog thereof, is capable of being incorporated into the DNA by the DNA polymerase and where the transient state (or the transient dynamic) of the DNA polymerase on the DNA in the presence of an NTP that properly base pairs with the DNA can be distinguished from the transient state (or the transient dynamic) of the polymerase in the presence of a mismatched nucleotide. Alternatively, dNTP nucleotides or analogs thereof can be incorporated into RNA by an RNA polymerase, for example, in cases where the dNTP, or analog thereof, is capable of being incorporated into the RNA by the RNA polymerase and where the transient state (or the transient dynamic) for the RNA polymerase in the presence of a correctly matched dNTP can be distinguished from the transient state (or the transient dynamic) of the RNA polymerase in the presence of a mismatched nucleotide.

Non-natural nucleotide analogs are also useful. Particularly useful non-natural nucleotide analogs include, but are not limited to, those for which polymerase displays a transient state (or a transient dynamic) that is distinguishable with respect to correctly matched and mismatched base moieties. For example, a non-natural nucleotide analog having a base moiety that correctly base pairs with a template strand may usefully produce a detectably different transient state (or transient dynamic) for a polymerase compared to the transient state (or the transient dynamic) for the polymerase in the presence of a nucleotide analog having a base moiety that does not correctly match with the template.

Non-natural nucleotide analogs having 5' modifications are particularly useful. The non-natural nucleotide analog will typically have a triphosphate but can have more or fewer phosphates as set forth elsewhere herein. In particular embodiments, one or more of the alpha phosphate, beta phosphate or gamma phosphate of a non-natural nucleotide is covalently attached to a moiety other than oxygen. A moiety that is attached to a phosphate or otherwise present at the 5' position can provide a negative charge, a positive charge, metal-chelating activity or steric bulk. Exemplary moieties include, but are not limited to, amino acids, in the L-enantiomer form or R-enantiomer form, such as histidine, aspartate, glutamate, tryptophan, phenylalanine, methionine, tyrosine, cysteine, glycine alanine, or proline; an amino group; a chelated metal such as magnesium or manganese; a methyl group; a halogen such as bromine, chlorine or iodine; a thiol group; an electron withdrawing group; an electron donating group; an aromatic amine; or an aliphatic amine. These and other moieties may be advantageous in embodiments where they provide an interaction with a polymerase, or other nucleic acid enzyme, that differs from the interaction that the enzyme has with a nucleotide lacking the moiety. As such, the presence and absence of the moiety on respective nucleotide species can be exploited to distinguish the nucleotide species in a sequencing method, for example, based on the transient state (or the transient dynamic) of the polymerase with respect to interactions with a template nucleic acid in the presence of the nucleotide species.

It will be understood that the 3' position of a nucleotide can have a blocking moiety (such as a reversible blocking moiety) or other moiety. Examples of reversible blocking moieties that can be used and their respective deblocking agents are described, for example, in U.S. Pat. Nos. 7,427,673; 7,414,116; 7,057,026 and 8,241,573; and PCT publications WO 91/06678 and WO 07/123744, each of which is incorporated herein by reference in its entirety. For methods that use reversibly blocked nucleotides, deblocking and washing steps can be carried out between nucleotide addition steps. Typically a chemically reactive deblocking moiety is used; however a photo-sensitive block can be used for fast deblocking by light. It will be understood that in some embodiments a nucleotide analog having a 3' blocking moiety or lacking a 3' hydroxyl (such as a dideoxynucleotide analog) can be used under conditions where the primer strand that has incorporated the nucleotide analog is not further extended. In some embodiments, the nucleotide(s) will not include a reversible blocking moiety, or the nucleotides(s) will not include a non-reversible blocking moiety or the nucleotide(s) will not include any blocking moiety at all.

Another useful type of nucleotide is a caged nucleotide. An exemplary caged nucleotide has a moiety with a photo-isomerizable double bond. In particular embodiments, a first isomer of the caged nucleotide causes a polymerase to have a different transient state (or transient dynamic) for a nucleic acid template than occurs in the presence of a second isomer of the caged nucleotide. For example, a polymerase may readily bind to a template nucleic acid in the presence of the first isomer under particular conditions whereas the polymerase will not appreciably bind to the nucleic acid template in the presence of the second isomer under the particular conditions. Azobenzene is a moiety that undergoes photo-isomerization whereby UV radiation causes trans to cis conversion and blue light causes cis to trans conversion. Other moieties that undergo photo-isomerization and conditions for their photo-isomerization are known in the art and include, for example, stilbene, and cinnamic acid.

A further example of a caged nucleotide is one having a moiety that is photo-cleavable. In some embodiments, the presence of the moiety on the nucleotide alters (e.g. reduces or increases) the rate of binding or catalysis of a polymerase for a nucleic acid template compared to the nucleotide without the moiety. For example, a polymerase may readily bind to a nucleic acid template in the presence of a nucleotide lacking the moiety under particular conditions whereas the presence of the moiety will retard or prevent the polymerase from binding to the nucleic acid under the particular conditions. Exemplary photo-cleavable moieties include, but are not limited to (1-(4,5-dimethoxy-2-nitrophenyl)ethyl)ester (i.e. DMNPE) and (1-(2-nitrophenyl)ethyl)ester (i.e. NPE). See *Meth. Enzymol.* 291:307-347 (1998), which is incorporated herein by reference in its entirety.

A photo-isomerizable moiety or photo-cleavable moiety can be attached to a nucleotide at any of a variety of locations in the nucleotide including, but not limited to, the ribose moiety, a phosphate moiety, or a base moiety or other specific locations exemplified herein in the context of other nucleotide analogs. Furthermore, a photo-isomerizable moiety or photo-cleavable moiety can be attached to one or more nucleotide species used in a method or reaction set forth herein. For example, such moieties can be present on a nucleotide analog having a base moiety that pairs with adenine, thymine, guanine or cytosine. Mixtures of nucleotides can be used that have different photo-isomerizable or photo-cleavable moieties. Such a mixture can further include one or more nucleotides having no photo-reactive moiety. The different moieties can be tuned for photoreactions with different wavelengths of light. As such, individual nucleotide species can be activated (or deactivated) using different wavelengths of light in order to provide light-gated control of individual nucleotide species in a reaction such as a sequencing reaction set forth herein.

Use of one or more caged nucleotide species can provide a means to initiate, modulate or attenuate a reaction set forth herein. For example, one or more photo-isomerizable or photo-cleavable nucleotide species can be introduced to a reaction in an inactive conformation and subsequently light activation can be used to initiate binding of nucleotides to a polymerase or addition of the nucleotides to a nucleic acid by a polymerase. Thus, light activation can provide temporal control of the start point for a reaction set forth herein. Alternatively or additionally, photo-isomerizable nucleotides that are in an active conformation can be inactivated by light to pause or stop a polymerization reaction. Stopping a reaction can be achieved by separating reaction components from each other, for example by washing the nucleotides away from a solid-phase attached nucleic acid. Such a separation step need not be carried out and instead the reaction can be resumed by toggling the photo-isomerizable nucleotide to an active form to resume polymerization. As such, caged nucleotides provide a means to achieve light-gated control of a variety of reactions such as the sequencing methods set forth herein.

Light-gating is particularly useful for embodiments that use real-time detection at a single molecule level. Single molecule reactions are stochastic by nature. Light-gating provides for temporal control of detection to coincide with initiation of the single molecule reaction thereby providing more accurate detection.

Although an advantage of light-gating is set forth above in regard to real-time detection at a single molecule level, it will be understood that light gating is also useful for ensemble-level detection. For example, whether used for a single-molecule or ensemble level embodiments, light gating can provide spatial or temporal control of a reaction. More specifically, a sample can contain a relatively large pool of nucleotides and focused light can be delivered to a portion of a sample to activate a sub-population of the nucleotides. Thus, repeated activation of a subpopulation of nucleotides can be used instead of repeated fluidic delivery steps.

Variants of polymerase can be engineered to bind to and/or catalytically react with natural or non-natural nucleotides at an appropriate or otherwise desired speed to allow detection of differences in polymerase interactions with nucleic acid when different nucleotides are used.

In some embodiments, a reaction composition or method can include nucleotide species that base-pair with no more than one nucleotide species in a nucleic acid template. For example, a method can be carried out under conditions wherein different nucleotide species are contacted with a polymerase and nucleic acid in separate, sequential reactions. Specifically, a nucleotide species that base-pairs with only A can be added in a first reaction, a nucleotide species that base-pairs with only C can be added in a second reaction, a nucleotide species that base-pairs with only T can be added in a third reaction, and a nucleotide species that base-pairs with only G can be added in a fourth reaction. The reactions are referred to as first, second, third and fourth merely to illustrate that the reactions are separate but this does not necessarily limit the order by which the different nucleotide species can added in a method set forth herein. Rather, nucleotide species that base-pair with A, C, T or G can be added in any order desired or appropriate for a particular embodiment of the methods. Typically in a sequencing method, one or more nucleotide species that base-pair with four different nucleotide species in a given template nucleic acid are added sequentially to complete a cycle of the sequencing method. However, it will be understood that fewer than four nucleotide additions can be used in some embodiments. Furthermore, it will be understood that mixtures of nucleotides that base-pair with more than one but no more than 2, 3 or 4 nucleotide species in the nucleic acid template(s) of a sample can be used. Similarly, mixtures of nucleotides that base-pair with more than two but no more than 3 or 4 nucleotide species in the nucleic acid template(s) of a sample can be used. If desired, mixtures of nucleotides that base-pair with more than three but no more than 4 nucleotide species in the nucleic acid template(s) of a sample can be used.

One or more of the reaction components that are used in a method set forth herein can include a label. For example, as set forth previously herein, a polymerase can include a label and the label can be detected during a binding or other reaction. The labels and associated detection methods set forth previously herein in regard to polymerases can be used for other reaction components, for example, as set forth below. In some embodiments, a nucleotide that is used in a binding or other reaction can contain a label that is detected during the reaction. Similarly, a label can be present on a nucleic acid template that binds to a polymerase. It is also useful in some cases to include a label on two or more of the components of a particular reaction. For example, labels can be present on both a nucleotide and a polymerase that participate in a binding or other reaction. Either or both of the labels can be detected to determine transient state (or transient dynamic) of the polymerase with respect to binding or catalytic interactions with a nucleic acid template. Labels can be used that interact with each other to give a characteristic signal when polymerase is bound to a nucleic acid (e.g. a nucleic acid template present at a feature of an array). For example, the labels can provide a donor and acceptor pair for a FRET interaction or a fluorophore and quencher pair. Thus, detection of a binding or other reaction can include detection of an interaction between labels that are present on different components of the reaction.

In particular embodiments, a method set forth herein can be carried out under conditions wherein one or more of the nucleotides lack detectable labels. A method can be carried out under conditions wherein all of the nucleotides lack detectable labels. For example, the nucleotide(s) can lack an exogenous label. Exogenous labels include any labels that are not present in the structure of a natural nucleotide including, for example, an optical label such as a fluorophore, optical quencher, or chromophore.

In particular embodiments, a method set forth herein can be carried out under conditions wherein a nucleic acid, whether a template strand or its complement, lacks detectable labels. For example, a nucleic acid can lack an exogenous label, such as those set forth above.

In some embodiments, a method can be carried out under conditions wherein at least one nucleotide is undetectable including, for example, a condition wherein all of the nucleotides are undetectable. Alternatively or additionally, a method can be carried out under conditions wherein a nucleic acid, whether a template strand or its complement, is undetectable. A nucleotide or nucleic acid can be undetectable due to the use of a detection device or detection mode that is incapable of detecting signals produced by the nucleotides or nucleic acids. For example, an optical device can include an optical filter that rejects optical signals in a range produced by the nucleotides and/or nucleic acids. Alternatively or additionally, an optical device can be configured such that it does not substantially excite nucleotides and/or nucleic acids in a way that optically detectable signals are produced. As such the detection method of apparatus can be specific for a label on a polymerase.

A method set forth herein can be carried out in solution or on a solid support. A solution-phase method will be understood to be one where all components that participate in a reaction are in solution, the components including, for example, a nucleic acid, polymerase and nucleotide. A solid-phase reaction is one where one or more of the components occur in or on a solid support. For example, a nucleic acid, polymerase or nucleotide can be in or on a solid support during the course of a solid-phase reaction. A nucleic acid that is attached to the solid support can be a template nucleic acid such as one that is copied by a polymerase, a primer nucleic acid such as one that is extended by a polymerase, or a double stranded nucleic acid such as one that is acted upon by a polymerase.

Any of a variety of solid-support materials can be used in a method or composition set forth herein. Useful materials include, for example, those that are separable from each other such as beads, particles, microspheres, or chromatographic supports; and those that form a continuous material such as a flow cell, microchip or other chip, microscope slide or other planar surface, or the like. Particularly useful supports are those used for microarrays. Useful materials for a microarray or other solid support include, but are not limited to, glass; modified glass; functionalized glass; plastics such as acrylics, polystyrene and copolymers of styrene and other materials, polypropylene, polyethylene, polybutylene, polyurethanes, Teflon, or the like; polysaccharides; nylon; nitrocellulose; resins; silica; silica-based materials such as silicon or modified silicon; carbon; metal; inorganic glass; optical fiber bundles, or any of a variety of other polymers. Useful substrates include those that allow optical detection, for example, by being translucent to energy of a desired detection wavelength and/or do not produce appreciable background fluorescence at a particular detection wavelength.

A reaction component can be attached to a solid support by methods known in the art. In some embodiments, a component such as a nucleic acid can be synthesized on a solid support by sequential addition of nucleotide units directly on the solid support. Methods known in the art for synthesis of a variety of nucleic acids on solid supports can be used including, for example, photolithographic techniques commercialized by Affymetrix (Santa Clara, Calif.) or Nimblegen (acquired by Roche, Basel Switzerland). Alternatively, components can be synthesized or otherwise obtained first, and then covalently attached to a solid support, for example, as used in array printing methods used by Agilent (Santa Clara, Calif.) and Oxford Gene Technologies (Oxford, UK) or BeadArray manufacture (Illumina, San Diego, Calif.). Nucleic acids can also be amplified on a surface using methods such as bridge amplification, rolling circle amplification or emulsion PCR as set forth in further detail elsewhere herein.

Reaction components can be attached to functional groups on a solid support. Functionalized solid supports can be produced by methods known in the art and, if desired, obtained from any of several commercial suppliers for beads and other supports having surface chemistries that facilitate the attachment of a desired functionality by a user. Exemplary surface chemistries that are useful include, but are not limited to, amino groups such as aliphatic and aromatic amines, carboxylic acids, aldehydes, amides, chloromethyl groups, hydrazide, hydroxyl groups, sulfonates or sulfates. If desired, a component can be attached to a solid support via a chemical linker. Such a linker can have characteristics that provide, for example, stable attachment, reversible attachment, sufficient flexibility to allow desired interaction with another reaction component, or to avoid undesirable binding reactions. Exemplary methods that can be used in the invention to attach polymer probes to a solid support are described in Pease et al., *Proc. Natl. Acad. Sci. USA* 91(11):5022-5026 (1994); Khrapko et al., *Mol Biol* (Mosk) (USSR) 25:718-730 (1991); Stimpson et al., *Proc. Natl. Acad. Sci. USA* 92:6379-6383 (1995) or Guo et al., *Nucleic Acids Res*. 22:5456-5465 (1994), each of which is incorporated herein by reference in its entirety.

A reaction component can be attached to a support in a way that provides detection at a single molecule level or at an ensemble level. For example, a population of nucleic acids can be attached to a solid support in a way that labeled polymerases that interact with individual nucleic acid molecules in the population can be distinguished from labeled polymerases that interact with all other nucleic acid molecules on the support. Single molecule detection can also be achieved with a population of labeled polymerases that is attached to a solid support in a way that signals arising from a particular polymerase can be distinguished from signals arising from all other polymerases on the support. Reaction components can be separated from each other on a solid support due to surface features or contours such as those that form wells, posts, channels or the like. Alternatively or additionally, separation can be achieved by providing spacing between molecules that is greater than the resolution of a particular detection device that is in use.

Ensemble detection can be achieved for reaction components that are attached to a surface to form colonies or clusters for ensemble detection. Colonies of nucleic acids can be attached to a surface using methods known in the art such as bridge amplification or emulsion PCR. Useful bridge amplification methods are described, for example, in U.S. Pat. No. 5,641,658; U.S. Patent Publ. No. 2002/0055100 A1; U.S. Pat. No. 7,115,400; U.S. Patent Publ. No. 2004/0096853 A1; U.S. Patent Publ. No. 2004/0002090 A1; U.S. Patent Publ. No. 2007/0128624 A1; and U.S. Patent Publ. No. 2008/0009420 A1, each of which is incorporated herein by reference in its entirety. Another useful method for amplifying nucleic acids on a surface is rolling circle amplification (RCA), for example, as described in Lizardi et al., *Nat. Genet.* 19:225-232 (1998) and US 2007/0099208 A1, each of which is incorporated herein by reference in its entirety. RCA can also be used to amplify nucleic acids in solution to produce DNA concatamers that are subsequently attached to a surface or subsequently used as a template for producing surface attached copies, for example, as described in US 2008/0234136 A1 and U.S. Pat. No. 6,797,474, each of which is incorporated herein by reference in its entirety. Exemplary emulsion PCR methods are described in Dressman et al., *Proc. Natl. Acad. Sci. USA* 100:8817-8822 (2003), WO 05/010145, or U.S. Patent Publ. Nos. 2005/0130173 or 2005/0064460, each of which is incorporated herein by reference in its entirety.

The complexity of an array can vary depending on the desired use of the array. Arrays useful in the invention can have complexity that ranges from about 2 different features to many millions, billions or higher. The density of an array can be from 2 to as many as a billion or more different features per square cm. For example an array can have at least about 100 features/$cm^2$, at least about 1,000 features/$cm^2$, at least about 10,000 features/$cm^2$, at least about 100,000 features/$cm^2$, at least about 10,000,000 features/$cm^2$, at least about 100,000,000 features/$cm^2$, at least about 1,000,000,000 features/$cm^2$, at least about 2,000,000,000 features/$cm^2$ or higher.

Detection can be carried out in a method set forth herein, using a technique that is appropriate to the label being used. In various embodiments, the technique will have a time resolution that can distinguish events occurring in the millisecond time range, for example, when used for pre-equilibrium kinetic analysis. Appropriate techniques include, but are not limited to, fluorescence, fluorescence (or Förster) resonance energy transfer (FRET), chemiluminescence, electroluminescence, Rayleigh Scattering, Mie Scattering, Raman scattering, electromagnetic energy absorption, electromagnetic energy polarization or electrical sensing (e.g. MOSFET, ISFET).

For light based approaches the detection system can include incident radiation and optical elements, e.g. filters, detectors, polarizers, lenses, to condition light that directly or indirectly propagates or to detect a signal from an optical label. In particular embodiments, the incident radiation in a light-based detection approach can be via total internal reflection fluorescence (TIRF), epi-illumination, surface plasmons, two-photon excitation, far field detection, polarized excitation and emission, or any form of electromagnetic radiation that is permuted when incident upon the sample, such that it can be detected.

Electrical sensing can be mediated via a label linked to a polymerase, nucleotide or other molecule to be detected. Examples include but are not limited to inorganic or organic molecules and nanoparticles. Using MOSFET technology, for example, as described in Bergveld, P., *Sensors and Actuators*, 88 (3), (2003) (which is incorporated herein by reference in its entirety), the measured signal can be the drain current which is dependent on the input voltage and the choice of linkage to the polymerase and/or nucleotide. Alternative schemes may be used in the ISFET format, such that a change in the electrical properties of a solution is detected.

The transient state (or the transient dynamic) of a polymerase at a nucleic acid feature can be determined from a time based measurement in a method set forth herein. In particular embodiments, the transient state (or the transient dynamic) is determined from the time duration for the binding reaction to reach equilibrium. The transient state (or the transient dynamic) can also be determined from one or more kinetic constants including, for example, the binding rate constants (e.g. $k_{on}$ or association rate constant, $k_{off}$ or dissociation rate constant, $V_{off}$ or dissociation constant post-incorporation) for the binding of the polymerase to the nucleic acid features. Another useful kinetic constant is the catalytic rate constant ($k_{cat}$) for incorporation of a nucleotide into a nucleic acid features.

A method of distinguishing nucleotide sequences, although exemplified herein with regard to a single nucleotide extension event, can be carried out for a number of different nucleotide species. For example, a method can include the steps of (a) mixing a plurality of different nucleic acid molecules with polymerase molecules and nucleotide molecules, wherein the different nucleic acid molecules are attached to a surface in the form of an array of nucleic acid features; (b) monitoring binding of the polymerase molecules to the nucleic acid features at several points during a pre-equilibrium time period, thereby determining a transient state of the polymerase molecules at the nucleic acid features; (c) identifying nucleic acid features of the array that correctly incorporate the nucleotide molecules based on the transient state of the polymerase molecules at the nucleic acid features, thereby distinguishing the nucleotide sequences for the different nucleic acid molecules; (d) removing the polymerase molecules from the nucleic acid features, thereby providing restored features; (e) mixing the restored features with polymerase molecules and a second species of nucleotide molecules, wherein the second species of nucleotide molecules is different from the species of nucleotide molecules in (a); and (f) repeating (b) and (c) for the restored features, thereby distinguishing the nucleotide sequences for the different nucleic acid molecules. Optionally, for embodiments that use nucleotides having reversible blocking moieties, step (d) can include removing or modifying the blocking moieties at the nucleic acid features that correctly incorporate the nucleotide molecules. Thus, the nucleic acid molecules at the features can be rendered extension competent for steps (e) and (f). Alternatively or additionally, the method can determine a transient dynamic of the polymerase molecules at the nucleic acid features at step (b).

A method of the present disclosure can include sequential deliveries of different nucleotides. For example, the four different nucleotide species A, C, T and G can be delivered (in any order) to an array in four sequential steps. Furthermore, sequential delivery of different nucleotide species can constitute a cycle that is repeated multiple times. For example, the four steps whereby A, C, T and G are delivered to an array can be repeated in 2 cycles whereby the sum total of nucleotide delivery steps is A, C, T, G, A, C, T and G. The order of nucleotide additions is exemplary and can differ to suit a particular application of the methods. Furthermore, the order of nucleotide addition can be the same for one or more cycles of a sequencing reaction or the order can differ between cycles. The number of cycles can be at least 2, 3, 5, 10, 50, 100, 250, 500, 1000, 10000 or more. Typically, four different nucleotide species will be delivered per cycle, but if desired, fewer than four nucleotides can be delivered in a given cycle.

In a particular embodiment, one or more nucleotide species having blocking moieties can be delivered such that single base extension occurs. Deblocking and washing steps can be carried out between nucleotide addition steps. Typically a chemically reactive deblocking moiety is used; however a photo-sensitive block can be used for fast deblocking by light. Exemplary modifications that can be used to render a nucleotide reversibly blocked and respective deblocking reagents are described in U.S. Pat. Nos. 7,427,673; 7,414,116; 7,057,026; and 8,241,573 and PCT publications WO 91/06678 and WO 07/123744, each of which is incorporated herein by reference in its entirety. For embodiments where reversibly blocked nucleotides are used, the number of cycles can be at least 2, 3, 5, 10, 50, 100, 250, 500, 1000, 10000 or more thereby causing extension of a nucleic acid by at least 2, 3, 5, 10, 50, 100, 250, 500, 1000, 10000 or more nucleotides, respectively.

This disclosure also provides a system for determining sequences of nucleic acids from pre-equilibrium kinetic measurements of extension reactions for the nucleic acids. The system can include (a) an array having nucleic acid features with different nucleotide sequences; (b) a fluidic apparatus configured to deliver sequencing reagents to the array, wherein the sequencing reagents include polymerase molecules and nucleotide molecules for the nucleic acid extensions reactions; (c) a detection apparatus configured to obtain the kinetic measurements from the array at a resolution that distinguishes individual nucleic acid features of the array; (d) a control module including instructions for (i) directing the fluidic apparatus to deliver the sequencing reagents to the array at an initiation time point, and (ii) directing the detection apparatus to obtain the kinetic measurements during the pre-equilibrium time period relative to the initiation time point; and (d) an analysis module including instructions for (i) processing the kinetic measurements to determine binding of the polymerase molecules to the nucleic acid features at several points during the pre-equilibrium time period, thereby determining transient state of the polymerase molecules at the nucleic acid features, and (ii) identifying nucleic acid features that correctly incorporate the nucleotide molecules based on the transient state of the polymerase molecules at the nucleic acid features. Alternatively or additionally, the system can determine a transient dynamic of the polymerase molecules at the nucleic acid features.

Figure 5:
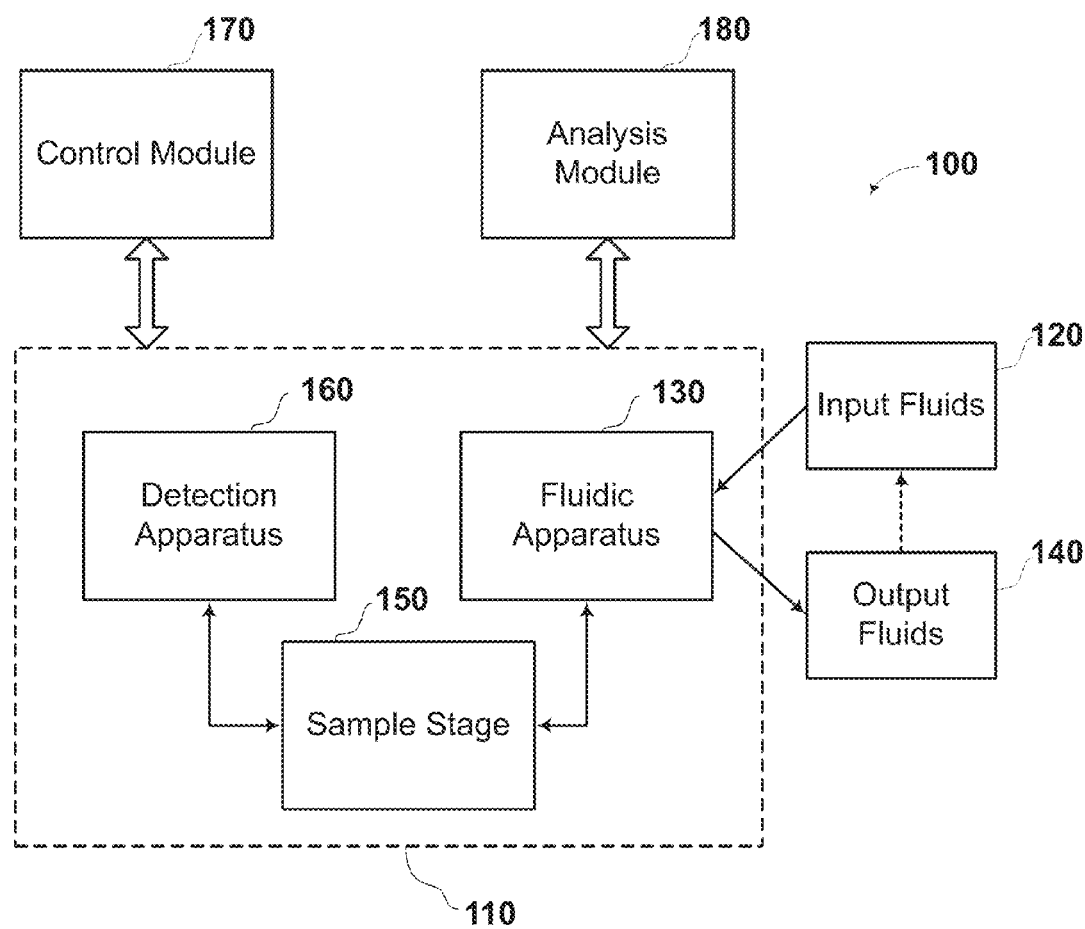
FIG. 5 shows a diagrammatic representation of an exemplary sequencing system.

A diagrammatical representation of an exemplary system 100 for determining sequences of nucleic acids is shown in FIG. 5. The system 100 includes a sample processing device 110 designed to determine the nucleotide sequence(s) for a sample, The sample can be an array or other sample set forth herein and can be present at the sample stage 150. The sample stage is in fluidic communication with a fluidic apparatus 130. The fluidic apparatus delivers input fluids 120 to the sample and removes output fluids 140 from the sample. In some embodiments the input fluids 120 and output fluids 140 are contained in reservoirs. As shown by the dashed arrow in FIG. 5, the fluidic system can optionally recycle one or more of the reagents or other fluids used in a sequencing reaction. The exemplary system of FIG. 5 also includes a control module 170 that is configured to direct various processes carried out by the sample processing device 110 and optionally other components of the system 100. The exemplary system further includes an analysis module 180 that receives data from the sample processing device 110 and analyzes the data, for example, to determine the nucleotide sequence(s) for a sample. The analysis module 180 can optionally receive data from other components of the system 100 as well and use the data as part of one or more analyses. Further details of the exemplary sequencing system are set forth below. Furthermore, various embodiments for a sequencing system are also set forth below and will be apparent from the previous description of methods for determining nucleotide sequences.

Sample processing device 110 generally includes hardware for fluidic manipulation of a sample and for detection of the sample. The sample processing device 110 is typically contained within a single compartment, for example, having a casing that protects the interior components from dust, light and other environmental factors. However, it will be understood that the system need not be contained in a single compartment as one or more of the components described herein can optionally be separated from other components of the system.

A sample stage 150 that is present in the sample processing device can be configured to position a sample to interact with the fluidic apparatus 130 and the detection apparatus 160. Any of a variety of sample devices can be used, including for example, an array of nucleic acids or other formats set forth herein. In particular embodiments the array occurs in a flow cell that allows convenient fluidic manipulation of the array. Exemplary flow cells are described, for example, in US Pat. App. Publ. No. 2010/0111768 A1, WO 05/065814 and US Pat. App. Publ. No. 2012/0270305 A1, each of which is incorporated herein by reference in its entirety. Generally, the sample stage will position the sample (e.g. surface of an array) to be in fluid communication with the fluidic apparatus 130 so that input fluids can be delivered to the sample (e.g. the surface) and output fluids can be removed from the sample (e.g. the surface). The sample stage can also be configured to position the sample such that one or more reactions occurring in the sample (e.g. on the surface of an array) can be detected by the detection apparatus 160. The sample stage can include one or more translational devices that allow samples to be moved in one or more dimensions (e.g. x, y or z dimensions in a Cartesian coordinate system, where z is orthogonal to the surface being detected and/or direction of fluid flow).

Fluidic apparatus 130 can include any of a variety of known devices for pushing or pulling fluids. Examples include, but are not limited to, a syringe pump, diaphragm pump, electroosmotic pump (for example, as described in WO2009/102688 or WO2010/062965, each of which is incorporated by reference herein in its entirety), piezoelectric or peristaltic pumps (for example, as described in U.S. Pat. Nos. 7,268,466; 7,459,066; or 4,997,347, each of which is incorporated by reference herein in its entirety), microfluidic pump, or nanofluidic pump. Particularly useful pumps deliver high flow rates. For example, the flow rate can be at least about 20 ml/min, 30 ml/min, 40 ml/min, 50 ml/min, 100 ml/min or higher. The uniformity and impulse of the flow can be controlled by using high flow delivery rates.

A fluidic apparatus 130 can be configured for stopped-flow fluid delivery. For example, a stopped-flow fluidic apparatus can be configured to rapidly drive small volumes of solutions from syringes into a high efficiency mixer to initiate a fast reaction. The resultant reaction volume then displaces the contents of detection site thus filling it with freshly mixed reagents. The volume injected is limited by the stop syringe which provides the "stopped-flow." As the solution fills the stopping syringe, the plunger hits a block, causing the flow to be stopped instantaneously. Useful configurations for stopped-flow fluidic apparatus are described, for example, in Kuchta, et al., *Biochemistry* 26, 8410-8417 (1987), or Johnson, *The Enzymes*, XX, 1-61 (1992), each of which is incorporated herein by reference in its entirety.

A fluidic apparatus 130 used in a system of the present disclosure can be configured to deliver fluid boluses or droplets. For example, fluid droplets can be separated by a bubble (e.g. an air bubble or a bubble of fluid that is not miscible with the reagent bearing fluid droplet). Exemplary devices for delivering fluid droplets include electrowetting droplet-based apparatuses such as those described in U.S. Publication No. 2011/0059865 A1; U.S. Pat. Nos. 6,911,132 or 7,851,184, or WO 2010/077859 A1, each of which is incorporated herein by reference in its entirety.

Figure 6:
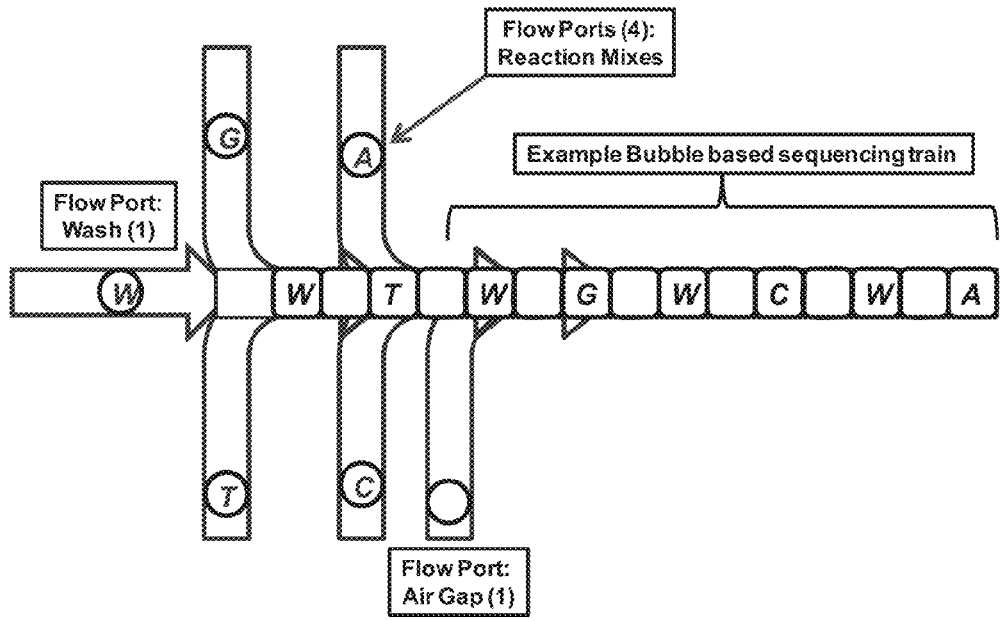
FIG. 6 shows an exemplary fluidic apparatus for delivering fluid droplets to a detection site used in a sequencing system.

FIG. 6 shows a diagram of an exemplary fluidic apparatus for delivering reagent droplets. As shown, the fluidic apparatus provides a train of reagent droplets W (wash), T (thymine nucleotide), W (wash), G (guanine nucleotide), W (wash), C (cytosine nucleotide), W (wash), and A (adenine nucleotide). Each reagent droplet is separated from other reagent droplets by a gap droplet, which is air or oil in the diagram. Each droplet (e.g. W, T, G, C, A, and gap bubble) can be delivered to the fluid train from a separate reservoir. It will be understood that the order of nucleotides is exemplary. Furthermore, droplets containing other reagents appropriate to a method described herein can also be used. Wash droplets are optional. Any number of wash droplets can be delivered to a detection site between deliveries of reagent droplets to suit a desired level of washing.

In particular embodiments, one or more of the reagents used in a system or method of the present disclosure can be recycled. Fluidic systems that discretely deliver reagent droplets can be advantageously used for recycling of reagents. As used herein, the term "discretely deliver," when used in reference to droplets, means the droplets separately enter a detection site (or other location) such that they remain unconnected to each other as they enter. Similarly, the term "discretely removed," when used in reference to droplets, means the droplets separately exit a location such that they remain unconnected to each other as they exit. Maintaining droplet integrity provides several advantages over techniques that use fluid displacement for reagent delivery. Fluid displacement typically results in dilution of reagents when the displacing fluid interfaces with the fluid to be displaced. Moreover, components of the displacing fluid are typically introduced into the fluid being displaced. In contrast, when the integrity of a droplet that contains the reagents is maintained, such dilution and contamination can be reduced or avoided. Thus, the reagents in the droplets can be more readily re-used, for example, without having to resort to procedures for concentrating or purifying reagents.

An individual droplet that is re-used in a sequencing reaction can include a polymerase that is not consumed in a sequencing cycle by virtue of its role as a catalyst. An individual droplet can include one or more other reagents that are consumed in a sequencing cycle. For example, a droplet can contain an excess amount of a non-catalyst reagent such that the droplet is not entirely depleted upon completion of one or even several cycles of the sequencing reaction. A droplet that contains a polymerase or an excess amount of a consumable reagent can be reused once or several times.

In particular embodiments, a droplet that has been through one or more cycles of a sequencing reaction can be modified or replaced. For example, a droplet can be modified by addition of reagent(s) to replenish the contents of the droplet or the droplet can be replaced with an entirely new droplet having similar reagent(s). The modified droplet or replacement droplet can then be used for subsequent sequencing cycles.

Different droplets can be modified or replaced independently of each other. In a particular embodiment, droplets carrying different species of reagents can be modified or replaced on different schedules. For example, a droplet containing a polymerase may be functional for a larger number of cycles than a droplet containing nucleotides. This may be the case for a polymerase that is robust enough to retain activity for a number of cycles that exceeds the number of cycles at which nucleotides are effectively depleted from one or more nucleotide droplet. Accordingly, a nucleotide droplet can be replaced or modified more often than a polymerase droplet. The situation may of course be reversed, for example, where the polymerase is relatively fickle and a large enough excess of nucleotide is present in the nucleotide droplet that the polymerase droplet effectively loses activity before the nucleotide droplet is depleted. Thus, it may be desirable to replace or modify the polymerase droplet more often than the nucleotide droplet.

A given droplet can be replaced or modified after at least 1, 2, 3, 4, 5, 6, 7, 8, 9, 10, 15, 20, 30, 40, 50, 60, 70, 80, 90, 100 or more uses. Alternatively or additionally, a droplet can be used no more than 1, 2, 3, 4, 5, 6, 7, 8, 9, 10, 15, 20, 30, 40, 50, 60, 70, 80, 90, or 100 times before it is replaced or modified.

A device that uses electrowetting techniques is particularly useful for embodiments where reagents are recycled. A series of different droplets can deliver different reagents to a detection site (e.g. at a sample stage) in a sequential order to complete a cycle of sequencing. The cycle can occur for one or more target nucleic acids (e.g., in an array). The fluidic path can be circular such that one or more of the droplets can make several laps, contacting the detection surface each time around. The path can have other shapes that accommodate droplet re-use such as serpentine, clover leaf, figure-eight, spiral or the like.

A detection apparatus that is used in a sequencing system of the present disclosure, such as the system exemplified in FIG. 5, can be one that is suitable to detect a particular label that is used in a sequencing reaction. Appropriate devices include, but are not limited to, an optical detector such as a charge coupled device (CCD) or a complementary metal-oxide-semiconductor (CMOS), or an electrical detector such as a metal oxide semiconductor field-effect transistor (MOSFET) or ion-sensitive field-effect transistor (ISFET). In particular embodiments a CMOS imager having a single-photon avalanche diode (CMOS-SPAD) can be used, for example, to distinguish fluorophores using fluorescence lifetime imaging (FLIM). Exemplary CMOS based systems that can be used for FLIM are described in US Pat. App. Publ. No. 2008/0037008 A1; Giraud et al., *Biomedical Optics Express* 1: 1302-1308 (2010); or Stoppa et al., *IEEE European Solid-State Device Conference* (ESSCIRC), Athens, Greece, IEEE, pp. 204-207 (2009), each of which is incorporated herein by reference in its entirety. Other useful detection devices that can be used include, for example, those described in U.S. Pat. No. 7,329,860 and US Pat. App. Publ. No. 2010/0111768 A1, each of which is incorporated herein by reference in its entirety.

In embodiments that utilize an optical detector, one or more light sources can provide incident radiation to a sample. The light sources can include one or more lasers, with multiple lasers typically being used for detecting dyes that fluoresce at different corresponding wavelengths. The light sources may direct the light to conditioning optics for filtering, splitting, shaping or otherwise manipulating radiation that is to be incident upon a sample. For example, the conditioning optics can combine beams from multiple lasers and generate a beam of radiation that is conveyed to focusing optics. Exemplary conditioning optics include, for example, filters, polarizers, lenses, reflectors and the like. Similar optics can be used to condition emission light or other detectable light that is transmitted from a sample to an optical detector.

Detection apparatus 160 can be configured to obtain measurements from an array of features at a resolution that distinguishes individual features of the array. Exemplary size ranges for such features are set forth herein above. Detection apparatus 160 can be further configured to obtain pre-equilibrium kinetic measurements at such resolutions. Accordingly, a particularly useful detection apparatus will be configured to obtain signals at a rate of at least $1 \times 10^4$ signals/second. Slower rates are also useful including, for example, a rate that is at least $1 \times 10^3$ signals/second, 100 signals/second, 10 signals/second, 1 signal/second, 1 signal/10 seconds, 1 signal/30 seconds or slower. Rates faster than those exemplified above can also be useful if available using suitable detection hardware. Imaging devices are particularly useful, especially when fluorescent labels are used. An imaging apparatus can be configured to obtain images of an array at the resolutions exemplified above and at a data rate that is amenable to obtaining pre-equilibrium kinetic measurements. For example, an imaging apparatus can be configured to obtain images of an array at a rate that is in a range exemplified above for general detection apparatus.

Returning to the exemplary system diagramed in FIG. 5, control module 170 can communicate with sample processing device 110 to direct the function of detection apparatus 160 and fluidic apparatus 130. Control module 170 will typically include one or more programmed processors, or general purpose or application-specific computers which communicate with sensors and other processing systems within the detection apparatus 160 and fluidic apparatus 130. Control module 170 can include instructions for (i) directing the fluidic apparatus 130 to deliver the sequencing reagents to the array at an initiation time point, and (ii) directing the detection apparatus 160 to obtain the kinetic measurements during the pre-equilibrium time period relative to the initiation time point. The instructions can synchronize signal acquisition by the detection apparatus 160 with initiation of fluid delivery by the fluidic apparatus 130. For example, the control module 170 can instruct a stopped-flow fluidic apparatus to deliver a known volume of reagent at a known flow rate. The control module 170 can further instruct the detection apparatus 160 to begin acquiring signal at a time point and for a duration based on the known dead time for the sample processing device 110.

The control module 170 can include instructions appropriate to the sequencing method to deliver different sequencing reagents to complete one or more sequencing cycles in accordance with methods set forth herein. For example, the control module 170 can instruct the fluidic apparatus 160 to sequentially deliver sequencing reagents comprising four different nucleotide species, respectively, to the array. Numerous cycles can be repeated in accordance with methods set forth herein. Accordingly, the control module 170 can further provide instructions to repeat, several times, the sequential delivery of the four different nucleotide species, respectively, to the array.

The analysis module 180 of the system shown in FIG. 5 can include instructions for processing pre-equilibrium kinetic measurements to determine binding of polymerase molecules to one or more nucleic acid features, thereby determining transient state (or transient dynamic) of the polymerase molecules at the nucleic acid features. Analysis module 180 will typically include one or more programmed processors, or general purpose or application-specific computers which communicate with sensors and other processing systems within the detection apparatus 160 and fluidic apparatus 130. The analysis module 180 can further include instructions for identifying nucleic acid features that correctly incorporate the nucleotide molecules based on the transient state (or transient dynamic) of the polymerase molecules at the nucleic acid features. The instructions can be in accordance with the methods set forth herein. For example, the instructions can process acquired data to determine the transient state (or transient dynamic) of a polymerase molecule for a feature of an array based on the time duration for the binding event to reach equilibrium. In another embodiment, the instructions can process acquired data to determine the transient state (or transient dynamic) of a polymerase molecule for a feature of an array based on the binding rate constants for the binding of the polymerase molecules to the nucleic acid features and/or based on the catalytic rate constant for incorporation of a nucleotide into the nucleic acid feature. Exemplary algorithms that can be carried out by analysis module 180 are set forth in Example VIII.

Thus, the analysis module 180 can include instructions to monitor the pre-steady kinetics of polymerase binding to its substrates in the presence of nucleotides that are correctly matched to a nucleic acid template or mismatched. The instructions can further identify a base that is present at a particular location in a template strand of the nucleic acid based on the kinetic measurements and/or characterizations. Furthermore, when data from sequential detection events is processed the data can be used to determine a sequence of nucleotides that is present in the template strand.

EXAMPLE I

Single Molecule Pattern Sequencing Using Pre-Equilibrium Kinetics Scheme 1

Glass coverslips were treated with PEG/PEG-biotin according to single molecule protocols as described by Roy, et al., *Nature Methods*, 5, 507-516 (2008). Coverslips were incubated with 200 pM streptavidin for 15 minutes, washed with 1 ml wash buffer (50 mM Tris pH=7.5; 50 mM NaCl), and incubated for 15 minutes with 200 pM biotinylated DNA template. The target DNA template sequence (SEQ ID NO: 1) is as follows:

```
Biotin-3' CTTGCGTGGACACGTTCGCGAACGTGTCCACGCAAGGA
ATTCG-5'
```

Surfaces were washed after 15 minutes with 1 ml wash buffer and imaged.

Cy3-Klenow was prepared as follows. Purified wild-type Klenow exo- was first treated with 10 mM dithiothreitol (DTT) for 30 min at room temperature to reduce disulfide bonds. Next, wild-type Klenow exo- was purified by fractionating with a Sephadex-25 column using the following buffer: 50 mM ACES pH 7.0, 1 M NaCl, 1 mM EDTA, and 0.01% w/v Tween-20. The fractions with wild-type Klenow exo- were identified by measuring the 280 nm absorption for each fraction. The wild-type Klenow exo-concentration was estimated using the $\epsilon 280=62500$ $M^{-1}$ $cm^{-1}$. Cy3-maleimide (GE Healthcare) was incubated, in 100× molar excess, with the wild-type Klenow exo-. The dye conjugation reaction was allowed to proceed for 12 h at 4° C. The Cy3-Klenow conjugate was purified using two steps. First, a Sephadex-25 column was used to separate Cy3-Klenow from free Cy3 using 50 mM Tris pH 7.5, 1 M NaCl, 1 mM EDTA, 0.01% w/v Tween-20. The fractions containing Cy3-Klenow were identified by measuring the absorption spectrum for each fraction. The fractions with product were pooled and dialyzed against 50 mM Tris pH 7.5, 1 M NaCl, 1 mM EDTA, 0.01% w/v Tween-20 for >4 h at 4° C. The absorption spectrum for final product was used to determine the degree of dyes per polymerase using the dye supplier's specifications. The dye labeling efficiency was estimated to be at least about 70%.

Polymerase reaction buffer was prepared with the following: 10 mM MgSO$_4$; 50 mM ACES pH=6.8; 2.5 mM 2-nitrobenzoic acid; 150 mM NaCl; 5 mM DTT; 5 μM protocatecnhuate 3,4 dioxygenase (Sigma, Cat #P8279); 5 mM 3,4 dihydroxybenzoic acid (Sigma Cat #37580). Cy3-Klenow was diluted to 10 nM in polymerase reaction buffer.

Figure 7:
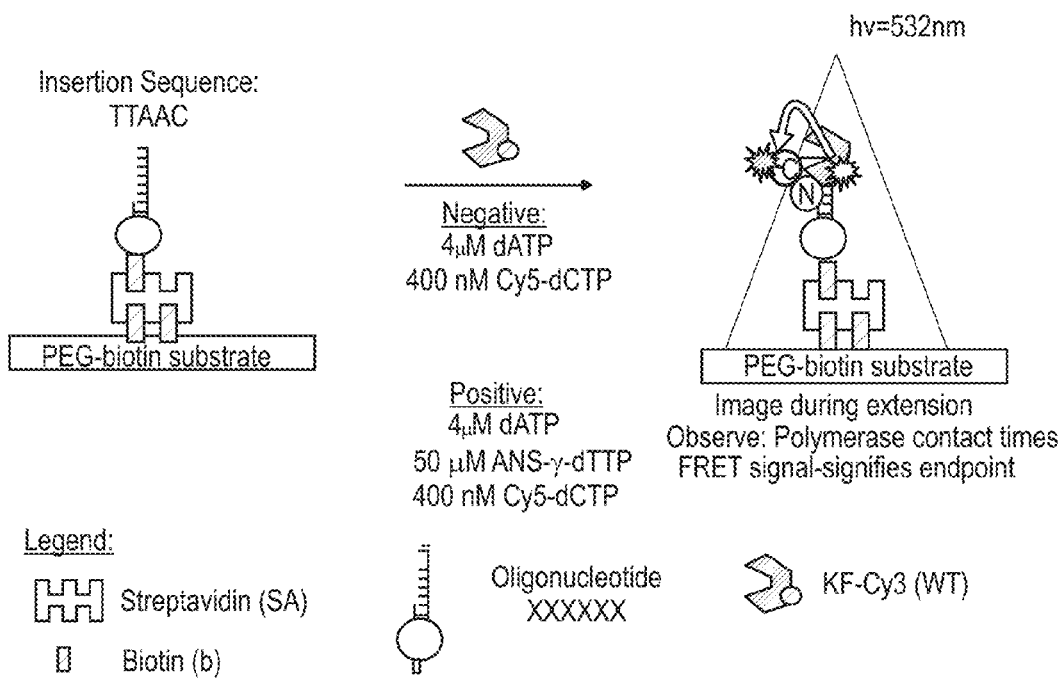
FIG. 7 shows a diagrammatic representation of a single molecule detection scheme.

Single molecule detection scheme 1 was carried out as shown diagrammatically in FIG. 7 and as follows. For positive reactions, the Cy3-Klenow-containing polymerase reaction buffer was mixed with 50 μM modified nucleotide (ANS-γ-dTTP); 4 μM dATP; 200 nM Cy5-dCTP (GE Life Sciences, Cat #PA55031). The negative control, was prepared similarly but with an absence of the initiating nucleotide, ANS-γ-dTTP.

Data was collected on a single molecule detection system, which included an Olympus microscope (IX-71) outfitted with a total internal reflectance fluorescence (TIRF) illuminator, 60×TIRF objective, EMCCD (Andor, iXon 3). The excitation source was a 532 nm laser (Laser Quantum) and the power at the sample was approximately 150 W/cm$^2$. The illumination path included a 532 dichroic (Semrock, Di01-532-R532-25×36) and 532 Razor Edge long pass filter (Semrock). The emission signal was split into two with a 630 Dichroic in the collection path, whereby the low pass FOV houses a 570/90 bandpass (Chroma) and the long pass FOV houses a 640 LP (Chroma, Cat #: T640LPXR). Real-time single molecule data was collected at 30 frames per second for 2 minutes and time trace extraction was performed using a rolling average time trace extraction method using a Gaussian fit model (Cheezum, et al, Biophysical Journal, 1, 2378-2388 (2001), which is incorporated herein by reference in its entirety). Data analysis was performed using the publicly available vbFRET software. (Bronson, E J, et al. *Biophysical Journal*, 97, 3196-205 (2009), which is incorporated herein by reference in its entirety).

Figure 8:
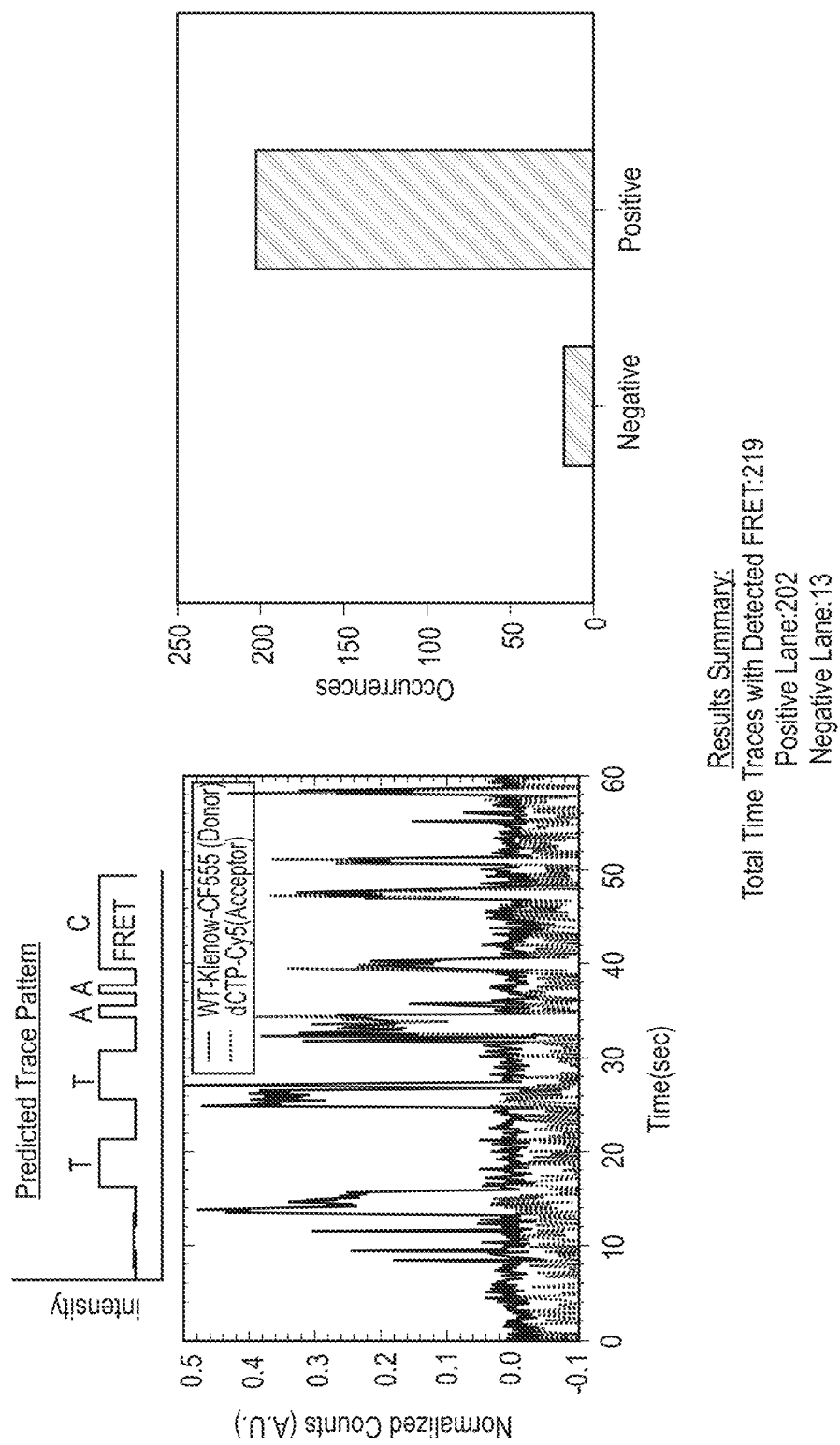
FIG. 8 shows predicted and actual time trace data for a pre-equilibrium polymerase binding reaction (panel A) and a histogram of occurrences for a positive and negative control sample (panel B).
Figure 9:
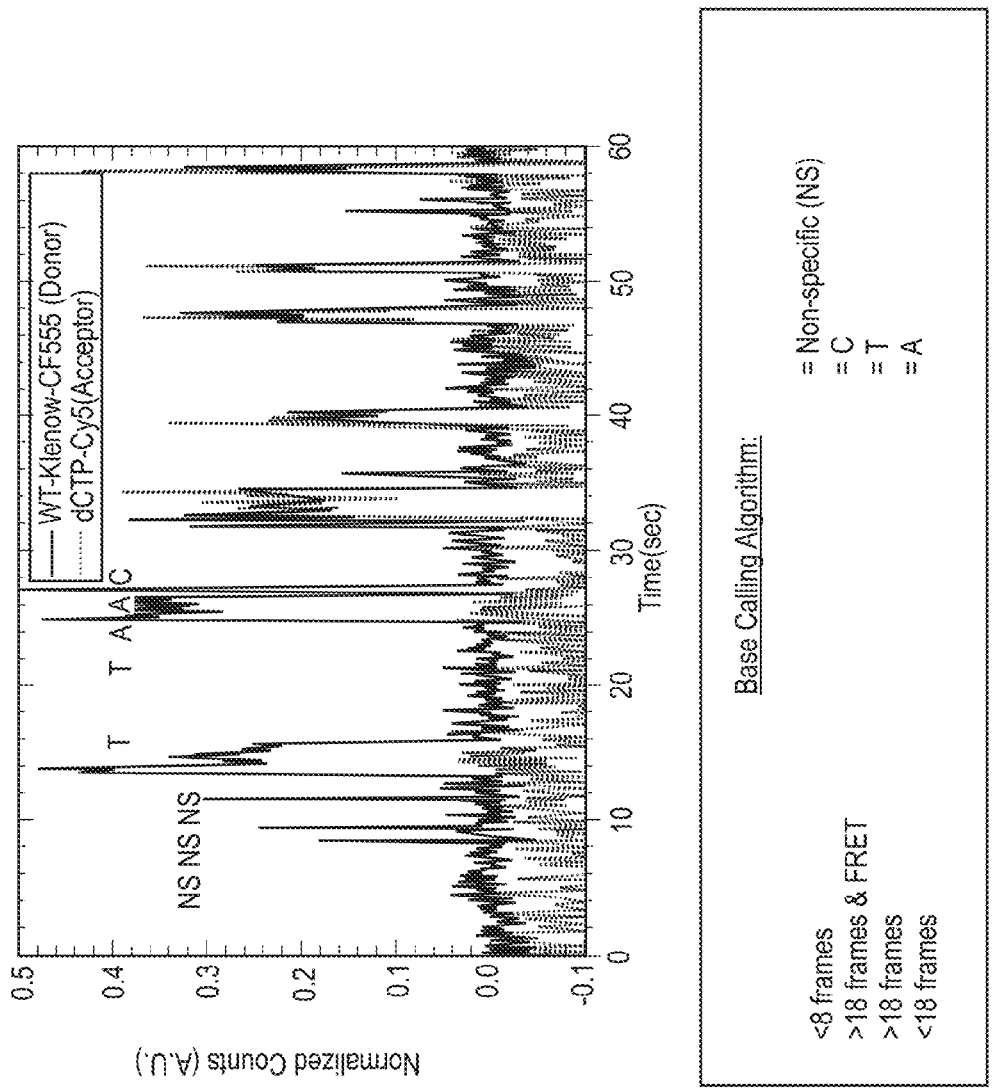
FIG. 9 shows actual time trace data for a pre-equilibrium polymerase binding reaction and an exemplary base calling algorithm.
Figure 10:
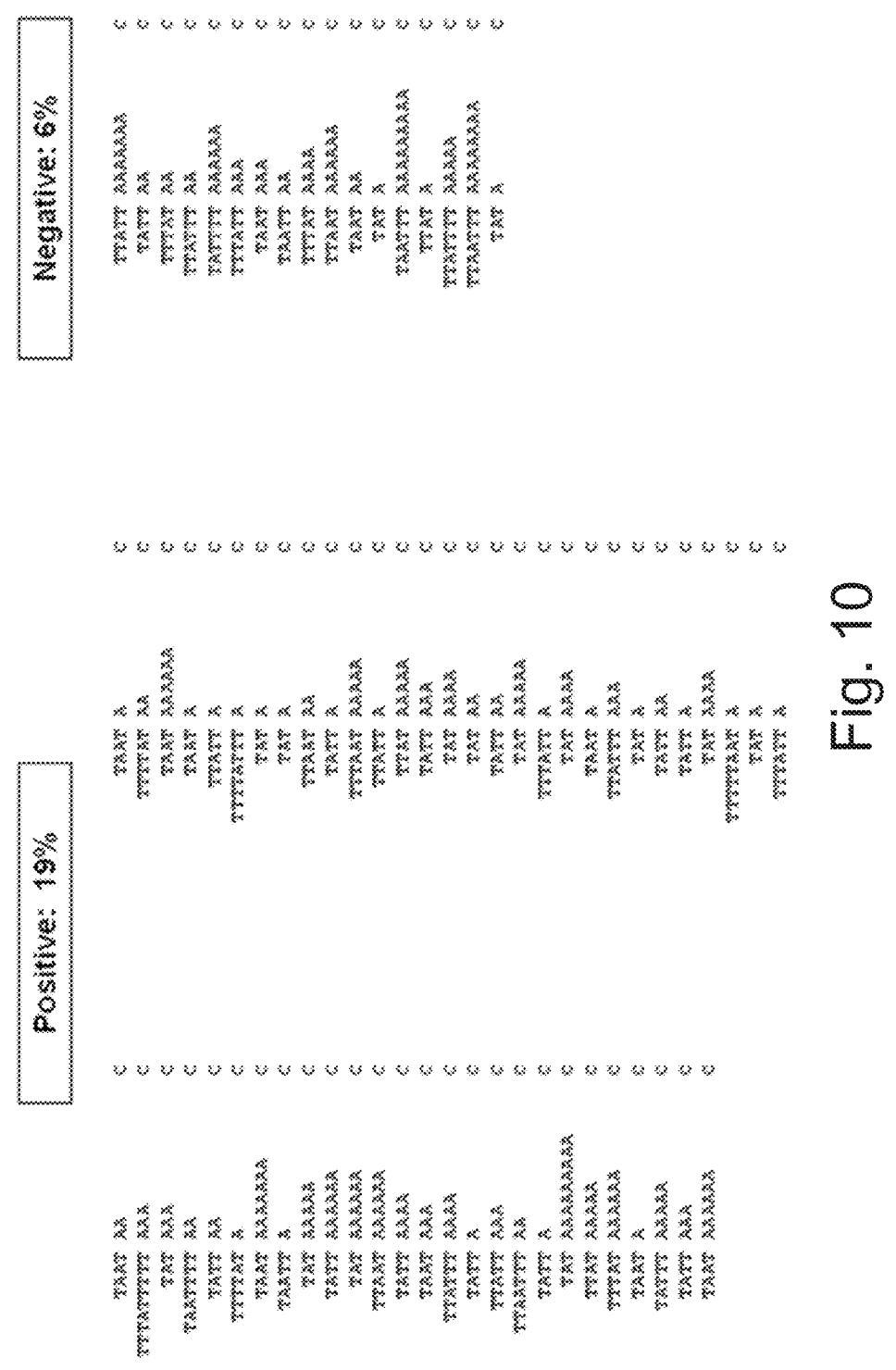

Single time trace data is shown that indicates three time signatures, which distinguish different base incorporations (FIG. 8, left panel). The positive lane showed significantly more FRET events indicating the insertion of a Cy5-dCTP base on the template than the negative control lane, which indicates that the extension reactions were completed (FIG. 8, right panel). Single molecule time trace data was processed using a generic binning algorithm, whereby, signature pulses less than 8 frames were identified as non-specific binding (polymerse/template binding in the presence of the incorrect or no nucleotide), <18 frames indicated the formation of a dATP/polymerase/template binding event, >18 frames indicated the incorporation of ANS-γ-dTTP, and a signature FRET event indicated the binding of a polymerase/template/Cy5-dCTP (FIG. 9). Using this simple algorithm, a pattern that represented the expected insertion sequence could be distinguished (FIG. 10).

EXAMPLE II

Single Molecule Pattern Sequencing Using Pre-Equilibrium Kinetics Scheme 2

Figure 11:
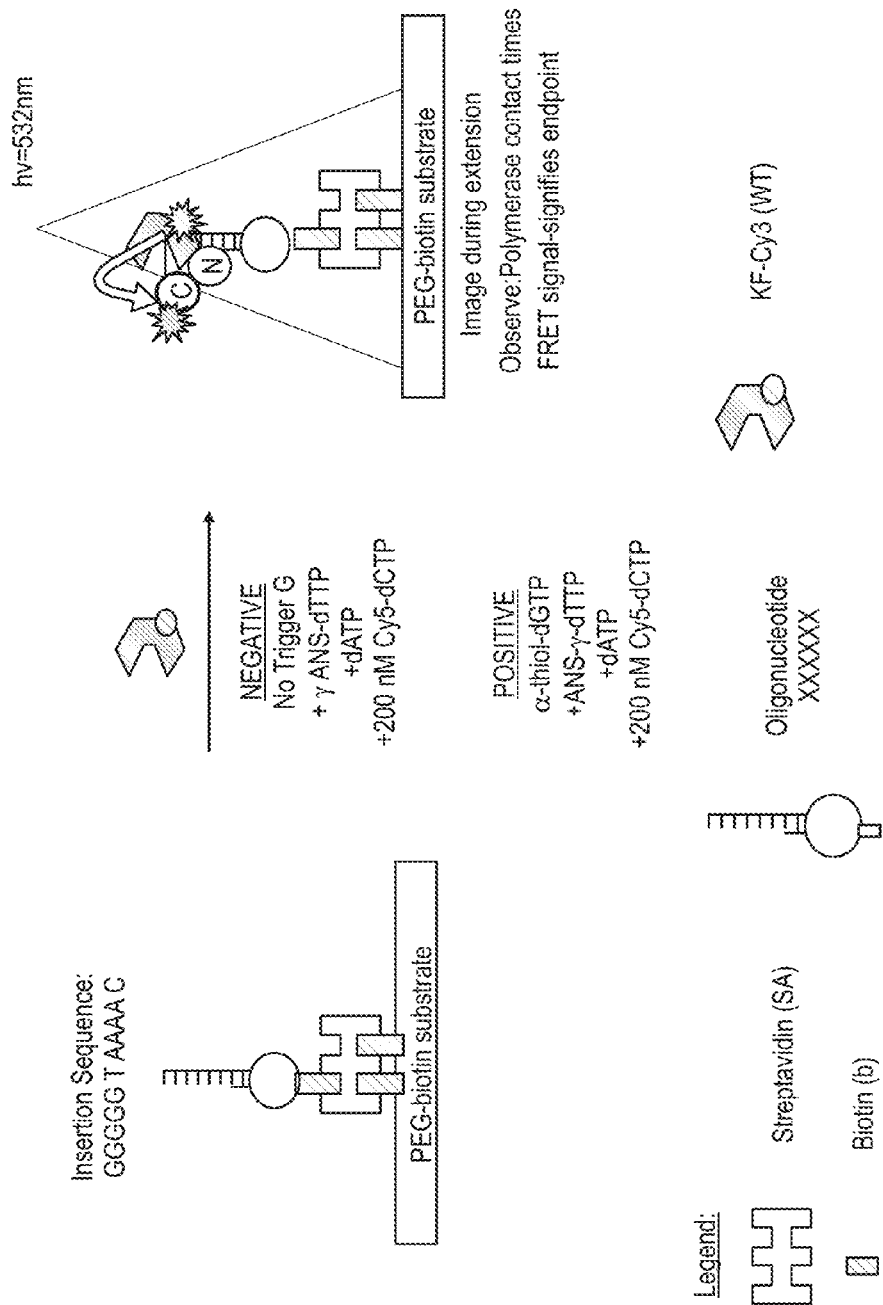
FIG. 11 shows a diagrammatic representation of a single molecule detection scheme.

Scheme 2 was carried out as shown diagrammatically in FIG. 11. The conditions were similar to those set forth above in Example I, but with the following modifications. The target DNA template was: 5'aaaaagggaaaactecttaaacccifiggaaccccgttttaccccGAGAC-GACGCGGTAGGCGCCAGATATGCGATCC3' (SEQ ID NO: 2) having the insertion sequence of GGGGGTAAAAC (SEQ ID NO: 3), and 10 µM 1-Thio-Guanosine-5'-Triphosphate (TriLink Cat #N-8007) was used in the positive reaction. Data was collected on the single molecule detection system described in Example I.

Figure 12:
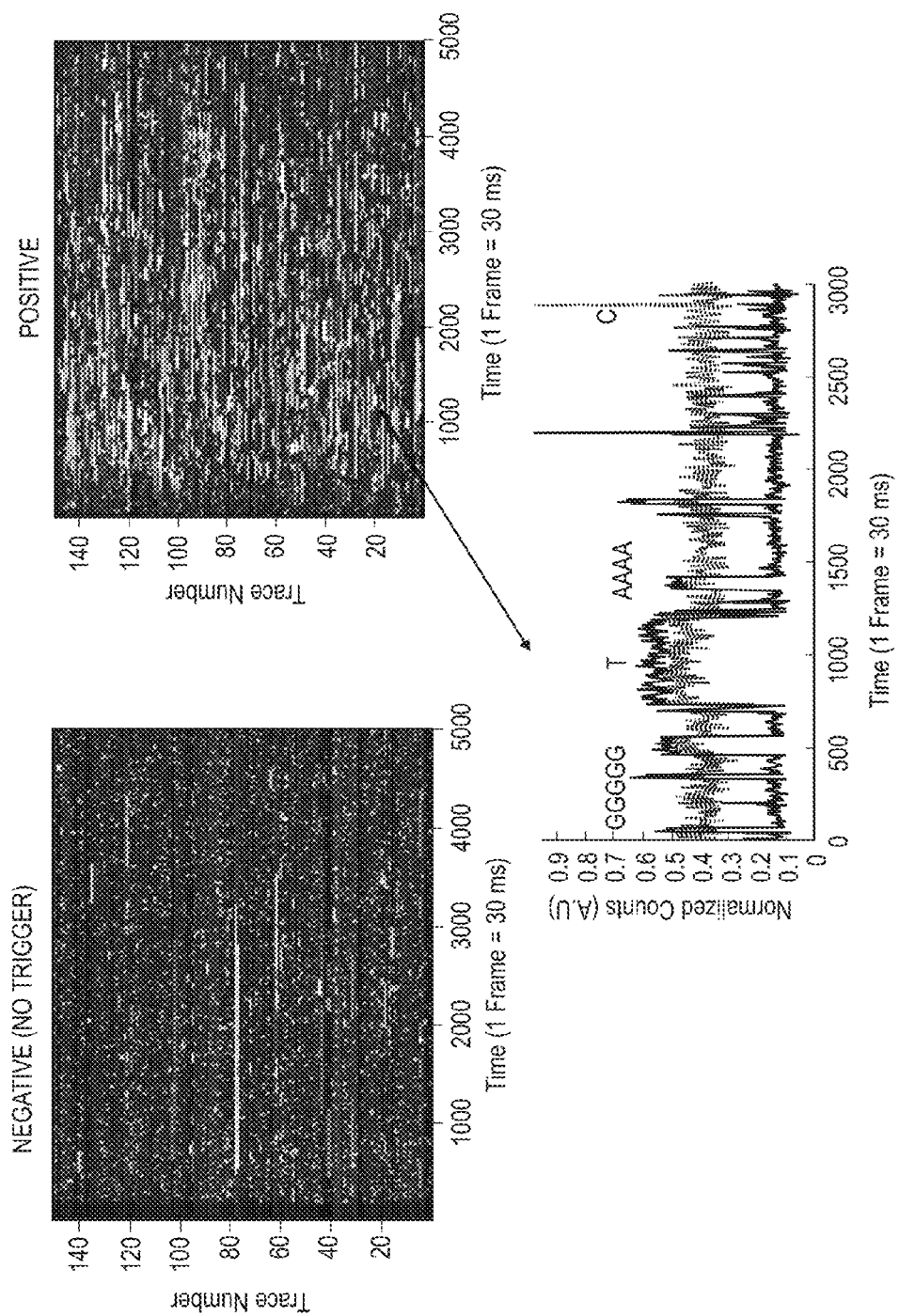
FIG. 12 shows line plots of time trace data from 225 single molecule time traces.

Line plots of time trace data from 225 single molecule time traces (positive and negative controls, FIG. 12) demonstrated the ability to distinguish a homopolymer pattern using the long insertion event from the modified T nucleotide bookmarked by shorter event homopolymer patterns and the insertion event of a base labeled Cy5-dCTP nucleotide. The terminal event is marked by the FRET signal between the labeled base (Acceptor) and labeled polymerase (Donor).

EXAMPLE III

Figure 13:
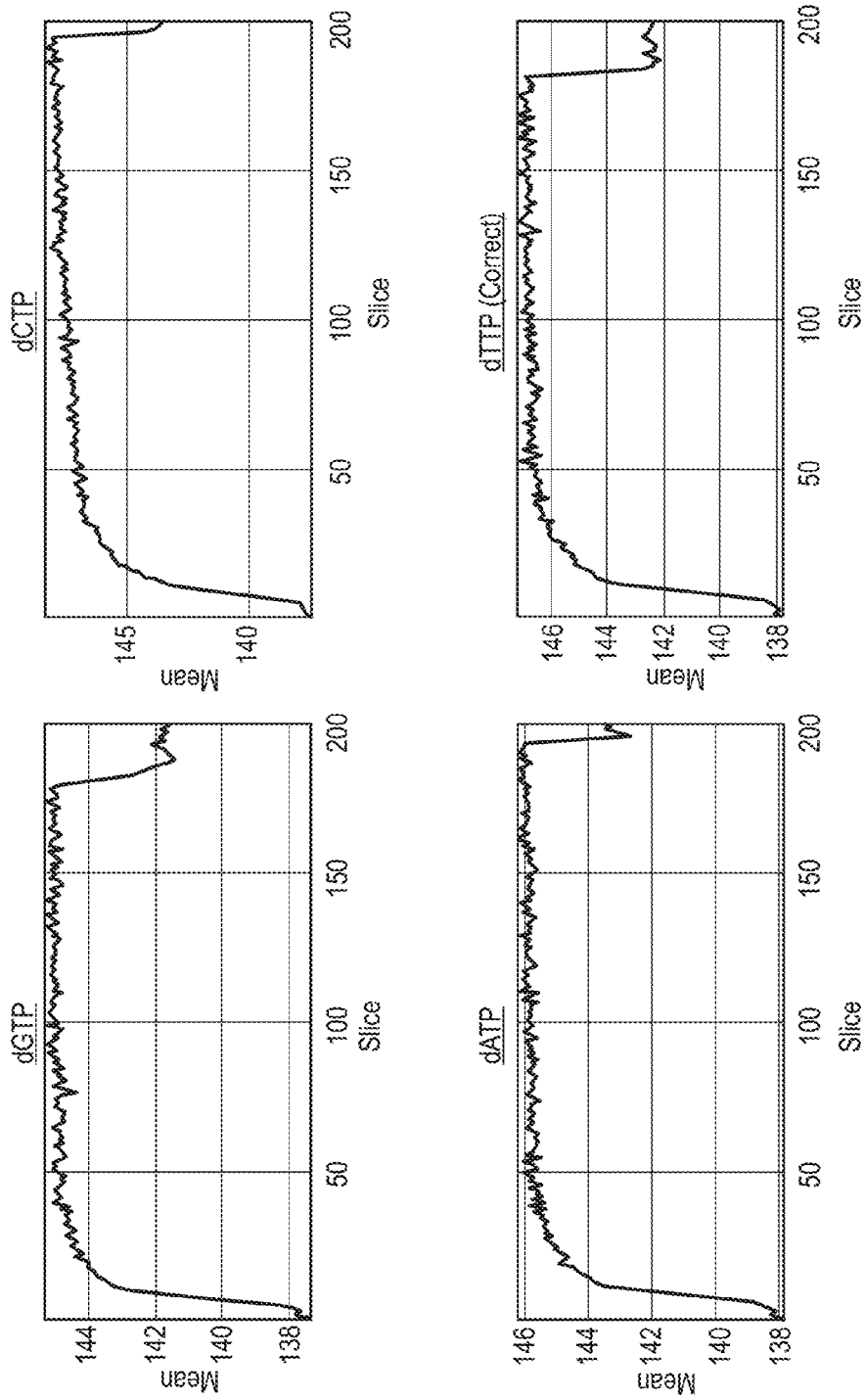
FIG. 13 shows waveforms produced from interaction of a fluorescently labeled polymerase with a nucleic acid in the presence of correctly matched and mismatched nucleotides under single molecule detection conditions.

Ensemble-Level Detection of Pre-Equilibrium Kinetics Using Conditions From Single Molecule Schemes Four flows of sequencing were carried out on an Illumina GA as follows. Genome Analyzer flow cells were coated with primer and hybridized to a control template (Broad Template 3, from the Broad Institute, Cambridge, Mass.) and cluster amplification was performed according to the manufacturer's protocol using paired end cluster chemistry and paired end flow cells V4. Clusters were grown from 0.5 pM input DNA concentration. The resulting flow surface contained a monotemplate field of features for which the first insertion base was "T". Polymerase reaction buffer was prepared from the following: 50 mM ACES pH 6.8; 150 mM NaCl; 5 mM DTT; 10 mM $MgSO_4$; 2.5 mM 2-nitrobenzoic acid; and 0.02% Tween 20. Klenow polymerase was labeled with Cy3 as set forth in Example I. For sequencing, the Cy3 labeled Klenow polymerase was diluted to 150 nM in the polymerase reaction buffer and 4 independent nucleotide mixes ('dATP', 'dGTP', 'dCTP', 'dTTP') were prepared at 25 µM. High salt wash buffer was composed of 50 mM Tris-HCl pH 7.5; 1 M NaCl; and 0.02% Tween 20. Using a synchronized sequencing scheme (one nucleotide delivered at a time), the following flows were repeated: (1) dNTP; (2) High Salt wash; (3) pre-wash with polymerase extension buffer. Reproducing the conditions (formulations and pH) from Example I, it was not possible to discriminate incorrect vs. correct incorporation (FIG. 13). Rather correct vs. incorrect nucleotide discrimination in the ensemble format relied upon a more careful modification of specific formulations (such as salt, nucleotide concentration and pH, which directly impacted $k_{on}$, $k_{cat}$, and $k_{off}$). As set forth in Example V below, in addition to optimizing formulations, mixing rates can be optimized in view of kinetic differences in order to create conditions where the species of the features are in phase for more accurate sequencing in the pre-equilibrium regime.

EXAMPLE IV

Effect of Polymerase on Ensemble-Level Detection of Pre-Equilibrium Kinetics Two flows of sequencing with either Cy3 labeled Bst polymerase or Cy3 labeled human polymerase beta were carried out on an Illumina GA as follows. Genome Analyzer flow cells were coated with primer and hybridized to Broad Template 3 and then cluster amplification was performed according to the manufacturer's protocol using paired end cluster chemistry and paired end flow cells V4. Clusters were grown from 0.5 pM input DNA concentration. The resulting flow surface contained a monotemplate field of features for which the first insertion base was "T". The Cy3 labeled Bst polymerase reaction buffer was prepared from the following: 50 mM ACES pH 6.8; 300 mM NaCl; 5 mM DTT; 10 mM $MgSO_4$; 0.1×BSA; 0.02% Tween 20. For sequencing, the Cy3 labeled Bst polymerase was diluted to 150 nM in the polymerase reaction buffer and 2 independent nucleotide mixes ('dGTP', 'dTTP') were prepared at 100 µM. High salt wash buffer was composed of 50 mM Tris-HCl pH 7.5; 1 M NaCl; 0.02% Tween 20. Using a synchronized sequencing scheme (one nucleotide delivered at a time), the following flows were repeated: (1) dNTP; (2) High Salt wash; (3) pre-wash with polymerase extension buffer. The Cy3 labeled human pol beta polymerase reaction buffer was prepared from the following: 50 mM Tris-HCl pH 8.0; 100 mM KCl; 5 mM DTT; 10 mM $MgSO_4$; 0.1×BSA; 0.02% Tween 20 and 10 mM ascorbic acid. For sequencing, the Cy3 labeled human pol beta polymerase was diluted to 150 nM in the polymerase reaction buffer and 2 independent nucleotide mixes ('dGTP', 'dTTP') were prepared at 100 µM. High salt wash buffer was composed of 50 mM Tris-HCl pH 7.5; 1 M NaCl; 0.02% Tween 20. Using a synchronized sequencing scheme (one nucleotide delivered at a time), the following flows were repeated: (1) dNTP; (2) High Salt wash; (3) pre-wash with polymerase extension buffer.

Figure 14:
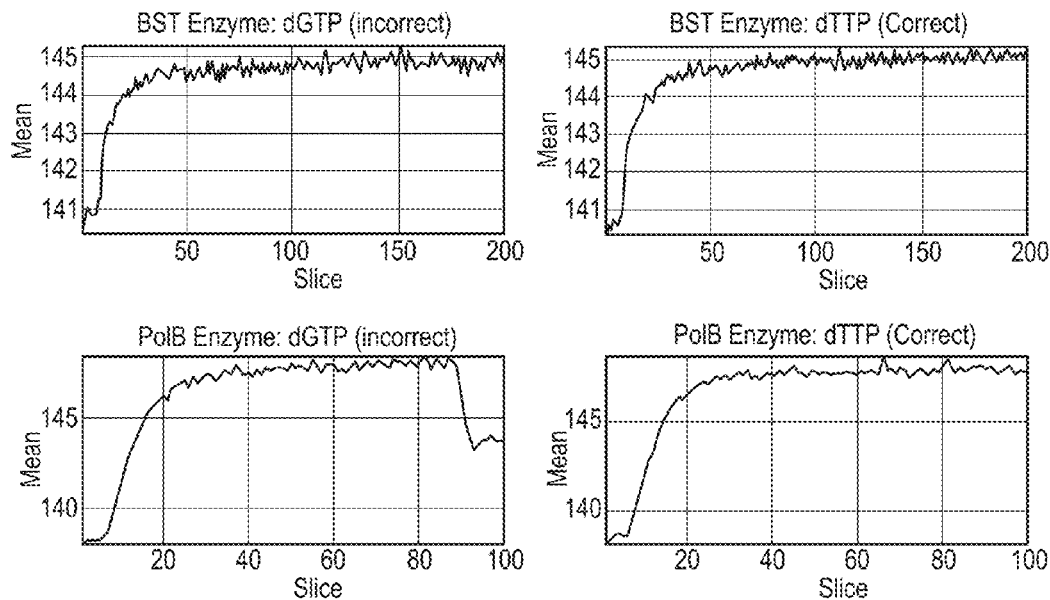
FIG. 14 shows waveforms produced from interaction of a fluorescently labeled polymerase with a nucleic acid in the presence of correctly matched and mismatched nucleotides using different polymerases.

As shown in FIG. 14, neither Bst polymerase nor human Pol B polymerase yielded results that provided a straightforward or convenient distinction between correctly matched nucleotide and a mismatched nucleotide under the conditions tested.

EXAMPLE V

Improved Conditions for Ensemble-Level Sequencing Using Pre-Equilibrium Kinetics Four cycles of sequencing were carried out on an Illumina GA as follows. Genome Analyzer flow cells were coated with primer and hybridized to the C2cal template (5 'AATGATACGGCGACCACCGAGATCTACACTCTTT-CCCTACACGACGCTCTTCCGATCTCCTACGCGAGT-ACTATATACGTACATGCGTGTATGCGTACGTACTACG-TACACGTGACGTTAGAAGATCGGAAGAGCGGTTCA-GCAGGAATGCCGAGACCGATCTCGTATGCCGTCTT-CTGCTTG3' (SEQ ID NO: 4)) and cluster amplification was performed as described in Example III. The resulting monotemplate bearing flow cell was detected as described in Example III, with the following exceptions. Polymerase reaction buffer was prepared from the following: 50 mM ACES pH 6.8 (for dTTP flows), pH 7 (for dATP flows), pH 7.2 (for dCTP flows) and pH 7.4 (for dGTP flows); 300 mM NaCl; 5 mM DTT; 10 mM MgSO4; 0.1×BSA and 0.02% Tween 20. Key elements changed in this reaction compared to Example III were higher salt concentration which directly impacts $k_{off}$ and $V_{off}$ (150 mM vs. 300 mM). In addition, higher nucleotide concentration was used (25 µM vs. 100 µM) and the pH differed between flows, being optimized for individual nucleotide species.

Furthermore, the conditions differed from Example IV by use of the Klenow polymerase. Klenow polymerase was labeled with Cy3 as set forth in Example I. For sequencing, the Cy3 labeled Klenow polymerase was diluted to 150 nM in the polymerase reaction buffer and 4 independent nucleotide mixes ('dATP', 'dGTP', 'dCTP', 'dTTP') were prepared at 100 µM. High salt wash buffer was composed of 50 mM Tris-HCl pH 7.5; 1 M NaCl; 0.02% Tween 20. Using a synchronized sequencing scheme (one nucleotide delivered at a time), the following flows were repeated: (1) dNTP; (2) High Salt wash; (3) pre-wash with polymerase extension buffer. A total of 16 dNTP flows were used.

Figure 15:
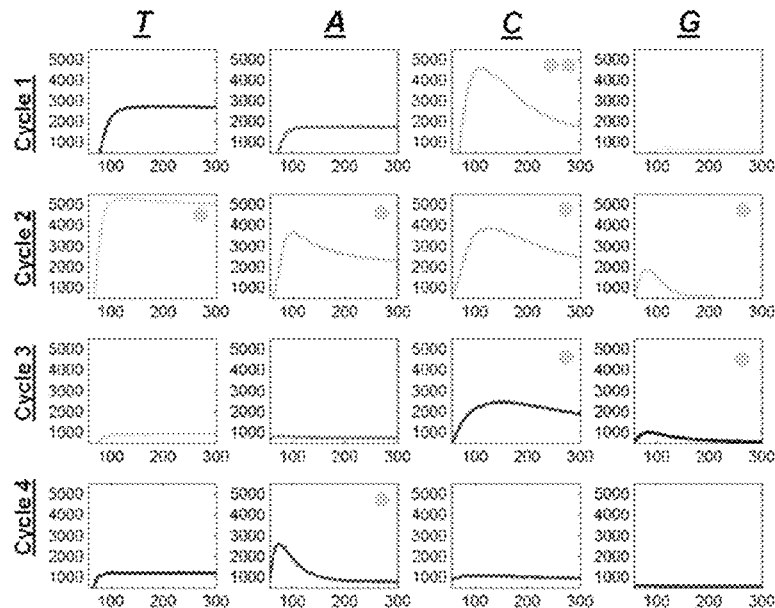
FIG. 15 shows kinetic plots for binding of polymerase to a nucleic acid in the presence of various nucleotides and sequences derived from the kinetic plots.

The kinetic plots detected for each flow are shown in FIG. 15. Filled dots shown in the upper right corner of some plots in FIG. 15 indicate that those flows produced a kinetic plot that was indicative of correct nucleotide incorporation. In one flow (flow 3 of cycle 1), the kinetic profile was indicative of two incorporation events as indicated by two filled dots. The sequence CCTACGCGA was determined from the order of the flows for which incorporation was detected. The sequence correctly corresponded to the first 9 bases of the region of the C2cal template that was extended (as indicated by the underlined portion of the template above).

EXAMPLE VI

Ensemble-Level Detection of Labeled Nucleotide Incorporation Using Pre-Equilibrium Kinetics Incorporation of labeled nucleotides into DNA clusters was detected using a Genome Analyzer (GA) from Illumina, Inc. (San Diego, Calif.). GA flow cells were prepared according to the manufacturer's instructions with the following details and exceptions. GA flow cells were hybridized to Broad Template 3 and cluster amplification was performed according to the manufacturer's instructions to produce features on the surface of the flow cell having the Broad Template 3 sequence. The resulting flow surface contained a monotemplate field of features for which the first insertion base was "T".

Figure 16:
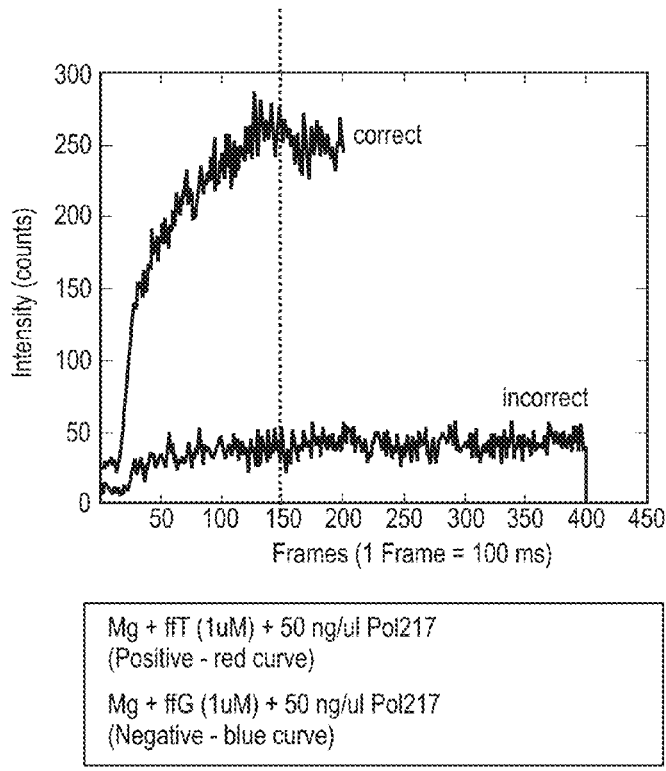
FIG. 16 shows kinetic plots for binding of polymerase to a nucleic acid in the presence of correctly matched and mismatched nucleotides.

Detection of the monotemplate bearing flow cell was carried out on the GA according to the manufacturer's instructions with the following details and exceptions. Imaging was performed in real-time, such that image acquisition rate was 8 frames/sec. Reaction mix for the sequencing reaction was created in standard IMX buffer with the following components 50 ng/µl Pol217 and 1 µM of fully functional T nucleotide for the positive control lane (upper curve, FIG. 16) and 1 µM of fully functional G nucleotide (lower curve, FIG. 16). Reactions were carried out at room temperature.

EXAMPLE VII

Comparison of Kinetic Properties Between Polymerases

The pre-steady kinetic analysis of Klenow or KlenTaq polymerase for incorporating the cognate nucleotide (dGTP) was monitored following the mixing of 6-carboxyfluorescein (6-FAM) dye label hairpin-DNA template with the enzyme (600 nM) and nucleotide (100 µM) in a reaction buffer containing 50 mM Tris-HCl, pH 7.5, 300 mM NaCl (or 50 mM NaCl in the KlenTaq reaction), 0.5 mM Dithiothreitol and 5 mM MgCl$_2$ (or 2 mM MgCl$_2$ in the KlentTaq reaction) in an Applied Photophysics SX20 stopped-flow spectrometer. The 6-FAM hairpin-DNA template was: 5'-CGTTAGTAACCTC-G.AGGCAACTTAGCCT(6-FAM) CGAG-3' (SEQ ID NO: 5).

Figure 17:
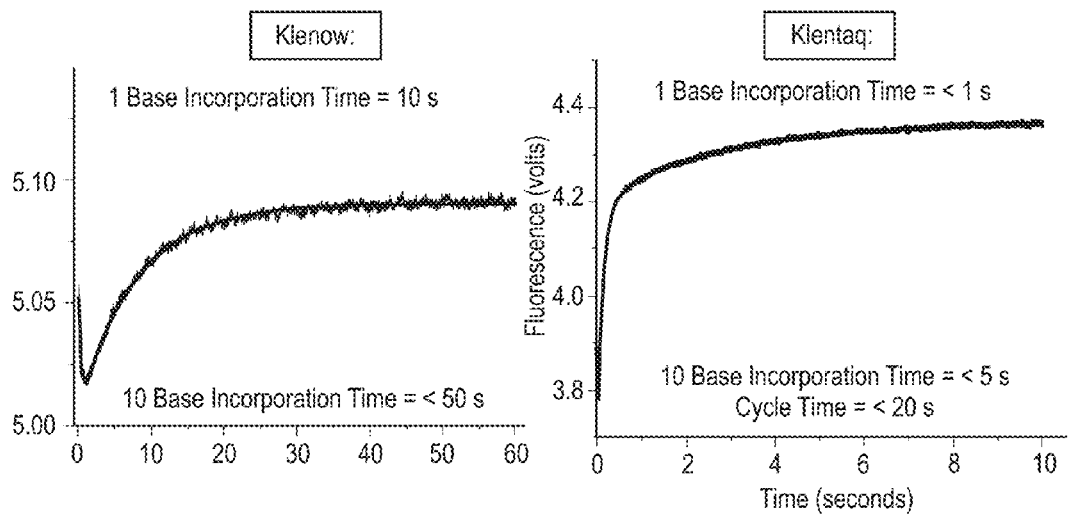
FIG. 17 shows stopped flow kinetic traces for two polymerases with kinetic properties that have similar simulation properties.

As shown in FIG. 17, the mixing of 6-FAM dye label hairpin-DNA template with the Klenow polymerase (right panel) or KlenTaq polymerase (left panel) and nucleotide showed a rapid 6-FAM dye fluorescence quenching followed by a slower fluorescence recovery. The rate of fluorescence quenching and recovery represents the association rate of the polymerase binding to the nucleic acids in the presence of the nucleotide and dissociation rate of the polymerase from the nucleic acids, respectively. These two rates can be extrapolated by fitting the fluorescent time trace to a double exponential equation: $F=A_1*(1-e^{-k_1^* r})+A_2*(1-e^{-k_{-1}^* r})$ to yield two rate constants, $k_1$ and $k_{-1}$, respectively. The value of $k_1$ for Klenow and KlenTaq are 2.41±0.03 s$^{-1}$ and 31.11±0.34 s$^{-1}$, respectively. The value of $k_{-1}$ for Klenow and KlenTaq are 0.15±0.001 s$^{-1}$ and 0.67±0.001 s$^{-1}$, respectively. From this data it was determined that KlenTaq has a better association rate for binding to the nucleic acids in the presence of the cognate nucleotide and dissociation rate from the nucleic acids as compared to Klenow.

Figure 18:
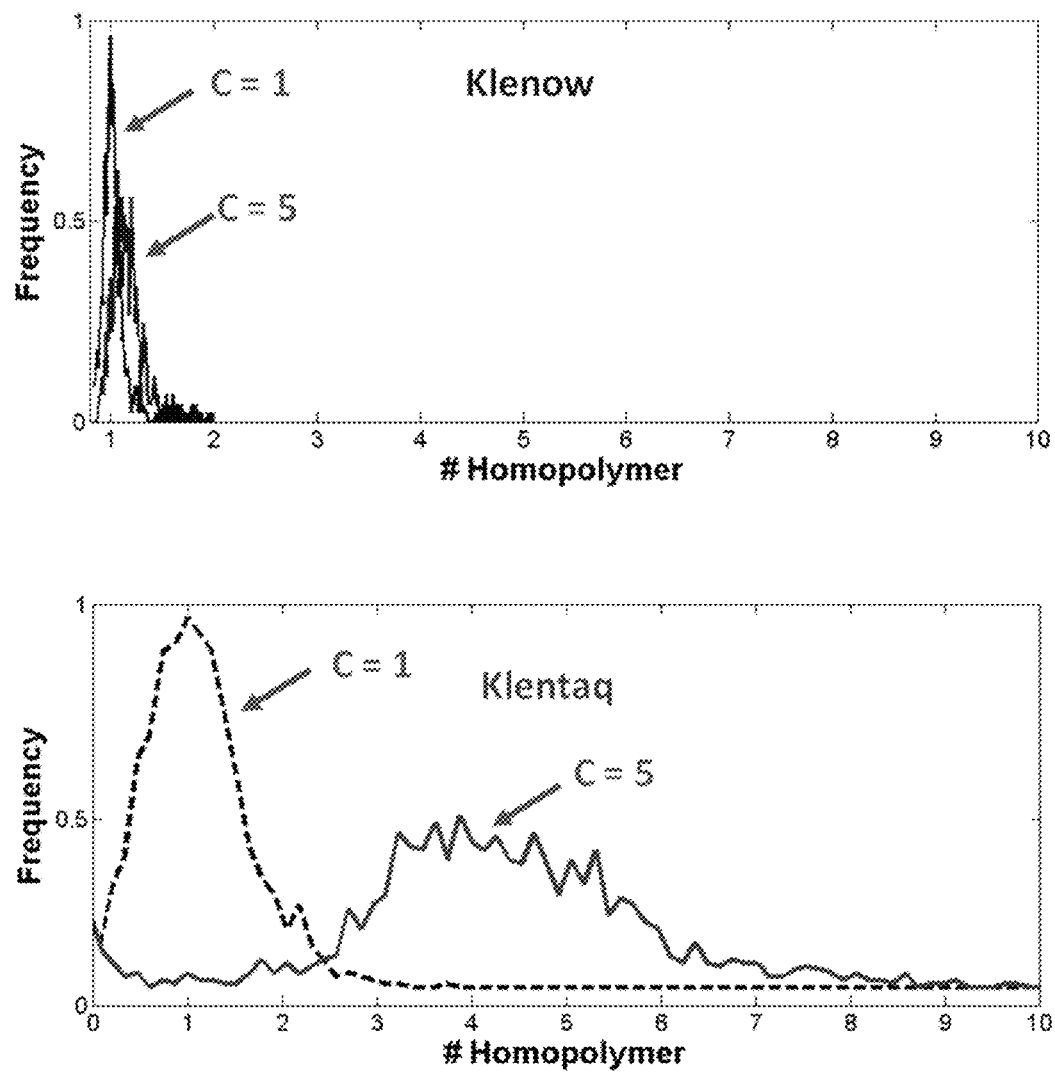
FIG. 18 shows homopolymer discrimination results for incorporation reactions with two different polymerases.

A comparison of homopolymer detection by Klenow polymerase and Klentaq polymerase is shown in FIG. 18. Experiments performed for either polymerase used the following template (C5: AATGATACGGCGACCACCGAGATCTA-CACTCTTTCCCTACACGACGCTCTTC CGATCT CCCCCTACGCATCTCGTATGCCGTCTTCTGCTTG (SEQ ID NO: 6)). The region of the template that was sequenced is underlined.

Klenow sequencing used the following conditions: Polymerase reaction buffer was prepared from the following: 50 mM ACES pH pH 7.4; 300 mM NaCl; 5 mM DTT; 5 mM MgSO4; 2.5 mM 2-nitrobenzoic acid; 0.02% Tween 20. For sequencing, the Cy3 labeled Klenow polymerase was diluted to 150 nM in the polymerase reaction buffer and dCTP concentration was 100 µM. High salt wash buffer was composed of 50 mM Tris-HCl pH 7.5; 1 M NaCl; 0.02% Tween 20. Using a synchronized sequencing scheme (one nucleotide delivered at a time), the following flows were repeated: (1) dNTP; (2) High Salt wash; (3) pre-wash with polymerase extension buffer. Sequencing reactions were done at RT.

Klentaq sequencing used the following conditions: polymerase reaction buffer was prepared from the following: 50 mM ACES pH pH 7.4; 100 mM NaCl; 5 mM DTT; 5 mM MgSO4; 2.5 mM 2-nitrobenzoic acid; 0.02% Tween 20. The Cy3 labeled Klentaq polymerase was diluted to 75 nM in the polymerase reaction buffer and dCTP concentration was 100 µM. High salt wash buffer was composed of 50 mM Tris-HCl pH 7.5; 1 M NaCl; 0.02% Tween 20. Using a synchronized sequencing scheme (one nucleotide delivered at a time), the following flows were repeated: (1) dNTP; (2) High Salt wash; (3) pre-wash with polymerase extension buffer. Sequencing reactions were done at 45° C.

The results of FIG. 18 show that Klentaq provided superior resolution of homopolymers compared to Klenow under the conditions tested. Specifically, in the Klentaq plot, the signals obtained from the region of the template having a homopolymeric run of 5 C nucleotides (C=5, solid line) can be readily discerned from the signals obtained from the single c nucleotide (C=1, dashed line). In contrast, although the C=5 signals are distinct from the C=1 signals in the Klenow plot, there is substantial overlap.

EXAMPLE VIII

Algorithms for Deriving Sequence Information from Pre-Equilibrium Kinetics Data

This example describes methods for deriving sequence information from real or simulated data obtained in pre-equilibrium detection conditions. The methods can be utilized for the model described in Example VIII of U.S. Provisional Application No. 61/578,684. However, the methods can be used for other models and are thus set forth generally below.

Using stopped-flow methods, solutions containing fluorophore labeled polymerase and nucleotides are mixed with target nucleic acids that are attached at features of an array. Pre-equilibrium data is provided as a series of frames each containing a fluorescence image of the array. Fluorescence amplitude at each feature of the array is extracted from each frame, generating a time series. The amplitude of the signal at each feature is proportional to the number of fluorophore molecules present at the feature. Depending on the presence of correct nucleotide, this time series has different characteristic shape.

Depending on whether the nucleic acids in a feature are extended, and how many nucleotides are added by the extension, each feature goes through a number of transient state(s), until a mismatch base is reached. In the end the system reaches an equilibrium (steady state).

A parametric model based method or an ad-hoc measurement method can be used in the detection. Each is described below.

Parametric model based method

In an ideal setup, the enzyme and nucleotide concentrations are much higher than the effective concentration of nucleic acid in a feature of the array. Thus, there is very little depletion of polymerase and nucleotide. In addition, the flow rate is very high so that the introduction of reaction components is assumed to be instantaneous. Under these assumptions, $d[E]/dt \sim 0$ and $d[dNTP]/dt \sim 0$. In addition, very little reverse reaction happens, so $k_{-1}=0$.

A zero vs. one (binary) base call is made as follows. The recorded fluorescence signal over time is fit to an appropriate reaction model. A base call is made depending on the initial concentrations, depending on which solution gives a better fit to the data.

Figure 20:
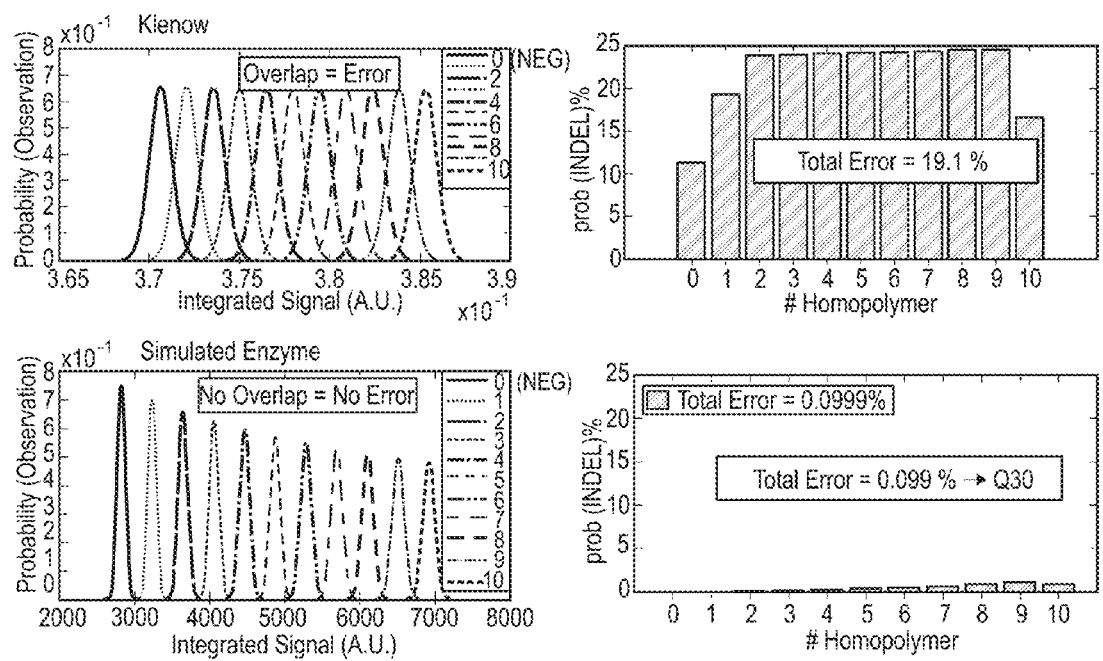
FIG. 20 shows simulation of signals detected for pre-equilibrium kinetic analysis of polymerase transient states for discrimination of homopolymer length.

Base calls in a homopolymer are made as follows. When the polymerase extends a homopolymer region of length N, each template in a cluster goes through N steps of chemistry before it reaches the steady state (i.e. equilibrium). Under the assumption of significantly higher nucleotide concentration, the model can be modified. A fitting process produces a corresponding homopolymer count. FIG. 20 shows an example of simulation homopolymer discrimination using different kinetic rates. Assumptions made in Klenow simulation of FIG. 20 (upper panel) are as follows: 1000 templates, 200 photons detected per second per dye, 50 ms positive binding duration, 38 ms negative binding duration, 60 ms off duration, and 200K background. The lower panel results showed improved accuracy with improved enzyme kinetics and experimental conditions. The results are generated with the following assumptions: 1000 templates, 200 photons detected per second per dye, 5 ms positive binding duration, 0.5 ms negative binding duration, 6 ms off duration, and 10 K background (overall signal integration time is 10× faster).

In a continuous sequencing situation, incorporation kinetics are assumed to remain relatively consistent from cycle to cycle. Similar assumptions are made about other parameters such as number of templates in a feature. Based on these assumptions, constraints are optionally introduced in the fitting process. These constraints improve the accuracy of the base call, especially homopolymer base calling. In addition, it provides a real time monitoring mechanism of data quality.

Error estimation is carried out as follows. At each time t, the amplitude of the observation is viewed as a random variable P. The distribution of P depends on the reaction kinetics and total number of template. The distribution of P is used in the fitting process to improve accuracy using, for example, a maximum likelihood approach. In addition, this is used in the kinetics monitoring process. In a simplified method, the distribution of P is approximated with a Gaussian distribution. The variance of the measurement is used as an additional signal in the fitting and monitoring process.

Under non-ideal flow conditions, diffusion steps produce a temporal concentration change for reaction components that can potentially be significantly slower than the ideal flow. Thus, concentration of polymerase enzyme [E] can become a function of time. A background trace for each feature is extracted from the movie (i.e. the series of images) at pixels close to the foreground pixels. The amplitude of the background pixel corresponds to the concentration of fluorophore. For example, if the polymerase is labeled, background amplitude is proportional to the polymerase concentration. This information is used in solving equations appropriate to the model, which provides a method of basecalling under non-ideal flow situation.

Figure 21:
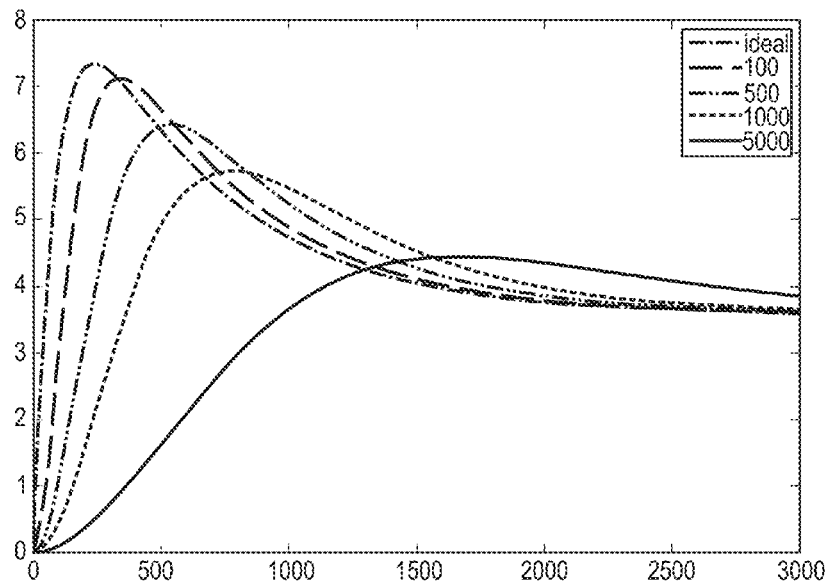
FIG. 21 shows simulation results of an incorporation reaction under different flow speeds.

FIG. 21 shows simulation result of an incorporation reaction under different flow speed, in which bigger numbers indicates slower flow and the "ideal" curve corresponds to instant flow.

Signal Integration Method

In the signal integration method, signals collected from each feature are integrated over time. This sum is compared to a look up table to make a basecall. Depending on the model used, this integrated signal can be proportional to the number of incorporated bases. The lookup table can be either predetermined or adjusted for each feature as the sequencing reaction progresses.

Ad-hoc Method

In the ad-hoc method, signal waveforms are fit to an ad-hoc form (e.g., a polynomial function). A pre-calibration chemistry step is used to establish the polynomial coefficients for each of the reactions (0-mer, 1-mer, 2-mer, ... ) and each base (A,T,C, and G). The signal is fit with each set of the coefficients. Basecalls are made by choosing the coefficients which give the least fitting error.

EXAMPLE IX

DNA Sequencing Method Using DNA Binding Kinetics

This example demonstrates sequencing of nucleic acid templates using differences in polymerase binding kinetics to distinguish incorporation of different nucleotides into a nascent polynucleotide being extended by the polymerase along the templates.

Results

Base Discrimination Using Enzyme/DNA Binding Kinetics: Model

The binding of labeled polymerase to immobilized DNA clusters was monitored, whereby the emission signal was detected from the labeled Enzyme/DNA complex formation. For the concept of sequencing using pre-steady DNA binding kinetics, the simplified kinetic model shown in FIG. 1 and described herein with respect to Equations 1 through 5 was used.

Base Discrimination Using Enzyme/DNA Binding Kinetics: Bulk Measurements

Experiments measuring nucleotide concentration dependence of product formation under high salt conditions for a model enzyme/DNA system were performed using quenched flow measurements. Increasing concentrations of correct (dCTP) or mismatch (dATP) nucleotides were rapidly mixed with BSU polymerase and 19/36 mer in 300 mM NaCl buffer.

Figure 23:
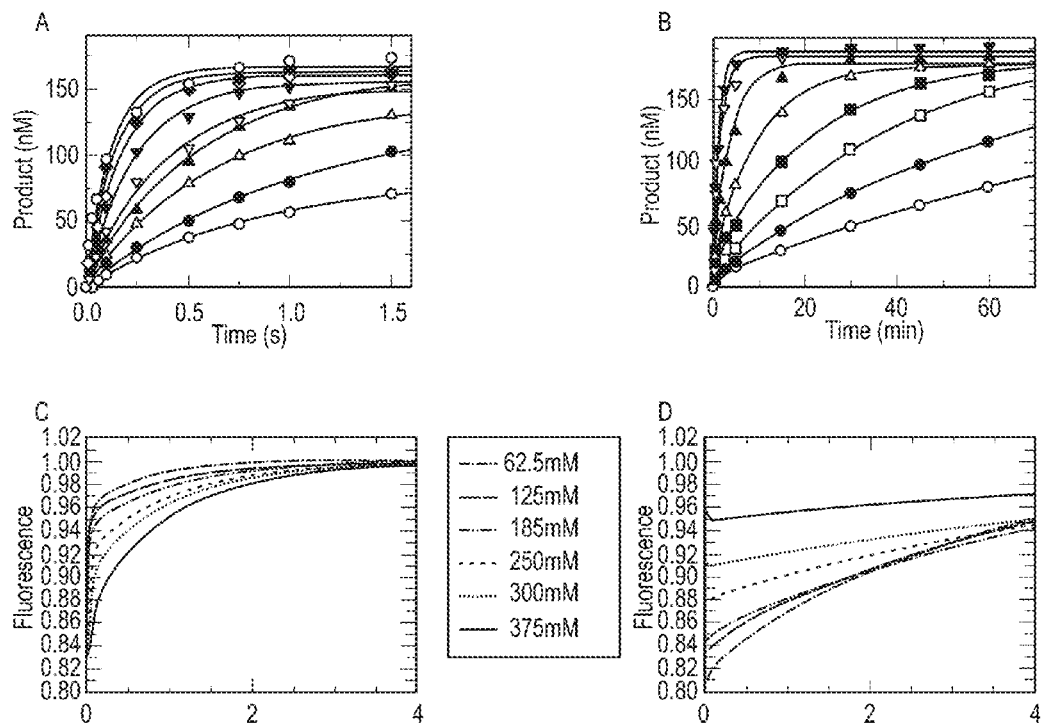
FIG. 23 shows quench-flow nucleotide concentration dependence of product formation under high salt conditions. Increasing concentrations of (a) correct (dCTP) or (b) mismatch (dATP) nucleotides were rapidly mixed with BSU polymerase and 19/36 mer in 300 mM NaCl buffer. The resulting time dependence of product formation for each nucleotide concentration was fit to a single exponential equation to obtain a rate. Stopped flow nucleotide-induced fluorescence response shows NaCl concentration dependence for (c) correct (dCTP) and (d) mismatch (dATP) nucleotides that were rapidly mixed with BSU polymerase and FAM labeled 19/36 mer in the presence of various NaCl concentrations. An increase in NaCl resulted in increased fluorescence response for the correct nucleotide and decreased response for the mismatch.
Figure 24:
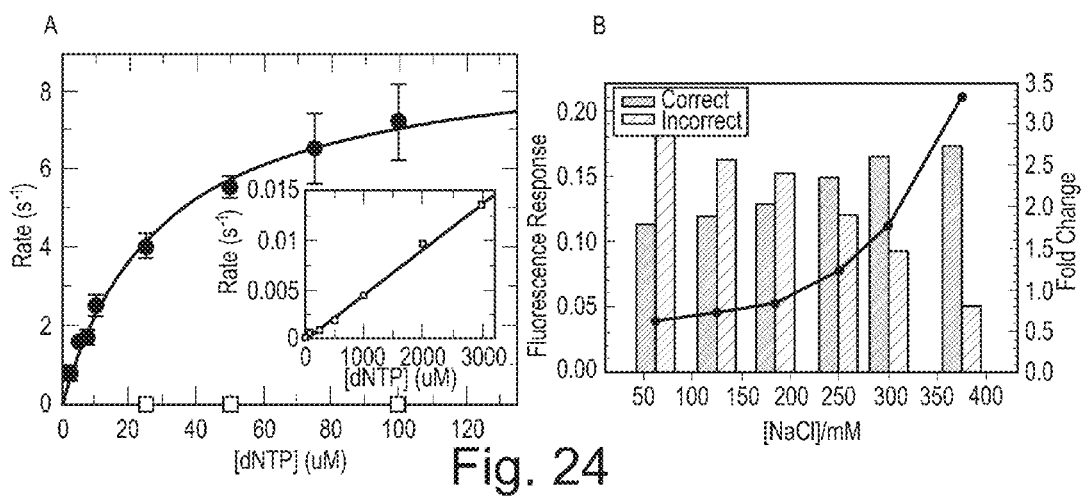
FIG. 24 shows (a) quench-flow nucleotide concentration dependence of product formation under high salt conditions. Time dependence of product formation for each nucleotide concentration was fit to a single exponential equation to obtain a rate for correct (●) and mismatch (□) product formation. (b) Stopped-flow nucleotide-induced fluorescence response shows NaCl concentration dependence for correct (dCTP, left bar in each pair of bars) and mismatch (dATP, right bar in each pair of bars) nucleotides. The net result of a NaCl dependent 5.3-fold increase (●) in correct signal versus mismatch from 62.5 mM to 375 mM NaCl is shown.

The resulting time dependence of product formation for each nucleotide concentration was fit to a single exponential equation to obtain a rate (FIG. 23). The nucleotide concentration dependence of the obtained rates for correct (●) and mismatch (□) product formation were fit to a hyperbolic equation to derive values of 9.15±0.4 s$^{-1}$ and 29.1±2.9 µM for k$_{pol,dCTP}$ and K$_{d,app,dCTP}$, respectively (FIG. 24A). These values result in a specificity constant (k$_{pol}$/K$_{d,app}$=k$_{cat}$/K$_m$) for the correct nucleotide of 3.1±0.1×10$^{-1}$. The nucleotide concentration dependence on the rate of mismatch incorporation could not be saturated due to experimental limitations on nucleotide concentrations. The resulting nucleotide concentration dependence of the observed rates were fit to a linear equation with a slope (corresponding to the specificity constant) of 4.6±0.1×10$^{-6}$ µM$^{-1}$s$^{-1}$. The specificity constants for correct and mismatched nucleotides were used to calculate a discrimination value of 6.6±0.3×10$^4$ in high NaCl conditions. In addition to providing an estimated apparent K$_d$ for the nucleotides under higher ionic strength, these measurements also demonstrate that high specificity under these conditions is maintained, which is generally desired for any sequencing technology.

Theoretically, it was possible to use an enzyme simulation that predicts the feasibility of correct vs. mismatch base discrimination using enzyme-DNA binding kinetics. In the simulation, it is assumed that mixing is an instantaneous event and does not factor into the simulated results, but to explore the efficacy of DNA/binding kinetics for base discrimination, mixing reacting species is done. Rapid mixing is generally achieved using a fast delivery and mixing system to minimize the contribution of the diffusion constants to the overall access of the polymerase to the DNA templates. To determine the validity of the theoretical predictions for base discrimination based on DNA binding kinetics, correct (dCTP) and mismatch (dATP) nucleotides were rapidly mixed with BSU polymerase and FAM labeled 19/36 mer in the presence of various NaCl concentrations with a stopped flow instrument. Pre-steady state correct and mismatch nucleotide kinetic responses of polymerase/DNA binding were made by monitoring the extent of induced fluorescence quenching response. Correct and mismatch nucleotide responses were determined from the stopped flow kinetic raw traces (FIG. 23). The traces were normalized and the maximum fluorescence change was determined and subsequently, correlated with the extent of synchronized enzyme-DNA binding. As [NaCl] was increased and the nucleotide concentration was held constant, the fluorescence change for the correct nucleotide (leftmost bar in each pair of bars in FIG. 24B) was increased, while the response for the mismatch (rightmost bar in each pair of bars in FIG. 24B) was decreased. The net result is a [NaCl] dependent 3.5-fold increase (●) in correct signal versus mismatch from 62.5 mM to 375 mM [NaCl] (FIG. 24B).

Base Discrimination Using Enzyme/DNA Binding Kinetics: DNA Clusters

Figure 25:
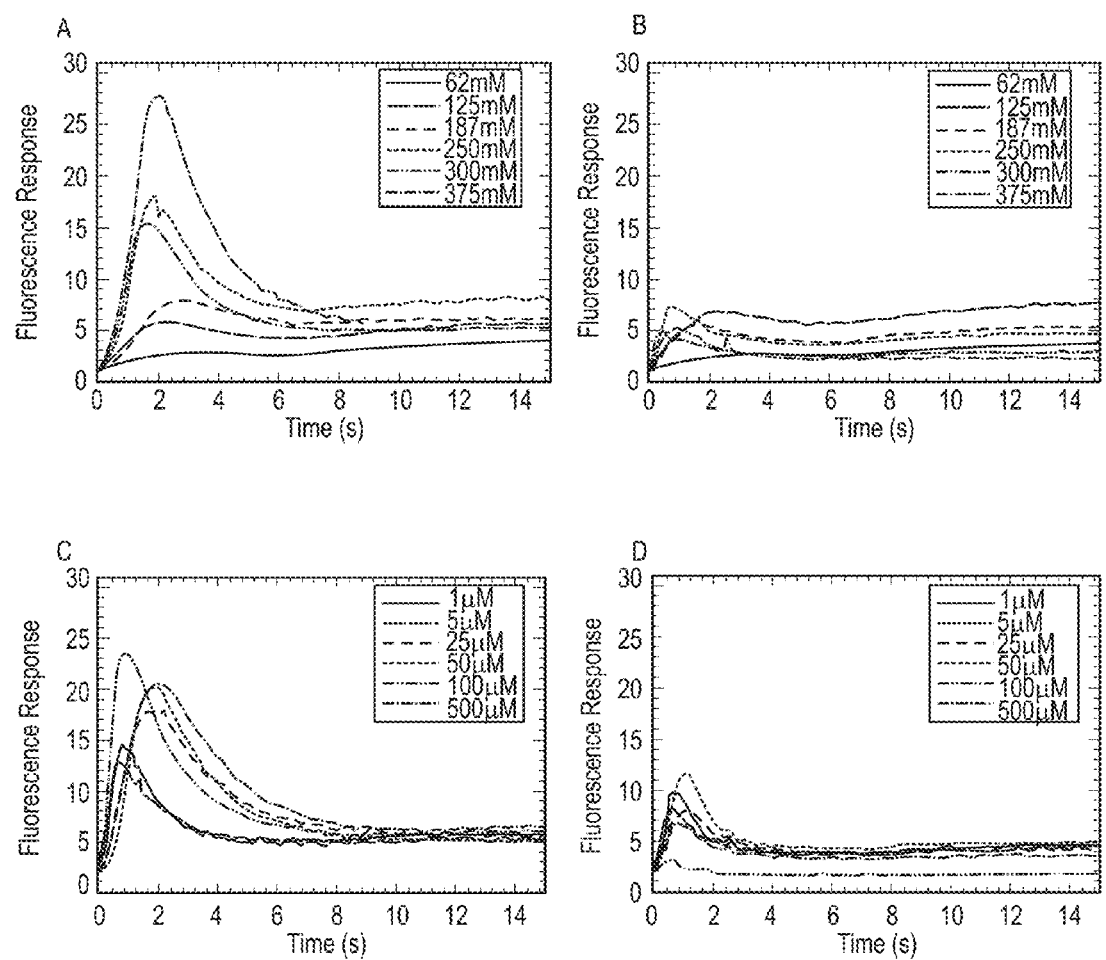
FIG. 25 shows that in the presence of varying NaCl concentrations (a-b) or dNTP concentrations (c-d), correct (dCTP) and (b,d) mismatch (dGTP) nucleotides and 200 nM BSU polymerase were introduced into a clustered flow cell that had underwent cluster amplification. Resultant time traces were background subtracted.
Figure 26:
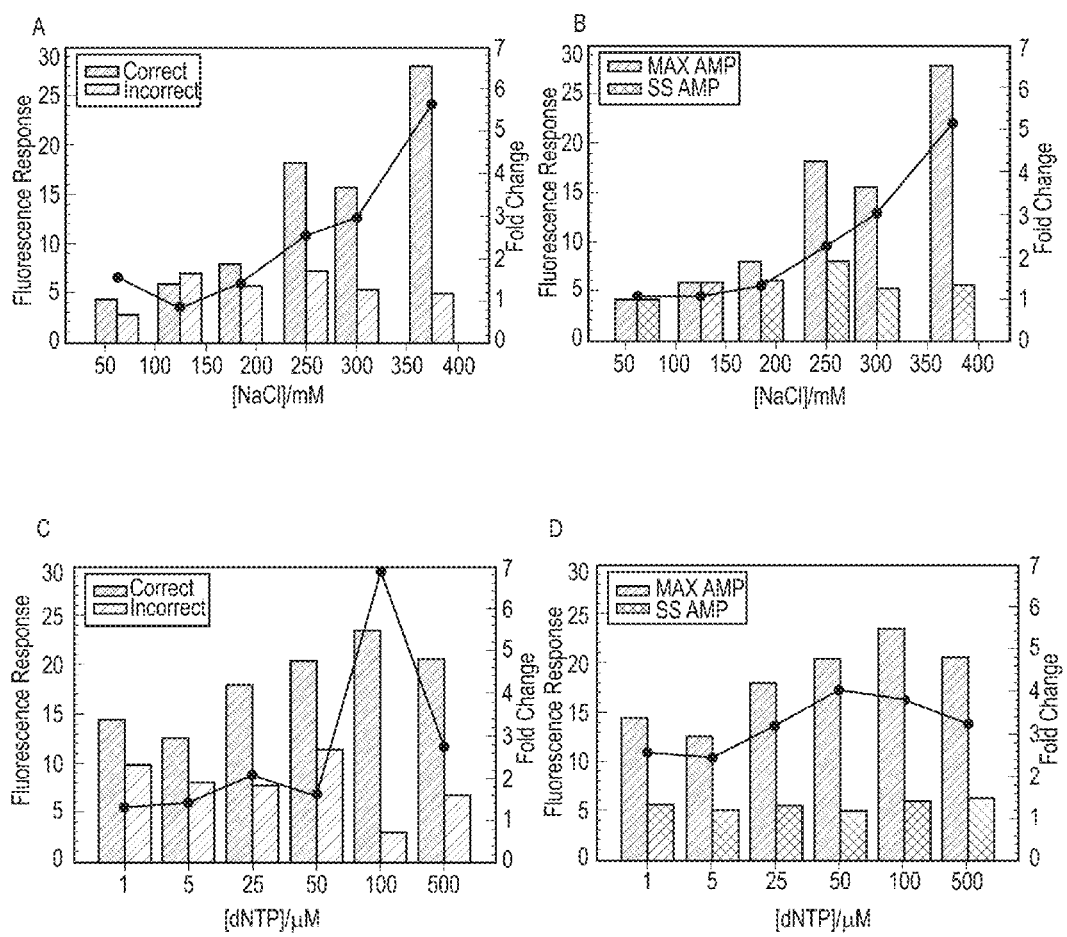
FIG. 26 shows correct (dCTP) and mismatch (dGTP) nucleotides and 200 nM BSU polymerase in the presence of various NaCl concentrations (a) or various dNTP concentrations (c) introduced into a cluster-bearing flow cell. Resultant time traces were background subtracted. The maximum amplitude was obtained from the peak intensity of the time trace while the steady state amplitude was the average intensity of the steady state amplitude. The ratio of the MAX AMP (leftmost bar in each pair of bars) to SS AMP (rightmost bar in each pair of bars) is shown for both (b) salt and (d) nucleotide titration data.

Since the stopped flow sample chamber can be approximated as a three dimensional volume, the mixing times are relatively short. As was previously mentioned, the extent of signal above background is governed by factors, such as mixing. When moving to a flow cell and DNA immobilized on a substrate, the reactants are introduced in a way to insure the best possible synchronization of Enzyme/DNA complex formation within individual DNA clusters. While it was possible to demonstrate the ability to discriminate correct signal versus mismatch under high ionic strength and nucleotide concentrations in a 3D volume, the genome analyzer (GA, Illumina Inc., San Diego Calif.) sample flow cell mixing dimensions are more complex. To test the efficacy of combining Illumina cluster technology with detection of enzyme/DNA binding kinetics to create a sequencing methodology, a flow cell was seeded with a single DNA template species and clusters grown from the template, whereby the first correct incorporation base for a template hybridized sequencing primer was a dCTP. Relying on the quenched flow data (FIG. 24A), the nucleotide concentration was fixed at 100 µM and a salt titration was performed similar to that previously described in bulk (FIG. 24B). Upon introduction of the correct or mismatch nucleotide with labeled BSU polymerase over a range of [NaCl] of 62-375 mM, the time dependent signal responses were recorded and extracted for each of the individual GA clusters (FIG. 25). Within these individual cluster responses, there exists a certain amount of amplitude variability due to variability in the template number per cluster. While across a field, this introduces significant kinetic variability, it is possible to correct for this in a cluster dependent manner using an upfront calibration sequence. Using data from clusters that had peak amplitudes for the first base incorporation that were within 10% of each other, it was possible to implement a simple correction for this variability. After averaging time traces for 200 clusters a single ROI of the correct and mismatch nucleotide responses were determined from the raw traces over a range of [NaCl] of 62-375 mM (FIG. 25). The maximum amplitudes from the correct and mismatch traces are ascribed to the extent of synchronized enzyme-DNA binding. Similar to the stopped flow data results, as [NaCl] was increased and the nucleotide concentration was held constant, the fluorescence change for the correct nucleotide (leftmost bar in each pair of bars in FIG. 26A) was increased, while the response for the mismatch (rightmost bar in each pair of bars in FIG. 26A) was decreased. The net result is a [NaCl] dependent 6-fold increase (●) in correct signal versus mismatch from 62.5 mM to 375 mM [NaCl]. These results confirmed that it is feasible to perform correct vs. mismatch base discrimination using immobilized DNA clusters in a flow cell and enzyme/DNA binding kinetics.

In addition to revealing the discrimination power of the chemistry, the correct time traces also can provide further information regarding homopolymer detection. Homopolymer detection is one of the major challenges of synchronized sequencing methods, for example, those performed by pyrosequencing. Pyrosequencing detects the pyrophosphate product of a primer extension reaction, and the signal detected is assumed to be directly proportional to the amount of pyrophosphate released. However in pyrosequencing, the amount of signal does not always scale linearly with the number of nucleotides in a homopolymeric sequence region.

With the sequencing approach of the present Example, multiple parameters can be correlated with homopolymer detection such as maximum amplitude, integrated signal, and enzyme kinetic parameters that can be extracted by fitting the data to a kinetic model. If the integrated approach of the present example is implemented for homopolymer discrimination, it is important for the reaction to return to equilibrium or a steady state prior to the completion of image collection. The steady state amplitude represents the residual signal that remains after the introduction of the reaction mixture to the flow cell. In the best case scenario, the state steady amplitude returns to background. In order to perform a qualitative measure of homopolymer discrimination using this method, the maximum fluorescence amplitude response for the correct nucleotide (leftmost bar in each pair of bars in FIG. 26B) and the steady state amplitude response (rightmost bar in each pair of bars in FIG. 26B) are plotted. The net result is a [NaCl] dependent 6-fold increase (●) in maximum versus steady-state amplitude response. These results demonstrated that it is feasible to perform correct vs. mismatch base discrimination using immobilized DNA clusters in a flow cell and enzyme/DNA binding kinetics.

The simulations combined high nucleotide concentration and ionic strength to create correct vs. mismatch base discrimination. Following this strategy, nucleotide titrations were performed to determine the dependency of correct versus mismatch discrimination and max amplitude versus steady state on [dNTP]. Correct or mismatch nucleotide was introduced with labeled BSU polymerase and a range of [dNTP] of 5-500 µM. the time dependent signal responses were recorded and extracted for each of the individual GA clusters (FIG. 25). At elevated concentrations of [dNTP], the maximum amplitude of the correct nucleotide (leftmost bar in each pair of bars in FIG. 26C) versus the mismatch response (rightmost bar in each pair of bars in FIG. 26C) increased until the nucleotide concentration was titrated above 100 µM. At higher nucleotide concentrations, the discrimination begins to drop, which may be a result of misincorporation of the mismatch base. The net result is a [dNTP] dependent >6-fold increase (●) in correct signal versus mismatch for [dNTP] =100 µM. With increasing [dNTP], the ratio of the maximum fluorescence amplitude response for the correct nucleotide (leftmost bar in each pair of bars in FIG. 26D) and the steady state amplitude response (rightmost bar in each pair of bars in FIG. 26D) reached a maximum between 50 and 100 µM. The net result is a [dNTP] dependent 4-fold increase (●) in maximum versus steady-state amplitude response. At higher [dNTP], misincorporation can also inhibit the DNA off rate for the polymerase, yielding higher background or increased steady state amplitude. The net result is a [NaCl] dependent 6-fold increase (●) in maximum versus steady-state amplitude response.

Base Discrimination Using Enzyme/DNA Binding Kinetics: DNA Sequencing

Both theoretical kinetics (Equations 3 through 5) and simulation studies suggest that the number of photons emitted from a cluster is directly correlated to the number of nucleotides incorporated at a certain flow. The more nucleotides incorporated into the DNA templates, the longer is the dwell time of the polymerase, and more photons are observed at the cluster. This observation suggests the integrated photon counts at a cluster can be used as a basecalling feature. On the other hand, integrated photon counts at a cluster depend also on the number of templates in that cluster, i.e., the more templates equals brighter signal. This dependency can be removed by normalizing the signal by a direct indicator of the template number. The basecalling feature and normalized integrated counts are computed by removing the DC bias by subtracting off average intensities before each flow. The average intensity is computed by averaging intensities at the first 40 frames. Secondly, cluster intensities are integrated between a time window, i.e. the first 150 frames for G and A flows, the first 200 frames for C and the first 350 frames for T. The differences in the integration time are likely related to incorporation speed difference between the bases. At last, the cluster integrated counts are normalized by the sum integrated counts of certain flows.

Figure 27:
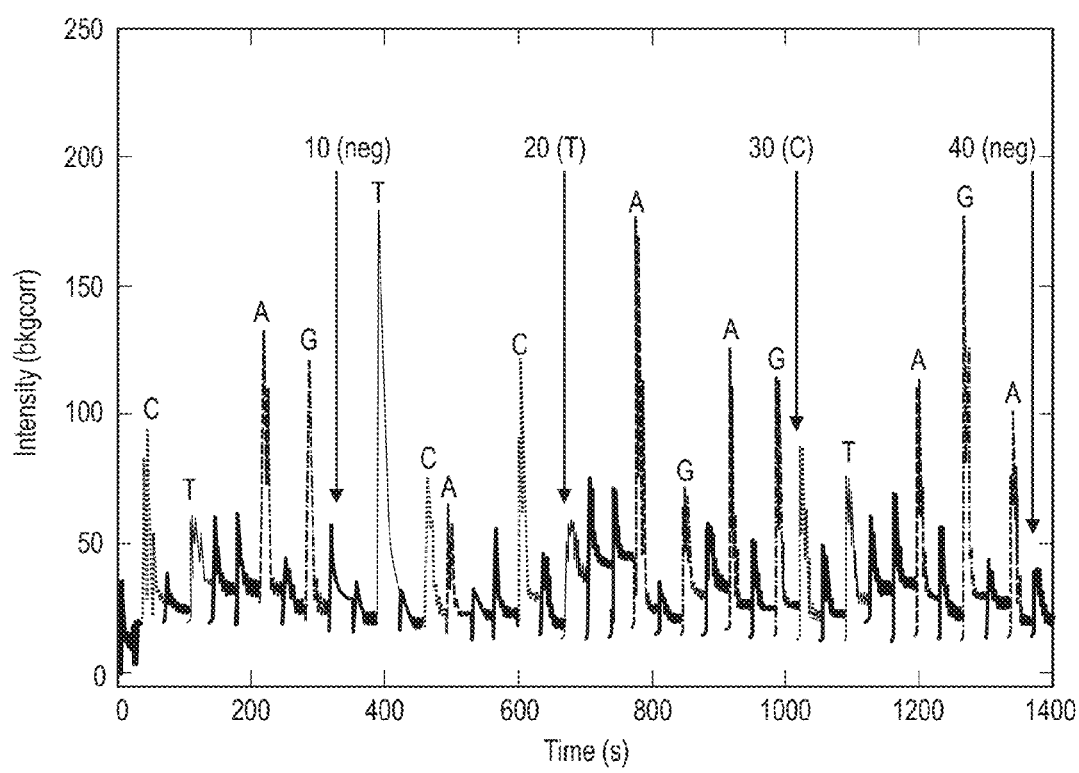
FIG. 27 shows time trace examples for sequencing of a synthetic template.

FIG. 27 shows the results of a sequencing reaction carried out on the modified GA instrument as described below in the materials and methods section. Flows 10, 20, 30 and 40 are indicated by the arrows. Flows resulting in a base call of Adenine, Cytosine, Thymine or Guanine are indicated with A, C, T or G, respectively. Negative flows are unlabelled (with the exception of flows 10 and 40).

Figure 28:
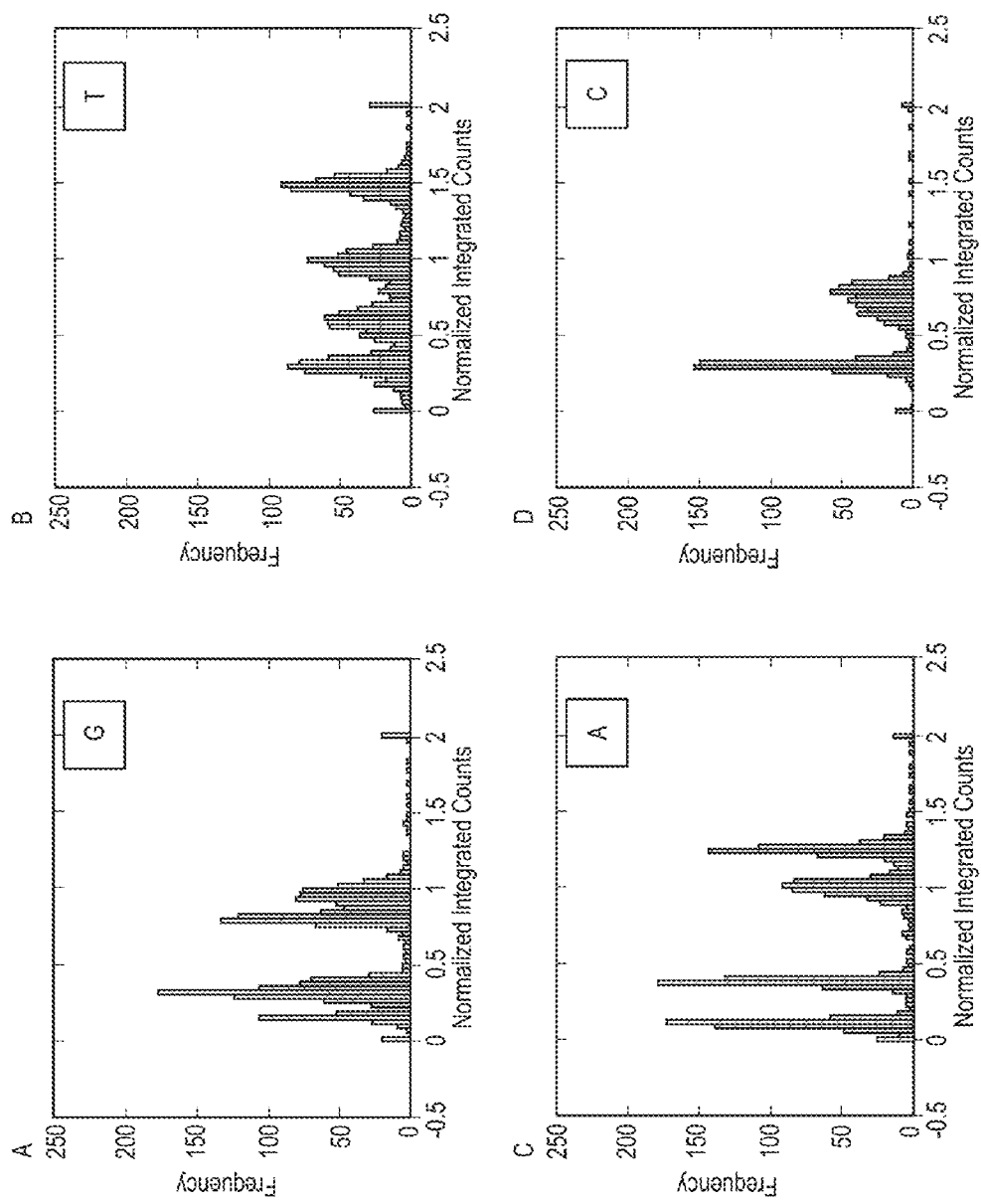
FIG. 28 shows (A) histograms of G homopolymer repeats, which correspond to homopolymer repeats of 0, 1, 2, and 3-mers, respectively; (B) histograms of T homopolymer repeats, which correspond to homopolymer repeats of 1, 0, 5, and 2-mers, respectively; (C) histograms of A homopolymer repeats, which correspond to homopolymer repeats of 0, 2, 1, and 3-mers, respectively; and (D) histograms of C homopolymer repeats, which correspond to homopolymer repeats of 0, and 1-mers respectively.

Homopolymer discrimination is also possible using the sequencing method set forth herein. For purposes of demonstration, flow 7, 12, 20, 23, and 32 were chosen, because these flows included a significant number of homopolymers, and thus the sum of all these flows is a more robust estimation of the cluster template numbers. This step can be achieved in inhomogeneous template sequencing by including a "calibration" sequence at the beginning of each template. Homopolymer discrimination was demonstrated for individual bases by plotting histograms of the integrated counts that were extracted from each of the clusters with flow numbers that corresponded to homopolymer repeats (FIG. 28). Thresholds are chosen using a K-means method to discriminate between multiple clusters. A hypothesis that each cluster of the normalized integrated counts represents a homopolymer number was tested by attempting a basecall process at each cluster independently. For all 451 clusters in the FOV, compared to the known template, 251 clusters generated perfect sequencing reads at the first 11 bases (14 flows). At the first 16 bases (24 flows), 245 clusters generated sequence reads with 0 or 1 error. Deeper analysis revealed that all the errors were from a single flow.

While this example provides a proof of concept for this sequencing chemistry, there are some straightforward methods that can be used to improve the sequencing metrics. Since base discrimination for this chemistry utilizes polymerase-DNA binding kinetics, factors that introduce variability into the binding kinetics can be used to adjust the accuracy of base calling. Some factors that may impact enzyme/DNA binding kinetics include, for example, DNA secondary structure, template number/clusters, and fluidics.

In the presence of the regions of complex secondary structure, it is likely that the enzyme kinetics for the polymerase would be affected for both the correct and incorrect nucleotide. The averaged traces for both the negative and positive flows of like bases show some of this variability. While this introduces variability across the data, enough data collected over time is expected to reveal patterns that could help to reduce apparent variability and may also be implemented as a secondary base calling algorithm if the pattern is robust and reproducible. Thus, Bayesian learning algorithms can be implemented to assist in base calling. Template number/cluster also directly impacts both the amplitude of the response and also potentially the enzyme/DNA off rates. The packing density of templates within clusters may be difficult to quantify in some instances which could in turn lead to enzyme/kinetic profiles that are difficult to resolve. Calibration sequences can be included as part of the adapter sequences used to immobilize the DNA template to the substrate. These calibration sequences can be used to estimate template density and subsequently correct kinetic constants to potentially remove the potential kinetic variability that may arise from template variability.

Additional adjustments to address issues that may arise from secondary structure or template density variability include, for example, increased temperature, formulations improvements, substrate modifications, and/or polymerase engineering strategies. The proof-of-concept for this sequencing chemistry was achieved by using wild type BSU polymerase and modifying the formulation conditions to achieve correct/mismatch base discrimination. As it has been shown numerous times, polymerase can be successfully engineered to improve its native performance. Moving forward, a polymerase engineering project could address some of the sequence context questions. Also, it would be possible to understand more completely potential mutations that might impact DNA translocation and off rates to find mutants with improved homopolymer calling. By combining recent methodologies in polymerase evolution, it is likely that multiple mutants can be obtained to improve metrics for AT rich and/or GC rich regions. While one of the major advantages of the sequencing chemistry set forth herein is the exploitation of natural biochemistry, it would also be possible to potentially improve or otherwise modify base calling by using single labeled substrates and a processive polymerase.

In addition to secondary structure impacting the enzyme/DNA binding kinetics leading to variability that could impact base calling, the fluidics scheme can be adjusted to suit the chemistry being used. Syringe pump and flow cell design can impact the consistency of flow profiles for individual cycles and across the FOV. Variations in flow can introduce different kinetic profiles from across clusters and cycles. Since the flow and mixing is directly tied to the $k_1$, a lack of synchronization can have an apparent effect of washing out the signal and the amplitude may be compromised leading to false negatives in extreme instances. As one example, benefits can be gained from implementing a pressurized system and valving similar to those currently used in pyrosequencing methods. With a pressurized system, well-timed valving and a flow cell designed specifically to insure fast mixing, the uniformity of both the flow and synchronization can be improved, and subsequently the sequencing metrics.

As mentioned an advantage to the approach presented herein is the use of natural biochemistry and the evolvable nature of the chemistry. In terms of sequencing metrics, the natural biochemistry suggests that it is possible to achieve long read lengths and furthermore, the speed of the chemistry is influences by the fluidics. Relying on precedent and POC demonstrated in stopped flow kinetics, by choosing the proper enzyme, substrate combination and fluidic scheme, it is conceivable that the cycle times for this chemistry can be reduced to 1 base per second. At these rates, this sequencing chemistry would combine the advantages of the speed of single molecule formats, the accuracy of ensemble formats (e.g. clusters), and the read lengths of natural biochemistry sequencing technologies.

Although sequencing chemistry embodiments have been exemplified herein in the context of optical detection schemes, it possible to use non-fluorescence or even non-optical detection schemes. Examples of these detection schemes include nanoparticle probes combined with a light scattering technique. Combining this scheme with a sensor chip, a scalable low cost instrument could be constructed. As another example the sequencing chemistry described herein can employ lightless detection technologies combined with a fast, long read, accurate, natural sequencing chemistry.

Materials and Methods
Instrumentation

Figure 22:
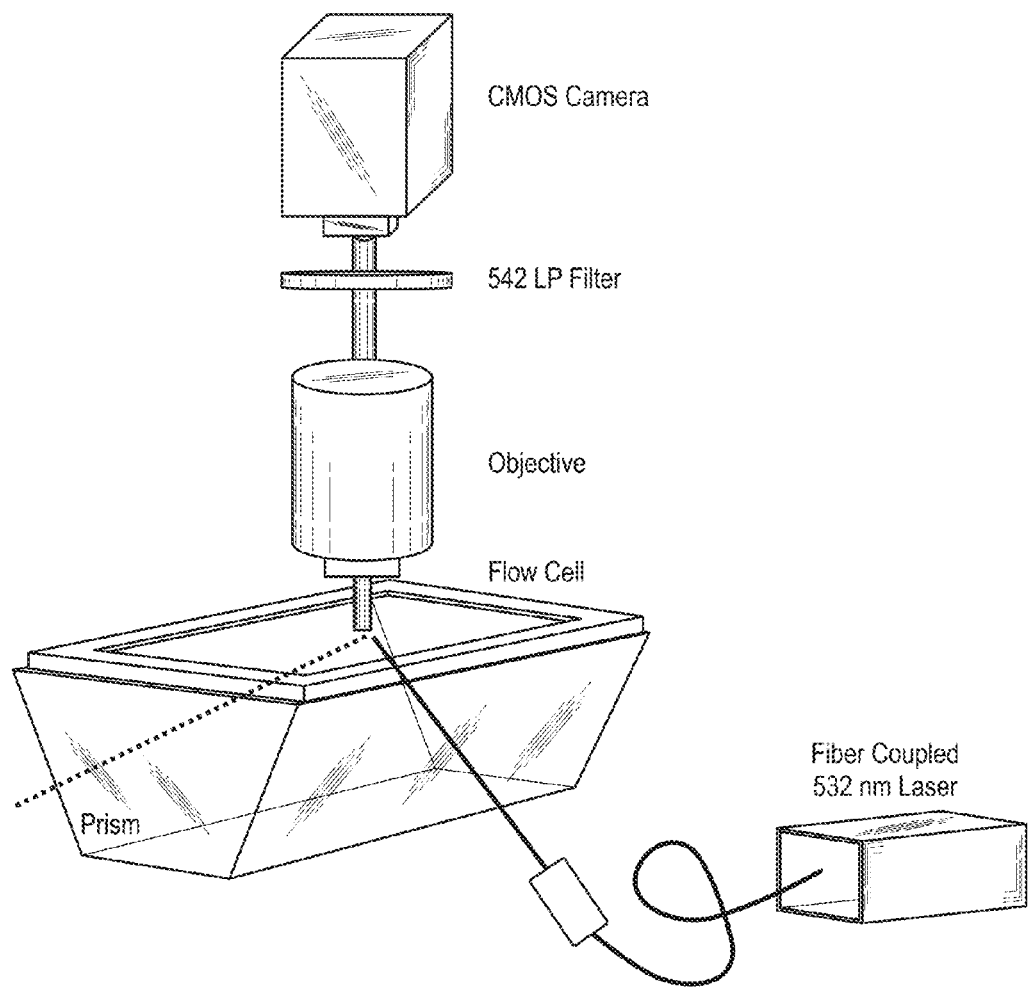
FIG. 22 shows an exemplary detection apparatus for a sequencing device.

Data was collected on a modified Genome Analyzer I (GA) from Illumina, Inc. (San Diego, Calif.). The commercial instrument is described in Bentley, et al. *Nature* 456:53-59 (2008) and U.S. Pat. No. 8,241,573, each of which is incorporated herein by reference in its entirety. Modifications were made to the instrument to accommodate a synchronized sequencing scheme as shown in FIG. 22 and as described here. Optical components were modified to improve the collection efficiency for Cy3 dye that was chosen for these experiments. Specifically, the filter turret was modified to house a single 540 LP filter. The illumination scheme is the traditional GA TIRF configuration as has been previously described, but the incident power density was approximated to be 0.1 W/cm$^2$. The standard GA camera was replaced with a Hamamatsu ORCA-Flash2.8 CMOS camera to insure accurate time resolution for pre-steady state kinetic responses. Data was typically collected at 10 frames/sec unless otherwise noted. Samples were introduced with a flow rate of approximately 4 ml/min using the GA syringe pump configuration.

Flow Cell Preparation

Cluster amplification was performed according to the manufacturer's protocol using paired end cluster chemistry and paired end flow cells V4. Template concentrations were determined to achieve a cluster density of approximately 20,000 clusters/mm$^2$. All calibration experiments to optimize sequencing conditions (NaCl and dNTP titration experiments) were performed using a template with the following insertion sequence: CTAAGTTTTTCACTTAAAGAGGCTTAGG-GAAAGTGATTTTTAAAGAGTCACT GTTACATGG-TAATATGCCGTTCA (SEQ ID NO: 7). This template was cluster amplified to create a monotemplate flow cell.

Expression and Purification of BSU Pol I

The Pol I gene from *Bacillus subtilis* was codon optimized and purchased from DNA2.0. The gene was then PCR amplified and subcloned into a pET15b vector containing an N-terminal 6×HIS tag followed by a thrombin cleavage site (MGSSHHHHHHSSGLVPRGSH (SEQ ID NO: 8)). Site directed quikchange mutagenesis was performed to replace the second serine following the 6×HIS tag with a cysteine (MGSSHHHHHHSCGLVPRGSH (SEQ ID NO: 9)). This construct was used to express BSU polymerase with an N-terminal 6×HIS tag and unique exposed cysteine residue for maleimide chemistry labeling. The pET15b-BSU was confirmed by sequencing and transformed into BL21 Star (DE3) expression cells from Invitrogen. The transformed cells were cultured at 37° C. in 2.8L Fernbock flasks until an OD$_{600}$ of 0.8 was reached. Protein expression was then induced by addition of 1 mM IPTG, followed by 3 hours of additional growth. The cultures were then centrifuged at 7000 rpm for 20 minutes. 4L Cultures typically yielded 25 g of wet cell pellet. Cell pellets were stored at −80° C. until purification.

Bacterial cell lysis was performed by resuspending the frozen cultures in 10× w/v lysis buffer (Tris pH 8.0, 500 mM NaCl, 1 mM EDTA, 1 mM DTT). EDTA free protease inhibitor (Roche) was added to the resuspended cell pellet. All lysis and purification steps were performed at 4° C. The resuspended culture was passed through a microfluidizer four times to complete cell lysis. The lysate was then centrifuged at 20,000 rpm for 20 minutes to remove cell debris. Polyethylenimine (final concentration 0.5%) was added to the supernatant slowly with stirring for 45 minutes to precipitate bacterial nucleic acid. The lysate was centrifuged at 20,000 rpm for 20 minutes; the pellet was discarded. The lysate was then ammonium sulfate precipitated using two volumes of cold saturated $(NH_4)_2SO_4$ in sterile $dH_2O$. The precipitated protein was centrifuged at 20,000 rpm for 20 minutes. The protein pellets were resuspended in 250mL of Buffer A (50 mM Tris pH 8.0, 300 mM NaCl, 20 mM imidazole, 1 mM EDTA, 1 mM DTT). The resuspended lysate was then purified using a 5 mL HisTrap FastFlow column (GE) pre-equilibrated in buffer A. The column was eluted using a 100 mL gradient from 20 mM to 1M imizadole. Peak fractions were pooled and diluted with buffer C (Tris pH 7.5, 1 mM EDTA, 1 mM DTT) until the conductivity was equal to buffer D (Tris pH 7.5, 50 mM NaCl, 1 mM EDTA, 1 mM DTT). The pooled fractions were then loaded onto a 5 mL HiTrap Heparin Fastflow column. The column was then eluted using a 100 mL gradient from 50 mM to 1M NaCl. Peak fractions were pooled and concentrated prior to fluorescent labeling.

Labeling BSU Pol I with Cy3-Maleimide

Purified BSU Pol I was buffer exchanged into conjugation buffer (50 mM ACES pH 7.4, 20 mM NaCl, 0.2% Tween-20) using Illustra NAP G-25 columns (GE). The protein was then concentrated to 100 µM and conjugated to Cy3-Maleimide reactive dye (GE) using the manufacturers protocol. The labeling reaction was incubated at 4° C. for 16 hours, followed by diafiltration and concentration using vivaspin 6 30 kDa concentrators (GE). Final buffer exchange and excess Cy3-Maleimide removal was performed using Illustra NAP G-25 columns pre-equilibrated in storage buffer (50 mM ACES pH 7.4, 20 mM NaCl, 0.2% Tween-20, 1 mM DTT). Molar labeling efficiency was calculated spectrophotometrically using extinction coefficients of 150,000 $M^{-1}$ $cm^{-1}$ and 55,810 $M^{-1}$ $cm^{-1}$ for Cy3 and BSU Pol I, respectively. Protein lots with labeling efficiencies of ≥95% were aliquoted and flash frozen in liquid $N_2$ and stored at −80° C. until use.

Enzyme Validation

Enzyme activity was determined by burst assay. Briefly, 200 nM of enzyme (determined by Bradford assay) was pre-incubated with 1000 nM duplex DNA in reaction buffer (10 mM Tris pH 8.0, 50 mM NaCl, 10 mM $MgCl_2$, 1 mM DTT). Duplex DNA was constructed by annealing 1:1.1 molar ratios of primer (5'-Cy5-GCTTGCACAGGGCCTCGAC-3' (SEQ ID NO: 10)) and template: (5'CGTTAGTAAGGTCGAGGCCCTGTGCAAGC-3' (SEQ ID NO: 11)) oligonucleotides (purchased from IDT, Coralville, Iowa). The enzyme DNA complex was then rapidly mixed with 100 µM dCTP for various times from 0 to 2 seconds at 37° C. using a RQF-4 Rapid Quench Flow (KinTek Corp., Austin, Tex.). Reactions were quenched by addition of 500 mM EDTA. Product formation (n+1) was separated from substrate (n) by 15% denaturing PAGE. Products were visualized using a Typhoon imager and quantified using ImageQuant TL (GE) and Grafit 7.0 (Erithacus). Only enzyme lots possessing >90% activity by burst assay were used in subsequent pre-steady state and GA analysis.

Pre-Steady State Analysis

The nucleotide concentration dependence of product formation was determined by rapid quench analysis using a RQF-4 Rapid Quench Flow (KinTek Corp., Austin, Tex.). A pre-incubated complex of 1000 nM enzyme and 200 nM duplex DNA was rapidly mixed at 45° C. with various concentrations of dCTP in high salt reaction buffer (20 mM ACES pH 7.4, 300 mM NaCl, 1 µM Acetylated BSA (Ambion a subsidiary of Life Technologies, Carlsbad, Calif.), 10 mM $MgSO_4$, 1 mM TCEP). Reactions were quenched by addition of 500 mM EDTA and quantified as previously described. The assay was repeated using a mismatched dATP:dG for extension. Mismatched product formation required nucleotide concentrations from 100 µM to 3000 µM and longer reaction incubation times up to 60 minutes to observe product formation. The product formation at each nucleotide concentration was fit by non-linear regression to a single exponential equation (product=$Ae^{kt}$+C). The nucleotide concentration dependence of the resulting rates (k) were then fit to a hyperbolic function ($k_{observed}=k_{max} X[S]/K_{d,app}+[S]$).

The effects of NaCl and nucleotide concentration on transient Enzyme-DNA binding was observed using fluorescence stopped flow techniques. A pre-incubated complex of 600 nM fluorescently-labeled enzyme and 100 µM dCTP was rapidly mixed with duplexed DNA in high salt reaction buffer (20 mM ACES pH 7.4, 1 µM Acetylated BSA, 0.02% Tween-20, 10 mM $MgSO_4$, 1 mM TCEP). The final NaCl concentration of the buffer was varied from 62.5 mM to 325 mM. The duplexed DNA was assembled by annealing the previously described template oligo with a primer containing a fluorescein modified thymidine (shown in bold and underlined) 5 bases from the incorporation site (5'- GCTTGCACAGGGCC<u>T</u>CGAC-3' (SEQ ID NO: 10)). Fluorescein is an environmentally sensitive dye that is quenched upon protein interaction. The transient enzyme-DNA association was monitored by excitation of fluorescein at 495nm and fluorescent emission using a 520 nm high pass filter. The nucleotide concentration dependence on transient enzyme-DNA binding was observed by pre-incubating 600 nM of fluorescently labeled enzyme with various concentration of dCTP from 0 to 80 µM in high salt reaction buffer containing 300 mM NaCl. The reaction was started by rapid mixing with 400 nM fluorescein labeled DNA. All concentrations were final after mixing.

Base Discrimination Optimization on GA

Based on the pre-steady state analysis, the nucleotide concentration dependence of product formation was determined by titrating nucleotide concentration under a high salt condition. The effects of [NaCl] and [dNTP] on nucleotide (correct vs. incorrect) and homopolymer discrimination (max amplitude/steady state amplitude) were determined by performing titrations of one of [dNTP] or [NaCl] while holding the other constant. From pre-steady state analysis, the [NaCl] titration was performed by holding the [dNTP] fixed at 300 µM, which was determined to be the peak concentration before misincorporation becomes problematic for dCTP under the conditions tested. In order to demonstrate a qualitative correlation between stopped flow results, the [NaCl] titrations were performed over the range of 62-375 mM using [dCTP] as the correct nucleotide and [dGTP] as the incorrect nucleotide. Reactions were performed by pumping 250 µl of reaction buffer with the correct (dCTP) or incorrect nucleotide (dGTP) at 300 µM through the flow cell. In addition to the respective nucleotides, the reaction buffer components also included the following: 50 mM ACES pH 7.4, 1 µM Acetylated BSA, 0.02% Tween-20, 10 mM $MgSO_4$, 1 mM TCEP, 125 nM SSB (Epicentre, a subsidiary of Illumina, Inc., San Diego, Calif.), 2 mM $CaCl_2$, 100 nM glucose oxidase, 1.5 µM catalase, 56 mM glucose. The final NaCl concentration of the buffer was varied from 62.5 mM to 375 mM. Two 250 µl wash cycles were introduced into the flow cell after the reaction mix. The wash 1 buffer components included the following: 50 mM ACES pH 7.4, 1 µM Acetylated BSA, 0.02% Tween-20, 2.5 mM EDTA, 300 mM NaCl. Wash 2 buffer components included the following: 250 mM ACES pH 7.4, 1 µM Acetylated BSA, 0.02% Tween-20, 1 mM TCEP, 125 nM SSB (Epicentre), 100 mM NaCl.

In order to optimize the reaction conditions for nucleotide concentration, the reactions were performed at 300 mM NaCl and the correct and incorrect nucleotide concentrations were varied from 1-500 µM. Reaction conditions and wash components were the same as those described above with the exception of the changes to nucleotide and salt concentrations respectively.

Sequencing Using Pre-steady State Enzyme DNA Binding Kinetics

Sequencing reactions were run using a mixture of synthetic templates having different nucleotide sequences. Templates were mixed to insure approximately equal cluster numbers for each respective template. Sequencing reactions were run on the previously described modified GA instrumentation and analysis was performed as described below. Nucleotides were introduced into the flow cell using the following sequencing 'C', 'T', 'A', 'G' with the following concentrations: 100 µM, 300 µM, 100 µM, and 100 µM, respectively. In addition to the respective nucleotides, the final sequencing reaction buffer components also included the following: 50 mM ACES pH 7.4, 1 µM Acetylated BSA, 0.02% Tween-20, 10 mM MgSO$_4$, 1 mM TCEP, 125 nM SSB (Epicentre), 2 mM CaCl$_2$, 100 nM glucose oxidase, 1.5 µM catalase, 56 mM glucose, 375 mM NaCl. Two 250 µl wash cycles were introduced into the flow cell after the reaction mix. The sequencing reaction wash 1 buffer components included the following: 50 mM ACES pH 7.4, 1 µM Acetylated BSA, 0.02% Tween-20, 2.5 mM EDTA, 300 mM NaCl. The sequencing reaction wash 2 buffer components included the following: 50 mM ACES pH 7.4, 1 µM Acetylated BSA, 0.02% Tween-20, 1 mM TCEP, 125 nM SSB (Epicentre), and 150 mM NaCl.

Software and Computation

Using non-ideal flow conditions, diffusion steps can produce a temporal concentration change for reaction components that are slower than the ideal flow. Thus, the concentration of the polymerase enzyme becomes a function of time. The background trace from each feature is extracted from the movie at pixels close to the foreground pixels. The amplitude of the background pixel corresponds to the concentration of the fluorophore. For example, if the polymerase is labeled the background amplitude is proportional to the polymerase concentration [E].

In spot detection, the locations of the clusters were determined on an "average image", which were computed by averaging the first 100 frames of the TIFF movie collected. This average image was filtered with a Difference of Gaussian (DoG) filter, with a center standard deviation of 0.7 pixels and a surround standard deviation of 2 pixels. Center pixel locations of clusters were defined as the regional maximum on the filtered image on a 4-connected neighborhood. Within a 5-by-5 pixel neighborhood around the center pixel, background pixels were chosen, which are defined as pixels whose DoG response is less than the Otsu's threshold and more than 2 pixels away from the center pixel. For each cluster, a variable number of background pixels were chosen. The detected spots were further filtered with 3 conditions: first, the center pixel of a cluster had to be brighter than a threshold determined by Otsu's method; secondly, using a connected component analysis, a cluster had to be between 5 and 400 pixels in size; and thirdly, the center pixel of a cluster had to be brighter than the mean brightness of its background pixels plus 3 times the brightness standard deviation.

When extracting time series from each cluster, each frame of the movie was filtered with a Guassian filter with a standard deviation of 1 pixel. The intensity value at each center pixel is extracted as the foreground intensity. The background intensity of a cluster is extracted as the mean of background pixels' intensities. For each flow, each cluster is basecalled using the background subtracted signal.

Throughout this application various publications, patents and patent applications have been referenced. The disclosures of these publications in their entireties are hereby incorporated by reference in this application in order to more fully describe the state of the art to which this invention pertains.

The term "comprising" is intended herein to be open-ended, including not only the recited elements, but further encompassing any additional elements.

Although the invention has been described with reference to the examples provided above, it should be understood that various modifications can be made without departing from the invention. Accordingly, the invention is limited only by the claims.

---

What is claimed is:

1. A method of distinguishing nucleotide sequences for different nucleic acid molecules, comprising
   (a) mixing a plurality of different nucleic acid molecules with polymerase molecules and nucleotide molecules to cause binding of the polymerase molecules to the nucleic acid molecules,
   wherein the different nucleic acid molecules are attached to a surface in the form of an array of nucleic acid features at a density of at least 100 features/$cm^2$, and
   wherein the mixing comprises stopped flow delivery of the polymerase molecules to the nucleic acid features;
   (b) monitoring the binding of the polymerase molecules to the nucleic acid features at several points during a pre-equilibrium time period, thereby determining a transient state of the polymerase molecules at the nucleic acid features; and
   (c) identifying nucleic acid features of the array that correctly incorporate the nucleotide molecules based on the transient state of the polymerase molecules at the nucleic acid features, thereby distinguishing the nucleotide sequences for the different nucleic acid molecules.

2. The method of claim 1, wherein (b) comprises determining pre-steady state kinetic rate profiles of the binding of the polymerase molecules to the nucleic acid features.

3. The method of claim 2, wherein the monitoring of the pre-steady state kinetic rate profiles occurs before, during, and after correct incorporation of the nucleotide molecules into the nucleic acid features.

4. The method of claim 2, wherein (c) comprises identifying the nucleic acid features of the array that correctly incorporate the nucleotide molecules based on the transient state of the polymerase molecules at the nucleic acid features, thereby distinguishing the nucleotide sequences for the different nucleic acid molecules based on the pre-steady state kinetic rate profiles.

5. The method of claim 1, further comprising
   (d) removing the polymerase molecules from the nucleic acid features, thereby providing restored features;
   (e) mixing the restored features with polymerase molecules and a second species of nucleotide molecules, wherein the second species of nucleotide molecules is different from the species of nucleotide molecules in (a); and
   (f) repeating (b) and (c) for the restored features, thereby distinguishing the nucleotide sequences for the different nucleic acid molecules.

6. The method of claim 5, wherein the method is performed sequentially for four different nucleotide species.

7. The method of claim 6, wherein the method is repeated several times to determine the nucleotide sequences for the different nucleic acid molecules.

8. The method of claim 5, wherein (d) further comprises removing the nucleotide molecules from the nucleic acid features.

9. The method of claim 1, wherein the mixing comprises stopped flow delivery of the nucleotide molecules to the nucleic acid features.

10. The method of claim 1, wherein the one or more of the nucleotide molecules comprise reversible blocking moieties.

11. The method of claim 10, further comprising
   (d) removing the polymerase molecules from the nucleic acid features, and removing the blocking moieties at the nucleic acid features that correctly incorporate the nucleotide molecules, thereby providing restored features;
   (e) mixing the restored features with polymerase molecules and a second species of nucleotide molecules, wherein the second species of nucleotide molecules is different from the species of nucleotide molecules in (a); and (f) repeating (b) and (c) for the restored features, thereby distinguishing the nucleotide sequences for the different nucleic acid molecules.

12. The method of claim 11, wherein the method is performed sequentially for four different nucleotide species that comprise reversible blocking moieties.

13. The method of claim 12, wherein the method is repeated several times to determine the nucleotide sequences for the different nucleic acid molecules.

14. The method of claim 1, wherein the transient state is determined from the time duration for the binding to reach equilibrium.

15. The method of claim 1, wherein the determining of the transient state comprises determining binding rate constants for the binding of the polymerase molecules to the nucleic acid features.

16. The method of claim 1, wherein the determining of the transient state comprises determining catalytic rate constants for incorporation of the nucleotide molecules into the nucleic acid features.

17. The method of claim 1, wherein the polymerase molecules comprise labels and the monitoring in (b) comprises detecting the labels.

18. The method of claim 1, wherein the nucleotide molecules comprise labels and the monitoring in (b) comprises detecting the labels.

19. The method of claim 1, wherein the mixing comprises stopped flow delivery of the polymerase molecules and the nucleotide molecules to the nucleic acid features.

20. The method of claim 1, wherein each feature of the array comprises only a single nucleic acid molecule.

21. The method of claim 1, wherein each feature of the array comprises a population of molecules of the same nucleic acid species.

22. The method of claim 1, wherein the stopped flow delivery has a dead time of less than 2 milliseconds.

23. The method of claim 1, wherein the mixing is achieved at a flow rate of at least 20 ml/min.

* * * * *

SEQUENCE LISTING

```
<160> NUMBER OF SEQ ID NOS: 11

<210> SEQ ID NO 1
<211> LENGTH: 43
<212> TYPE: DNA
<213> ORGANISM: Artificial Sequence
<220> FEATURE:
<223> OTHER INFORMATION: non-naturally occuring sequence

<400> SEQUENCE: 1
cttgcgtgga cacgttcgcg aacgtgtcca cgcaaggaat tcg            43

<210> SEQ ID NO 2
<211> LENGTH: 79
<212> TYPE: DNA
<213> ORGANISM: Artificial Sequence
<220> FEATURE:
<223> OTHER INFORMATION: non-naturally occuring sequence

<400> SEQUENCE: 2
aaaaagggaa aactccttaa accctttgga accccgtttt accccccgaga cgacgcggta    60 ggcgccagat atgcgatcc                                                 79

<210> SEQ ID NO 3
<211> LENGTH: 11
<212> TYPE: DNA
<213> ORGANISM: Artificial Sequence
<220> FEATURE:
<223> OTHER INFORMATION: non-naturally occuring sequence

<400> SEQUENCE: 3
gggggtaaaa c                                               11
```

```
<210> SEQ ID NO 4
<211> LENGTH: 183
<212> TYPE: DNA
<213> ORGANISM: Artificial Sequence
<220> FEATURE:
<223> OTHER INFORMATION: non-naturally occuring sequence

<400> SEQUENCE: 4
aatgatacgg cgaccaccga gatctacact ctttccctac acgacgctct tccgatctcc      60
tacgcgagta ctatatacgt acatgcgtgt atgcgtacgt actacgtaca cgtgacgtta     120
gaagatcgga agagcggttc agcaggaatg ccgagaccga tctcgtatgc cgtcttctgc     180
ttg                                                                  183

<210> SEQ ID NO 5
<211> LENGTH: 32
<212> TYPE: DNA
<213> ORGANISM: Artificial Sequence
<220> FEATURE:
<223> OTHER INFORMATION: non-naturally ocurring sequence

<400> SEQUENCE: 5
cgttagtaac ctcgaggcaa cttagcctcg ag                                   32

<210> SEQ ID NO 6
<211> LENGTH: 92
<212> TYPE: DNA
<213> ORGANISM: Artificial Sequence
<220> FEATURE:
<223> OTHER INFORMATION: non-naturally occuring sequence

<400> SEQUENCE: 6
aatgatacgg cgaccaccga gatctacact ctttccctac acgacgctct tccgatctcc      60
ccctacgcat ctcgtatgcc gtcttctgct tg                                   92

<210> SEQ ID NO 7
<211> LENGTH: 75
<212> TYPE: DNA
<213> ORGANISM: Artificial Sequence
<220> FEATURE:
<223> OTHER INFORMATION: non-naturally occuring sequence

<400> SEQUENCE: 7
ctaagttttt cacttaaaga ggcttaggga aagtgatttt taaagagtca ctgttacatg      60
gtaatatgcc gttca                                                      75

<210> SEQ ID NO 8
<211> LENGTH: 20
<212> TYPE: PRT
<213> ORGANISM: Artificial Sequence
<220> FEATURE:
<223> OTHER INFORMATION: non-naturally occuring sequence

<400> SEQUENCE: 8

Met Gly Ser Ser His His His His His His Ser Ser Gly Leu Val Pro
1               5                   10                  15

Arg Gly Ser His
            20

<210> SEQ ID NO 9
<211> LENGTH: 20
<212> TYPE: PRT
<213> ORGANISM: Artificial Sequence
```

```
<220> FEATURE:
<223> OTHER INFORMATION: non-naturally occuring sequence

<400> SEQUENCE: 9

Met Gly Ser Ser His His His His His His Ser Cys Gly Leu Val Pro
1               5                   10                  15

Arg Gly Ser His
            20

<210> SEQ ID NO 10
<211> LENGTH: 21
<212> TYPE: DNA
<213> ORGANISM: Artificial Sequence
<220> FEATURE:
<223> OTHER INFORMATION: non-naturally occuring sequence

<400> SEQUENCE: 10
cygcttgcac agggcctcga c                                         21

<210> SEQ ID NO 11
<211> LENGTH: 29
<212> TYPE: DNA
<213> ORGANISM: Artificial Sequence
<220> FEATURE:
<223> OTHER INFORMATION: non-naturally occuring sequence

<400> SEQUENCE: 11
cgttagtaag gtcgaggccc tgtgcaagc                                 29
```